(12) United States Patent
Ohya et al.

(10) Patent No.: US 9,290,510 B2
(45) Date of Patent: Mar. 22, 2016

(54) POLYMERIC COMPOUND AND ELECTRONIC ELEMENT

(75) Inventors: Kenichiro Ohya, Tsukuba (JP); Ken Yoshimura, Tsukuba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 733 days.

(21) Appl. No.: 13/504,030

(22) PCT Filed: Oct. 22, 2010

(86) PCT No.: PCT/JP2010/069234
§ 371 (c)(1),
(2), (4) Date: Apr. 25, 2012

(87) PCT Pub. No.: WO2011/052702
PCT Pub. Date: May 5, 2011

(65) Prior Publication Data
US 2012/0205593 A1 Aug. 16, 2012

(30) Foreign Application Priority Data
Oct. 29, 2009 (JP) ................................ 2009-248796

(51) Int. Cl.
| | |
|---|---|
| *C08G 61/12* | (2006.01) |
| *C07D 495/04* | (2006.01) |
| *C07D 519/00* | (2006.01) |
| *C08L 65/00* | (2006.01) |
| *B82Y 10/00* | (2011.01) |
| *H01L 51/00* | (2006.01) |
| *C09B 69/10* | (2006.01) |
| *H01L 51/05* | (2006.01) |
| *H01L 51/42* | (2006.01) |

(52) U.S. Cl.
CPC .............. *C07D 495/04* (2013.01); *B82Y 10/00* (2013.01); *C07D 519/00* (2013.01); *C08G 61/126* (2013.01); *C09B 69/101* (2013.01); *C09B 69/102* (2013.01); *C09B 69/109* (2013.01); *H01L 51/0036* (2013.01); *H01L 51/0043* (2013.01); *C08G 2261/312* (2013.01); *C08G 2261/3243* (2013.01); *C08G 2261/3246* (2013.01); *C08G 2261/411* (2013.01); *H01L 51/0047* (2013.01); *H01L 51/0558* (2013.01); *H01L 51/4253* (2013.01)

(58) Field of Classification Search
CPC .... C08G 61/12; C07D 495/04; C07D 519/00; C08L 65/00
USPC ........ 252/500, 501.1, 519.33, 519.4; 528/373
See application file for complete search history.

(56) References Cited

U.S. PATENT DOCUMENTS

2007/0014939 A1   1/2007 Gaudiana et al.
2007/0246094 A1 * 10/2007 Brabec et al. ................. 136/244

FOREIGN PATENT DOCUMENTS

| CN | 101407574 A | 4/2009 |
|---|---|---|
| JP | 2006-278682 A | 10/2006 |
| JP | 2009-506519 A | 2/2009 |
| JP | 2009-533878 A | 9/2009 |
| WO | 2010/016986 A1 | 2/2010 |

OTHER PUBLICATIONS

Zhengguo Zhu et al, "Panchromatic Conjugated Polymers Containing Alternating Donor/Acceptor Units for Photovoltaic Applications", Macromolecules, 2007, pp. 1981-1986, vol. 40.*
Translation of the International Preliminary Report on Patentability and Written Opinion mailed Jun. 21, 2012 in International Application No. PCT/JP2010/069234.
Notification of reason for refusal issued Jun. 24, 2014 in Japanese Patent Application No. 2010-243451 with English translation.
Extended European Search Report issued Apr. 4, 2013 in European Patent Application No. 10826834.3.

(Continued)

*Primary Examiner* — Brian P Mruk
(74) *Attorney, Agent, or Firm* — Sughrue Mion, PLLC

(57) ABSTRACT

A polymer compound including a structural unit represented by formula (I) or a structural unit represented by formula (III) and a structural unit represented by formula (II) has high photoelectric conversion efficiency when used in an organic photoelectric conversion device.

$$-Ar^1-Ar^2-Y- \quad (I)$$
$$\underset{Z}{\underbrace{\phantom{Ar^1-Ar^2}}}$$

wherein $Ar^1$ and $Ar^2$ are the same or different and represent trivalent heterocyclic group; Z represents a divalent group; Y represents a divalent heterocyclic group;

$$-Ar^1-Ar^2-Y-Ar^1-Ar^2- \quad (III)$$
$$\underset{Z}{\underbrace{\phantom{Ar^1-Ar^2}}} \quad \underset{Z}{\underbrace{\phantom{Ar^1-Ar^2}}}$$

wherein $Ar^1$ and $Ar^2$ are the same or different and represent trivalent heterocyclic group; Z represents a divalent group; Y represents a divalent heterocyclic group; two $Ar^1$s may be the same or different; two $Ar^2$s may be the same or different; and two Z's may be the same or different.

$$-D- \quad (II)$$

wherein D represents an arylene group or a heteroarylene group having a fused ring, provided that a divalent heterocyclic group represented by Y is different from a group represented by D.

10 Claims, No Drawings

(56) References Cited

OTHER PUBLICATIONS

Adam J. Moule, et al., "Two Novel Cyclopentadlthiophene-Based Alternating Copolymers as Potential Donor Components for High-Efficiency Bulk-Heterojunction-Type Solar Cells," Chemistry of Materials, vol. 20, No. 12, Jun. 1, 2008, pp. 4045-4050, XP055056353.

Zhengguo Zhu, et al., "New Polymers for Optimizing Organic Photovoltaic Cell Performances," Journal of Macromolecular Science, Part A—Pure and Applied Chemistry, Marcel Dekker Inc., US, vol. 44, No. 12, Dec. 1, 2007, pp. 1249-1253, XP008111330.

Database CA [Online] Chemical Abstracts Service, Columbus, OH, US, Apr. 20, 2009, Geng, Yanhou and Yue, Wei, "Donor-receptor-type conjugated polymer containing dithienopyrrole and its preparation and use", XP002693897.

Pierre M. Beaujuge, et al., "Tailoring Structure—Property Relationships in Dithienosilole-Benzothiadiazole Dono-Acceptor Copolymers", Journal of the American Chemical Society, vol. 131, No. 22, Jun. 20, 2009, pp. 7514-7515, XP55056650.

Bram P. Karsten, et al., "Electronic structure of small band gap oligomers based on cyclopentadithiophenes and acceptor units", Journal of Materials Chemistry, vol. 19, No. 30, Apr. 28, 2009, pp. 5343-5350, XP55056654.

Kuang-Chich Li, et al., "Tunable Novel Cyclopentadithiophene-Based Copolmers Containing Various Numbers of Bithiazole and Thienyl Units for Organic Photovoltaic Cell Applications", Macromolecules, 2009, pp. 3681-3693, vol. 42.

A. J. Moulé, "Two Novel Cyclopentadithiophene-Based Alternating Copolymers as Potential Donor Components for High-Efficiency Bulk-Heterojunction-Type Solar Cells", Chem. Mater., 2008, pp. 4045-4050, vol. 20.

Zhengguo Zhu, et al., "Panchromatic Conjugated Polymers Containing Alternating Donor/Acceptor Units for Photovoltaic Applications", Macromolecules, 2007, pp. 1981-1986, vol. 40.

Notice of Reasons for Rejection issued Feb. 3, 2015 in corresponding Japanese Patent Application No. 2010-243451 with translation.

Brant P. Karsten, et al., "Electronic structure of small band gap oligomers based on cyclopentadithiophenes and acceptor units", Journal of Materials Chemistry, vol. 19, No. 30, Aug. 14, 2009, pp. 5343-5350.

* cited by examiner

POLYMERIC COMPOUND AND ELECTRONIC ELEMENT

CROSS REFERENCE TO RELATED APPLICATIONS

This application is a National Stage of International Application No. PCT/JP2010/069234 filed Oct. 22, 2010, claiming priority based on Japanese Patent Application Nos. 2009-248796 filed Oct. 29, 2009, the contents of all of which are incorporated herein by reference in their entirety.

TECHNICAL FIELD

The present invention relates to a polymer compound, and an electronic device using the same.

BACKGROUND ART

Since a polymer compound containing a n-conjugated structure absorbs light in a visible light range and peripheral regions of visible light and also has emission characteristics, conduction characteristics, semiconductor characteristics and the like, an examination of the polymeric compound on application to electronic devices such as an organic electroluminescence device, a switching device, a photoelectric conversion device and the like has been made.

A polymer compound, which has two or more kinds of structural unit and also contains a n-conjugated structure, has plural functions derived from each structural unit, and thus the polymer compound is expected as a compound whose advancement in performance can be anticipated. Therefore, an application study as a material suited for use in an electronic device has made progress compared with a homopolymer containing one kind of a structural unit.

There has been proposed, as a polymer compound which contains two kinds of structural unit and also contains n-conjugated structure, a polymer compound composed of a structural unit represented by formula (A) and a structural unit represented by formula (B) (US2007-014939A).

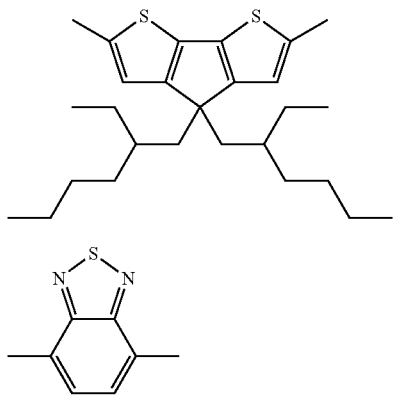

DISCLOSURE OF THE INVENTION

However, there is a problem that a photoelectric conversion device comprising an organic layer containing the above polymer compound has low photoelectric conversion efficiency. The present invention provides a polymer compound in which photoelectric conversion efficiency of a photoelectric conversion device increases when used in a photoelectric conversion device.

That is, in a first aspect, the present invention provides a polymer compound containing a structural unit represented by formula (I) and a structural unit represented by formula (II)

wherein $Ar^1$ and $Ar^2$ are the same or different and represent trivalent heterocyclic group; Z represents a divalent group; Y represents a divalent heterocyclic group;

wherein D represents an arylene group or a heteroarylene group having a fused ring, provided that a divalent heterocyclic group represented by Y is different from a group represented by D.

In a second aspect, the present invention provides a polymer compound containing a structural unit represented by formula (III) and a structural unit represented by formula (II):

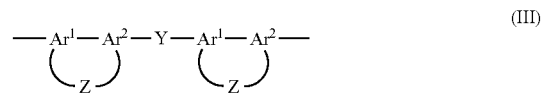

wherein $Ar^1$, $Ar^2$, Y and Z have the same meanings as defined above; two $Ar^1$s may be the same or different; two $Ar^2$s may be the same or different; and two Zs may be the same or different.

In a third aspect, the present invention provides a polymer compound, wherein a structural unit represented by formula (I) is a structural unit represented by formula (IV):

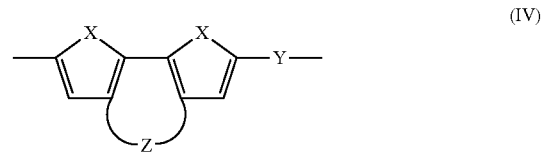

wherein X represents a sulfur atom, an oxygen atom, a selenium atom, —NH— or —N($R^a$)—; $R^a$ represents a substituent; Y and Z have the same meanings as defined above; and two Xs may be the same or different.

In a fourth aspect, the present invention provides a polymer compound, wherein a structural unit represented by formula (III) is a structural unit represented by formula (V):

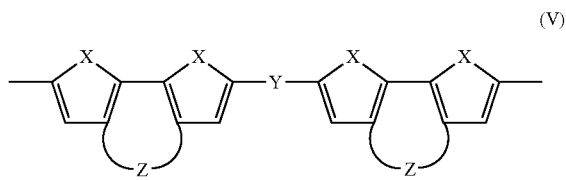

wherein X represents a sulfur atom, an oxygen atom, a selenium atom, —NH— or —N($R^a$)—; $R^a$ represents a substituent; Y and Z have the same meanings as defined above; four Xs may be the same or different; and two Zs may be the same or different.

In a fifth aspect, the present invention provides a polymer compound, wherein the divalent group represented by Z is each of groups represented by formulas (Z-1) to (Z-5) in a structural unit represented by formula (I) or a structural unit represented by formula (III):

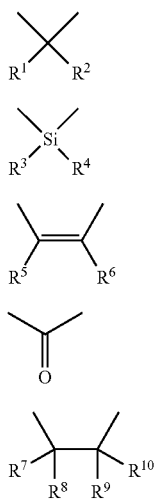

wherein $R^1$ to $R^{10}$ are the same or different and represent a hydrogen atom or a substituent.

In a sixth aspect, the present invention provides a polymer compound, wherein the divalent heterocyclic group represented by Y is each of groups represented by formulas (Y-1) to (Y-5) in a structural unit represented by formula (I) or a structural unit represented by formula (III):

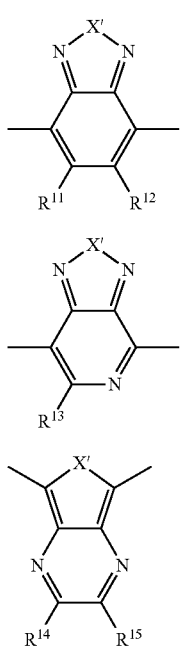
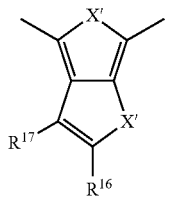
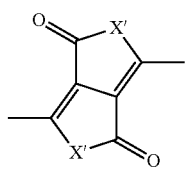

wherein X' represents a sulfur atom, an oxygen atom, a selenium atom, —NH— or —N($R^a$); $R^a$ represents a substituent; $R^{11}$ to $R^{17}$ are the same or different and represent a hydrogen atom or a substituent; $R^{11}$ and $R^{12}$ may be connected to each other to form a cyclic structure; and plural X's are present, they may be the same or different.

In a seventh aspect, the present invention provides a polymer compound, wherein a structural unit represented by formula (II) is each of groups represented by formulas (D-1) to (D-3):

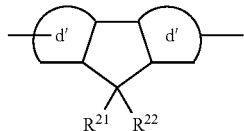
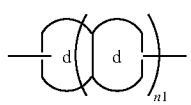
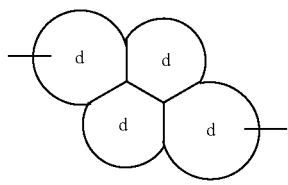

wherein d and d' ring in formulas (D-1) to (D-3) represents an aromatic ring which may have a substituent; plural d rings may be the same or different; plural d' rings may be the same or different; $R^{21}$ and $R^{22}$ are the same or different and represent a hydrogen atom or a substituent; and n1 is an integer of 1 or more.

In an eighth aspect, the present invention provides a polymer compound, wherein a structural unit represented by formula (II) is a group represented by formula (D-4):

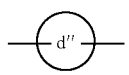

wherein d" ring represents a benzene ring which may have a substituent, a biphenyl ring which may have a substituent, a terphenyl ring which may have a substituent, or a fused ring containing a hetero atom, which may have a substituent.

In a ninth aspect, the present invention provides a polymer compound, wherein a polystyrene-equivalent number average molecular weight is 3,000 or more.

In a tenth aspect, the present invention provides a thin film comprising the polymer compound.

In an eleventh aspect, the present invention provides a composition comprising the polymer compound and an electron accepting compound.

In a twelfth aspect, the present invention provides the composition, wherein the electron accepting compound is a fullerene derivative.

In a thirteenth aspect, the present invention provides a thin film comprising the composition.

In a fourteenth aspect, the present invention provides a solution comprising the composition and a solvent.

In a fifteenth aspect, the present invention provides an electronic device using the thin film.

In a sixteenth aspect, the present invention provides a compound represented by formula (VI):

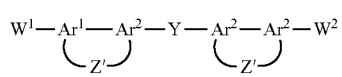

(VI)

wherein $Ar^1$ and $Ar^2$ are the same or different and represents a trivalent heterocyclic group; Z' represents a divalent hydrocarbon group; Y represents a divalent heterocyclic group; $W^1$ and $W^2$ are the same or different and represent a hydrogen atom, a halogen atom, an organotin residue, a boric acid residue or a boric acid derivative residue; two $Ar^1$s may be the same or different; two $Ar^2$s may be the same or different; and two Z's may be the same or different.

In a seventeenth aspect, the present invention provides a compound, wherein the compound represented by formula (VI) is a compound represented by formula (VII):

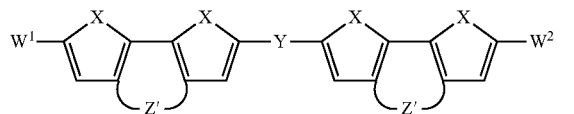

(VII)

wherein X represents a sulfur atom, an oxygen atom, a selenium atom, —NH— or —N(R$^a$)—; R$^a$ represents a substituent; Y, Z', $W^1$ and $W^2$ have the same meanings as defined above; and four Xs may be the same or different.

In an eighteenth aspect, the present invention provides a compound, wherein the divalent hydrocarbon group represented by Z' is a group represented by formula (Z-1), (Z-3) or (Z-5):

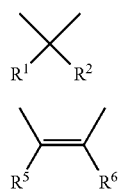

(Z-1)

(Z-3)

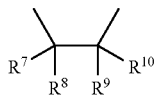

(Z-5)

wherein $R^1$, $R^2$, $R^5$ to $R^{10}$ are the same or different and represent a hydrogen atom or a substituent.

In a nineteenth aspect, the present invention provides a compound, wherein a divalent heterocyclic group represented by Y is each of groups represented by formulas (Y-1) to (Y-5):

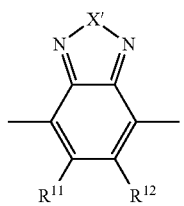

(Y-1)

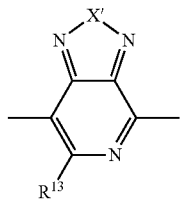

(Y-2)

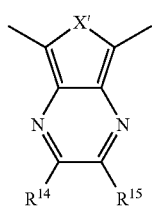

(Y-3)

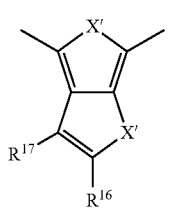

(Y-4)

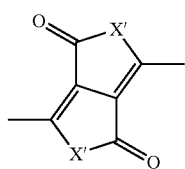

(Y-5)

wherein X' represents a sulfur atom, an oxygen atom, a selenium atom, —NH— or —N(R$^a$)—; R$^a$ represents a substituent; $R^{11}$ to $R^{17}$ are the same or different and represent a hydrogen atom or a substituent; $R^{11}$ and $R^{12}$ may be connected to each other to form a cyclic structure; and when plural X's are present, they may be the same or different.

In a twentieth aspect, the present invention provides a compound, which is represented by formula (VIII):

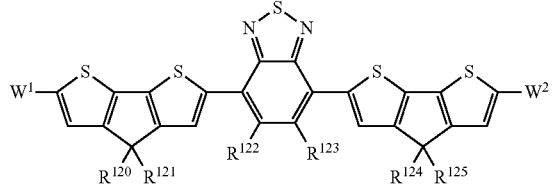
(VIII)

wherein $R^{120}$ to $R^{125}$ are the same or different and represent a hydrogen atom or a substituent, and $W^1$ and $W^2$ have the same meanings as defined above.

In a twenty first aspect, the present invention provides a compound represented by the formula formula (IX):

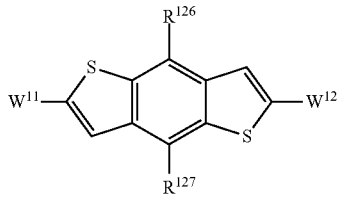
(IX)

wherein $R^{126}$ and $R^{127}$ are the same or different and represent a hydrogen atom or a substituent, and $W^{11}$ and $W^{12}$ are the same or different and represent a boric acid residue or a boric acid derivative residue.

MODE FOR CARRYING OUT THE INVENTION

The present invention will be described in detail.
The polymer compound containing a structural unit represented by formula (I), or a structural unit represented by formula (III) and a structural unit represented by formula (II)

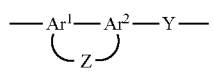
(I)

wherein $Ar^1$ and $Ar^2$ are the same or different and represent trivalent heterocyclic group; Z represents a divalent group; Y represents a divalent heterocyclic group.

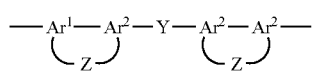
(III)

wherein $Ar^1$, $Ar^2$, Y and Z have the same meanings as defined above; two $Ar^1$s may be the same or different; two $Ar^2$s may be the same or different; and two Zs may be the same or different.

-D- (II)

wherein D represents an arylene group or a heteroarylene group having a fused ring, provided that a divalent heterocyclic group represented by Y is different from a group represented by D.

The trivalent heterocyclic group refers to an atomic group remaining after removing three hydrogen atoms from a heterocyclic compound, and the number of carbon atoms is usually from 2 to 60, preferably from 4 to 60, and more preferably from 4 to 20. Atoms contained in heterocycle may have a substituent, and the number of carbon atoms of the substituent is not included in the number of carbon atoms of the heterocyclic group. Herein, the heterocyclic compound refers to an organic compound in which elements constituting the ring are contained not only carbon atoms, but also hetero atoms such as oxygen, sulfur, nitrogen, phosphorus and boron atoms in the ring, among organic compounds having a cyclic structure. The trivalent heterocyclic group is preferably a trivalent aromatic heterocyclic group.

Examples of the trivalent heterocyclic group include the followings.

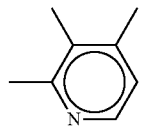
(201)

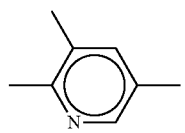
(202)

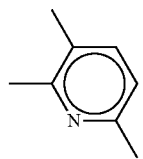
(203)

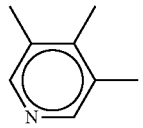
(204)

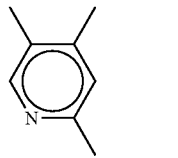
(205)

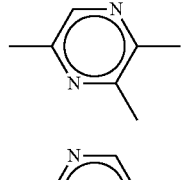
(206)

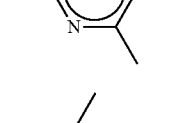
(207)

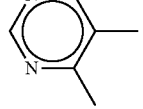
(208)

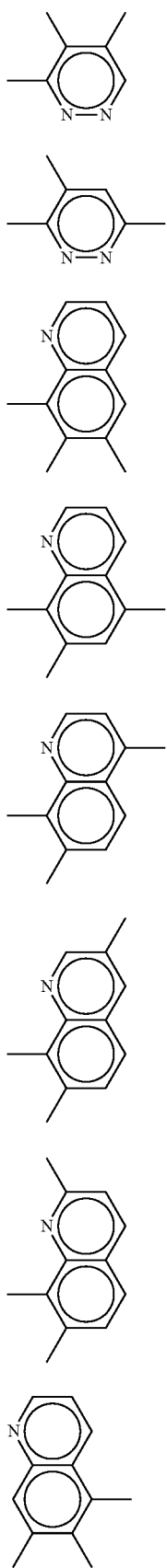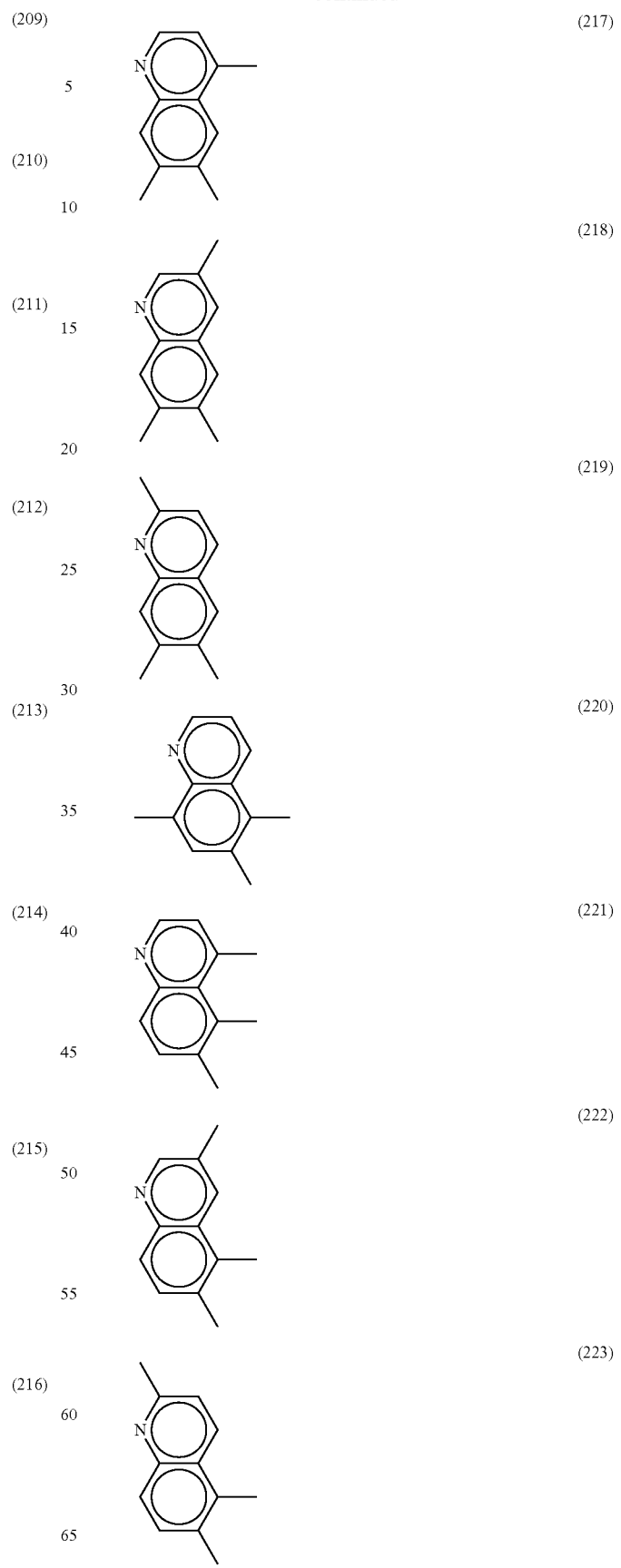

-continued
(224)
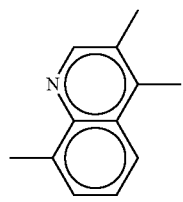
(225)
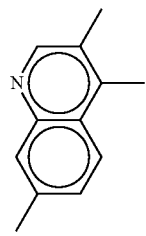
(226)
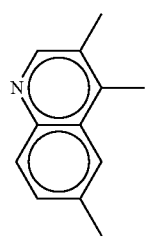
(227)
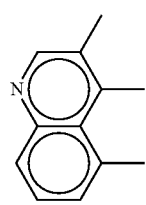
(228)
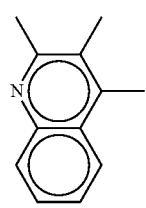
(229)
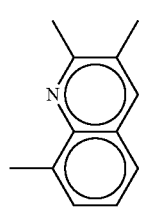
(230)
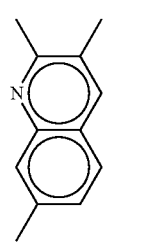
-continued
(231)
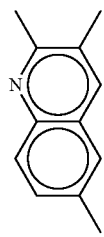
(232)
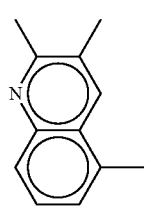
(233)
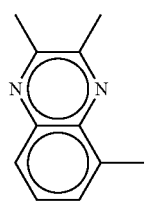
(234)
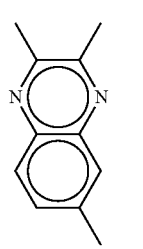
(235)
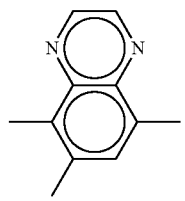
(236)
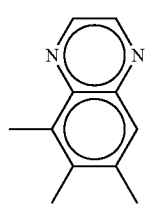
(237)

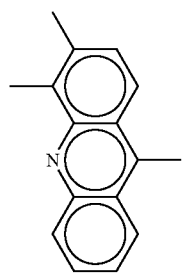
(238)
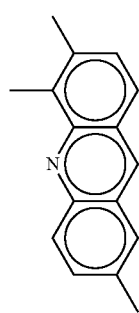
(239)
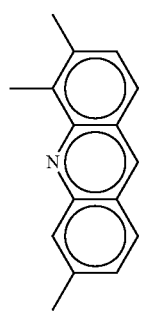
(240)
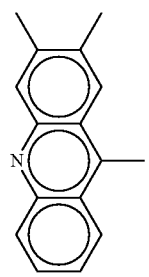
(241)
(242)
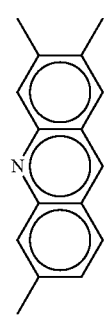
(243)
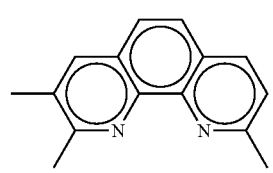
(244)
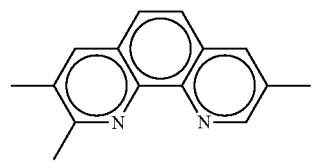
(245)
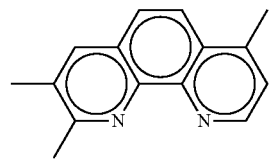
(246)
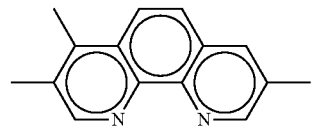
(247)
(248)
(249)
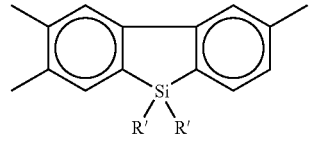
(250)
(251)

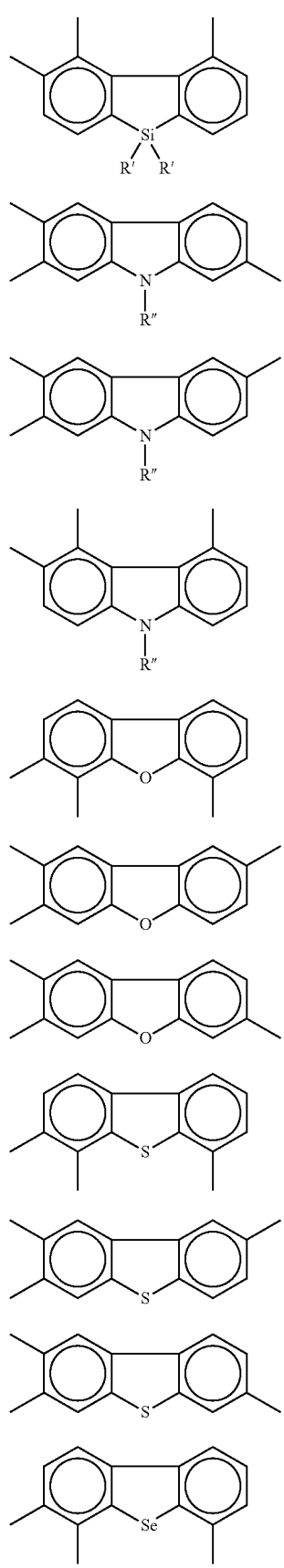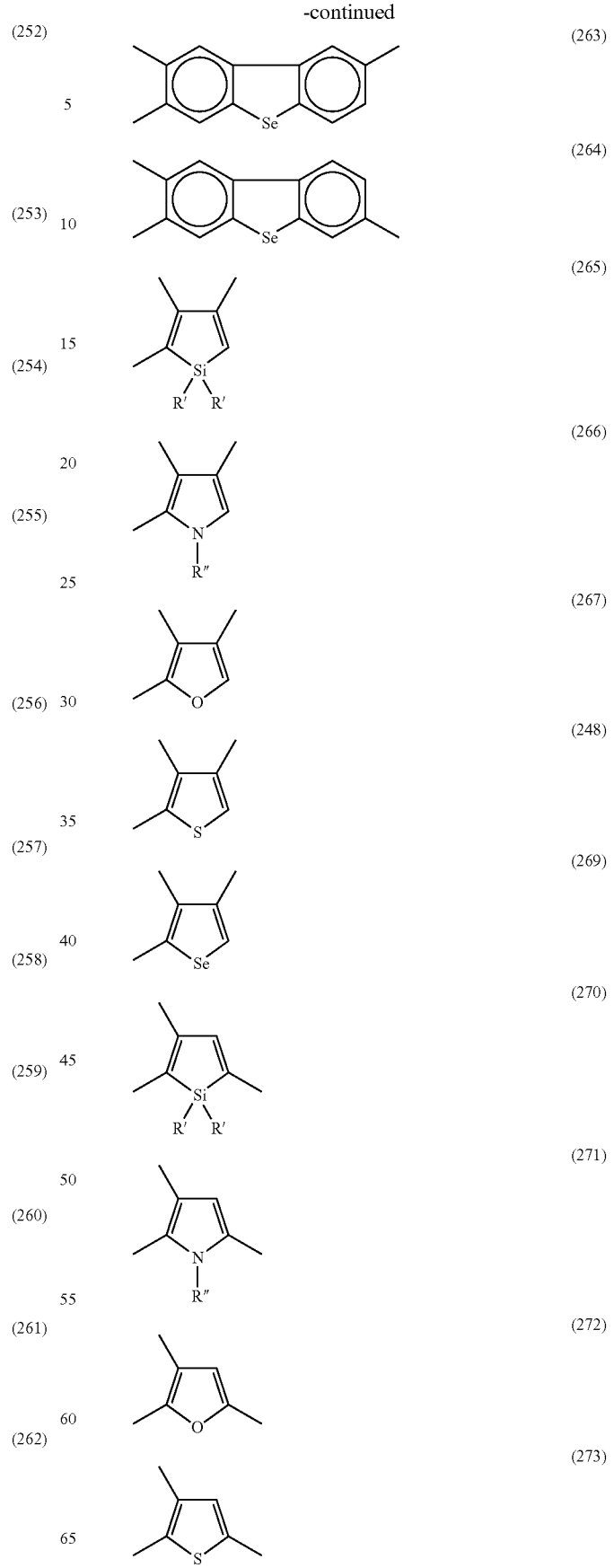

-continued

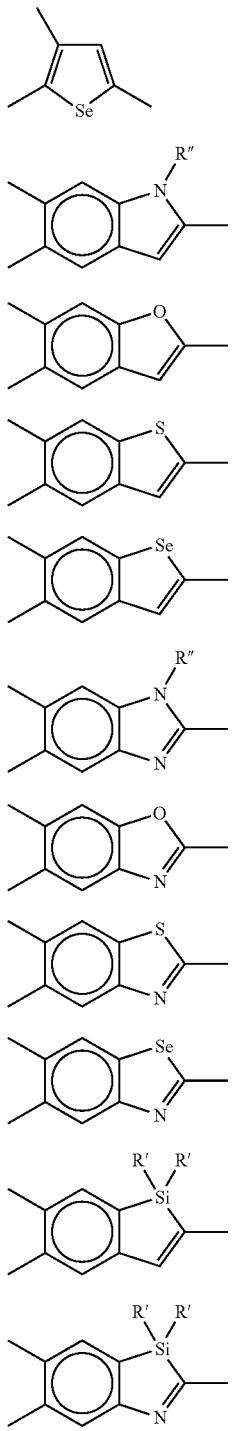

In formulas (201) to (284), when R's are the same or different and represent a hydrogen atom or a substituent. When R' is a substituent, examples of the substituent include an alkyl group, an alkoxy group, an alkylthio group, an aryl group, an aryloxy group, an arylalkyl group, an arylalkoxy group, an arylalkylthio group, a substituted amino group, an acyloxy group, an amido group, an arylalkenyl group, an arylalkynyl group, an monovalent heterocyclic group and a cyano group. The number of carbon atoms of the substituent is preferably from 1 to 18. R' is preferably a hydrogen atom or a substituent having 1 to 12 carbon atoms, and more preferably a hydrogen atom or a substituent having 1 to 8 carbon atoms.

R" are the same or different and represent a hydrogen atom, an alkyl group, an aryl group, an arylalkyl group, a substituted silyl group, an acyl group or a monovalent heterocyclic group.

Herein, an alkyl group may be a straight-chain or branched, or may be a cycloalkyl group. The alkyl group usually has 1 to 30 carbon atoms. Specific examples of the alkyl group include chain alkyl groups such as a methyl group, an ethyl group, an n-propyl group, an isopropyl group, an n-butyl group, an isobutyl group, a sec-butyl group, a tert-butyl group, an n-pentyl group, an isopentyl group, a 2-methylbutyl group, a 1-methylbutyl group, an n-hexyl group, an isohexyl group, a 3-methylpentyl group, a 2-methylpentyl group, a 1-methylpentyl group, a heptyl group, an octyl group, an isooctyl group, a 2-ethylhexyl group, a nonyl group, a decyl group, a undecyl group, a dodecyl group, a tetradecyl group, a hexadecyl group, an octadecyl group and an eicosyl group; and cycloalkyl groups such as a cyclopentyl group, a cyclohexyl group and an adamantyl group.

The alkoxy group may be straight-chain or branched, or may be a cycloalkoxy group. The alkoxy group my have a substituent. The alkoxy group usually has 1 to 20 carbon atoms, and specific examples of the alkoxy group which may have a substituent include a methoxy group, an ethoxy group, a propoxy group, an isopropoxy group, a butoxy group, an isobutoxy group, a tert-butoxy group, a pentyloxy group, a hexyloxy group, a cyclohexyloxy group, a heptyloxy group, an octyloxy group, a 2-ethylhexyloxy group, a nonyloxy group, a decyloxy group, a 3,7-dimethyloctyloxy group, a lauroyloxy group, a trifluoromethoxy group, a pentafluoroethoxy group, a perfluorobutoxy group, a perfluorohexyl group, a perfluorooctyl group, a methoxymethyloxy group and a 2-methoxymethyloxy group.

The alkylthio group may be straight-chain or branched, or may be a cycloalkylthio group. The alkylthio group may have a substituent. The alkylthio group usually has 1 to 20 carbon atoms, and specific examples of the alkylthio group which may have a substituent include a methylthio group, an ethylthio group, a propylthio group, an isopropylthio group, a butylthio group, an isobutylthio group, a tert-butylthio group, a pentylthio group, a hexylthio group, a cyclohexylthio group, a heptylthio group, an octylthio group, a 2-ethylhexylthio group, a nonylthio group, a decylthio group, a 3,7-dimethyloctylthio group, a laurylthio group and a trifluoromethylthio group.

The aryl group usually has 6 to 60 carbon atoms, and may have a substituent. Specific examples of the aryl group which may have a substituent include a phenyl group, a C1-C12 alkoxyphenyl group (C1-C12 shows that the number of carbon atoms is from 1 to 12, hereinafter the same shall apply), a C1-C12 alkylphenyl group, a 1-naphthyl group, a 2-naphthyl group, a pentafluorophenyl group.

The aryloxy group usually has 6 to 60 carbon atoms, and carbon atoms included in the aromatic ring may have a substituent. Specific examples of the aryloxy group which may have a substituent include a phenoxy group, a C1-C12 alkoxyphenoxy group, a C1-C12 alkylphenoxy group, a 1-naphthyloxy group, a 2-naphthyloxy group and a pentafluorophenyloxy group.

The arylalkyl group usually has 7 to 60 carbon atoms, and may have a substituent. Specific examples of the arylalkyl group which may have a substituent include a phenyl-C1-C2 alkyl group, a C1-C12 alkoxyphenyl-C1-C2 alkyl group, a C1-C12 alkylphenyl-C1-C2 alkyl group, a 1-naphthyl-C1-C12 alkyl group, and a 2-naphthyl-C1-C2 alkyl group.

The arylalkoxy group usually has 7 to 60 carbon atoms, and may have a substituent. Specific examples of the arylalkoxy group which may have a substituent include a phenyl-C1-C12 alkoxy group, a C1-C12 alkoxyphenyl-C1-C12 alkoxy group, a C1-C12 alkylphenyl-C1-C12 alkoxy group, a 1-naphthyl-C1-C12 alkoxy group and a 2-naphthyl-C1-C12 alkoxy group.

The arylalkylthio group usually has 7 to 60 carbon atoms, and may have a substituent. Specific examples of the arylalkylthio group which may have a substituent include a phenyl-C1-C12 alkylthio group, a C1-C12 alkoxyphenyl-C1-C12 alkylthio group, a C1-C12 alkylphenyl-C1-C12 alkylthio group, a 1-naphthyl-C1-C12 alkylthio group and a 2-naphthyl-C1-C12 alkylthio group.

The substituted amino group usually has 1 to 40 carbon atoms. Specific examples of the substituted amino group include a methylamino group, a dimethylamino group, an ethylamino group, a diethylamino group, a propylamino group, a dipropylamino group, an isopropylamino group, a diisopropylamino group, a butylamino group, an isobutylamino group, a tert-butylamino group, a pentylamino group, a hexylamino group, a cyclohexylamino group, a heptylamino group, an octylamino group, a 2-ethylhexylamino group, a nonylamino group, a decylamino group, a 3,7-dimethyloctylamine group, a laurylamine group, a cyclopentylamino group, a dicyclopentylamino group, a cyclohexylamino group, a dicyclohexylamino group, a pyrrolidyl group, a piperidyl group, ditrifluoromethylamino group, a phenylamino group, a diphenylamino group, a C1-C12 alkoxyphenylamino group, a di(C1-C12 alkoxyphenyl)amino group, a di(C1-C12 alkylphenyl)amino group, a 1-naphthylamino group, a 2-naphthylamino group, a pentafluorophenylamino group, a pyridylamino group, a pyridazinylamino group, a pyrimidylamino group, a pyrazylamino group, a triazylamino group, a phenyl-C1-C12 alkylamino group, a C1-C12 alkoxyphenyl-C1-C12 alkylamino group, a C1-C12 alkylphenyl-C1-C12 alkylamino group, a di(C1-C12 alkoxyphenyl-C1-C12 alkyl)amino group, a di(C1-C12 alkylphenyl-C1-C12 alkyl)amino group, a 1-naphthyl-C1-C12 alkylamino group and a 2-naphthyl-C1-C12 alkylamino group.

The acyloxy group usually has 2 to 20 carbon atoms. Specific examples of the acyloxy group include an acetoxy group, a propionyloxy group, a butyryloxy group, an isobutyryloxy group, a pivaloyloxy group, a benzoyloxy group, a trifluoroacetyloxy group and a pentafluorobenzoyloxy group.

The amido group usually has 2 to 20 carbon atoms. Specific examples of the amido group include a formamido group, an acetamido group, a propionamido group, a butyroamido group, a benzamido group, a trifluoroacetamido group, a pentafluorobenzamido group, a diformamido group, a diacetamido group, a dipropionamido group, a dibutyroamido group, a dibenzamido group, a ditrifluoroacetamido group and a dipentafluorobenzamido group.

The arylalkenyl group usually has 8 to 20 carbon atoms, and specific examples of the arylalkenyl group include a styryl group.

The arylalkynyl group usually has 8 to 20 carbon atoms, and specific examples of the arylalkynyl group include a phenylacetylenyl group.

Examples of the substituted silyl group include a trimethylsilyl group, a triethylsilyl group, a tri-n-propylsilyl group, a tri-isopropylsilyl group, a tert-butyldimethylsilyl group, a triphenylsilyl group, a tri-p-xylylsilyl group, a tribenzylsilyl group, a diphenylmethylsilyl group, a tert-butyldiphenylsilyl group, a dimethylphenylsilyl group and the like.

The acyl group usually has 2 to 20 carbon atoms. Specific examples of the acyl group include an acetyl group, a propionyl group, a butyryl group, an isobutyryl group, a pivaloyl group, a benzoyl group, a trifluoroacetyl group and a pentafluorobenzoyl group.

Examples of the monovalent heterocyclic group include groups in which one hydrogen atom has been removed from a heterocyclic compound, such as furan, thiophene, pyrrole, pyrroline, pyrrolidine, oxazole, isoxazole, thiazole, isothiazole, imidazole, imidazoline, imidazolidine, pyrazole, pyrazoline, pyrazolidine, furazan, triazole, thiadiazole, oxadiazole, tetrazole, pyran, pyridine, piperidine, thiopyran, pyridazine, pyrimidine, pyrazine, piperazine, morpholine, triazine, benzofuran, isobenzofuran, benzothiophene, indole, isoindole, indolizine, indoline, isoindoline, chromene, chroman, isochroman, benzopyran, quinoline, isoquinoline, quinolizidine, benzoimidazole, benzothiazole, indazole, naphthyridine, quinoxaline, quinazoline, quinazolidine, cinnoline, phthalazine, purine, pteridine, carbazole, xanthene, phenanthridine, acridine, β-carboline, pyrimidine, phenanthroline, thianthrene, phenoxathiin, phenoxazine, phenothiazine and phenazine. The monovalent heterocyclic group is preferably a monovalent aromatic heterocyclic group.

From the viewpoint of a short-circuit current density of a photoelectric conversion device, the trivalent heterocyclic group is preferably each of groups represented by formulas (265) to (284), and more preferably each of groups represented by formulas (265) to (274).

The divalent group represented by Z is preferably each of groups represented by formulas (Z-1) to (Z-5).

(Z-1)

(Z-2)

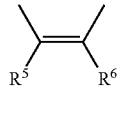

(Z-3)

(Z-4)

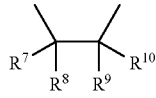

(Z-5)

In formulas (Z-1) to (Z-5), $R^1$ to $R^{10}$ are the same or different and represent a hydrogen atom or a substituent. When $R^1$ to $R^{10}$ are substituents, examples thereof include an alkyl group, an alkoxy group, an alkylthio group, an aryl group, an aryloxy group, an arylthio group, an arylalkyl group, an arylalkoxy group, an arylalkylthio group, an acyl group and an acyloxy group. The substituent is preferably an alkyl group having 6 to 18 carbon atoms, an alkoxy group having 6 to 18 carbon atoms, an aryl group or an aryloxy group, and more preferably an alkyl group having 6 to 18 carbon atoms.

Definition and specific examples of the alkyl group, alkoxy group, alkylthio group, aryl group, aryloxy group, arylthio group, arylalkyl group, arylalkoxy group, arylalkylthio group, acyl group and acyloxy group are the same as those of the alkyl group, alkoxy group, alkylthio group, aryl group, aryloxy group, arylthio group, arylalkyl group, arylalkoxy group, arylalkylthio group, acyl group and acyloxy group which are represented by the above-mentioned R' or R".

From the viewpoint of short-circuit current density of an photoelectric conversion device, the divalent group represented by Z is preferably each of groups represented by formulas (Z-1) to (Z-3) and (Z-5), more preferably each of groups represented by formulas (Z-1) to (Z-3), still more preferably each of groups represented by formulas (Z-1) to (Z-2), and particularly preferably a group represented by formula (Z-1).

From the viewpoint of a short-circuit current density of a photoelectric conversion device, the structural unit represented by formula (I) is preferably a structural unit represented by formula (IV):

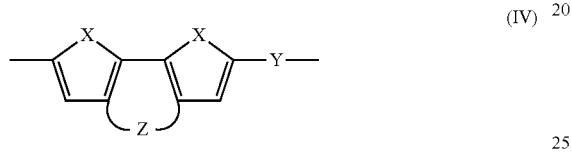

(IV)

wherein X represents a sulfur atom, an oxygen atom, a selenium atom, —NH— or —N($R^a$)—; $R^a$ represents a substituent; and Z has the same meaning as defined above.

The substituent represented by $R^a$ is preferably a group having 1 to 30 carbon atoms. Examples of the substituent include alkyl groups such as a methyl group, an ethyl group, a butyl group, a hexyl group, an octyl group and a dodecyl group; alkoxy groups such as a methoxy group, an ethoxy group, a butoxy group, a hexyloxy group, an octyloxy group and a dodecyloxy group; and aryl groups such as a phenyl group and a naphthyl group.

The structural unit represented by formula (IV) is composed of a moiety represented by formula (IV-1) and a moiety represented by formula (IV-2):

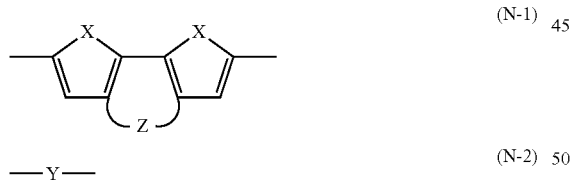

(N-1)

(N-2)

wherein X, Y and Z in formulas (IV-1) and (IV-2) have the same meanings as defined above, and two Xs may be the same or different.

A moiety represented by formula (IV-1) is preferably each of moieties represented by formulas (301) to (325).

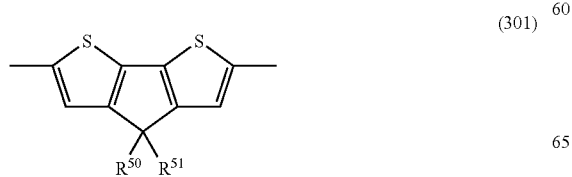

(301)

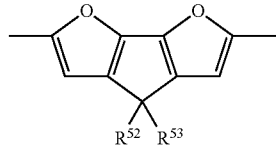

(302)

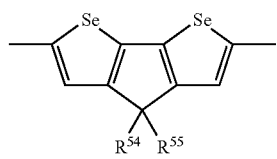

(303)

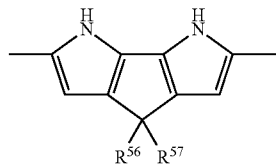

(304)

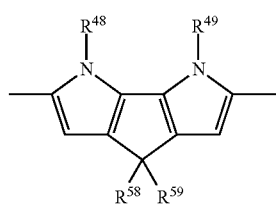

(305)

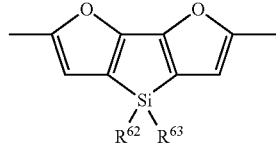

(306)

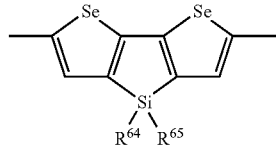

(307)

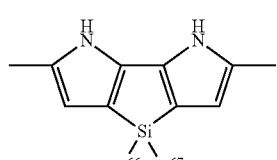

(308)

(309)

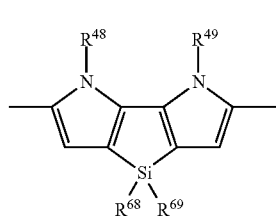

(310)

(311) 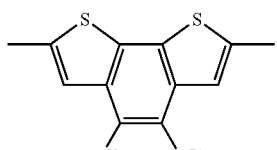

(312) 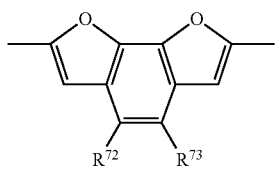

(313) 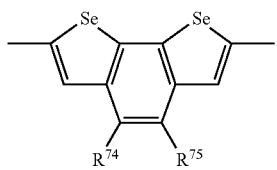

(314) 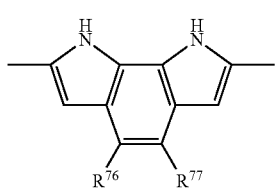

(315) 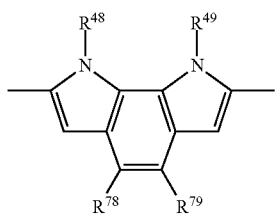

(316) 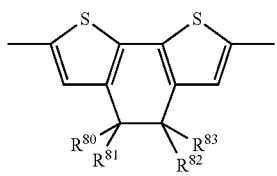

(317) 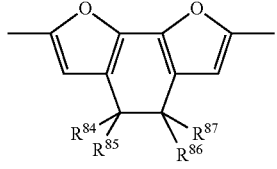

(318) 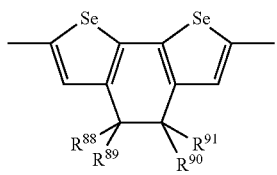

(319) 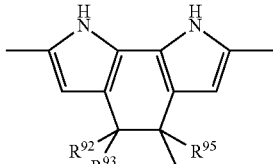

(320) 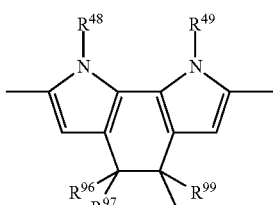

(321) 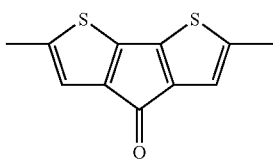

(322) 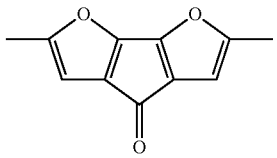

(323) 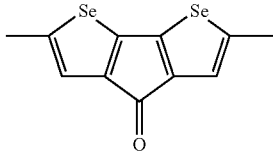

(324) 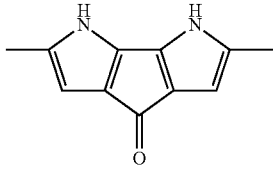

(325) 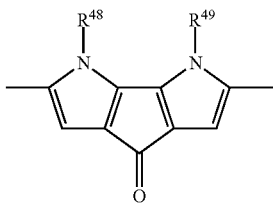

In the formulas, $R^{48}$ and $R^{49}$ are the same or different and represent an alkyl group, and an alkyl group having 1 to 16 carbon atoms is preferable. Examples of the alkyl group include a methyl group, an ethyl group, a butyl group, a hexyl group, an octyl group and a dodecyl group. $R^{50}$ to $R^{99}$ are the same or different and represent a hydrogen atom or a substituent. Specific examples of the substituent are the same as those of the substituent represented by $R^1$ to $R^{10}$.

From the viewpoint of a short-circuit current density of a photoelectric conversion device, the moiety represented by formula (IV-1) is preferably a moiety represented by formula (301), (303), (306), (308), (311), (313), (316) or (318), more preferably a moiety represented by formula (301), (306), (311) or (316), still more preferably a moiety represented by formula (301) or (306), and particularly preferably a moiety represented by formula (301), among moieties represented by formulas (301) to (325).

In formula (IV-2), the divalent heterocyclic group represented by Y refers to an atomic group remaining after removing two hydrogen atoms from a heterocyclic compound, and the number of carbon atoms constituting the ring is usually from 2 to 60.

The divalent heterocyclic group represented by Y is preferably each of groups represented by formulas (Y-1) to (Y-5):

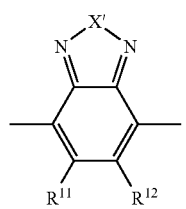
(Y-1)

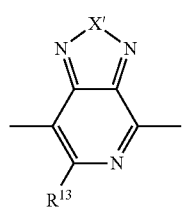
(Y-2)

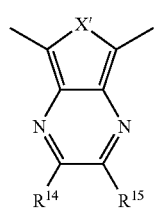
(Y-3)

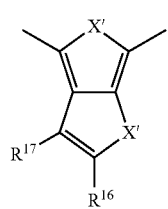
(Y-4)

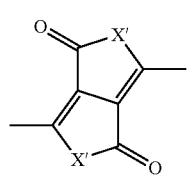
(Y-5)

wherein X' represents a sulfur atom, an oxygen atom, a selenium atom, —NH— or —N($R^a$)—; $R^a$ represents a substituent; $R^{11}$ to $R^{17}$ are the same or different and represent a hydrogen atom or a substituent; $R^{11}$ and $R^{12}$ may be connected to each other to form a cyclic structure; and when plural X's are present, they may be the same or different.

When $R^{11}$ to $R^{17}$ are substituents, examples of the substituent include an alkyl group, an alkoxy group, an alkylthio group, an aryl group, an aryloxy group, an arylalkyl group, an arylalkoxy group, an arylalkylthio group, a substituted amino group, an acyloxy group, an amido group, an arylalkenyl group, an arylalkynyl group, a monovalent heterocyclic group, a cyano group, a substituted silyl group, an acyl group and a halogen atom. Examples of the halogen atom include a fluorine atom, a chlorine atom, a bromine atom and an iodine atom. $R^{11}$ to $R^{16}$ preferably represent a hydrogen atom or a substituent having 1 to 18 carbon atoms, and more preferably a hydrogen atom or a substituent having 6 to 16 carbon atoms. $R^{17}$ is preferably a hydrogen atom or a fluorine atom and more preferably a fluorine atom. $R^{11}$ and $^{12}$ may be connected to each other to form a cyclic structure.

Definition and specific examples of the alkyl group, alkoxy group, alkylthio group, aryl group, aryloxy group, arylalkyl group, arylalkoxy group, arylalkylthio group, a substituted amino group, acyloxy group, amido group, arylalkenyl group, arylalkynyl group, a monovalent heterocyclic group, a cyano group, a substituted silyl group and acyl group are the same as those of the alkyl group, alkoxy group, alkylthio group, aryl group, aryloxy group, arylalkyl group, arylalkoxy group, arylalkylthio group, a substituted amino group, acyloxy group, amido group, arylalkenyl group, arylalkynyl group, a monovalent heterocyclic group, a substituted silyl group and acyl group which are represented by the above-mentioned R' or R".

In formulas (Y-1) to (Y-4), X' is preferably a sulfur atom. In formula (Y-5), X' is preferably —N($R^a$)—.

Specific examples of the cyclic structure formed by connection of $R^{11}$ with $R^{12}$ include a cyclic structure represented by formula (B-1) and cyclic structure represented by formula (B-2):

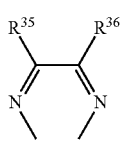
(B-1)

(B-2)

wherein X' in formulas (B-1) and (B-2) represents a sulfur atom, an oxygen atom, a selenium atom, —NH— or —N($R^a$)—, and preferably a sulfur atom; $R^{35}$ and $R^{36}$ are the same or different and represent a hydrogen atom or a substituent and, when $R^{35}$ and $R^{36}$ are substituents, the substituent is preferably an alkyl group, an alkoxy group, an aryl group, an aryloxy group, an arylalkyl group, an arylalkoxy group, a monovalent heterocyclic group, a cyano group or a halogen atom; definition and specific examples of the alkyl group, alkoxy group, aryl group, aryloxy group, arylalkyl group, arylalkoxy group, monovalent heterocyclic group and halogen atom are the same as those of alkyl group, alkoxy group, aryl group, aryloxy group, arylalkyl group, arylalkoxy group, monovalent heterocyclic group, halogen atom, which are represented by $R^{11}$, and the substituent preferably has 1 to 18 carbon atoms.

Examples of the groups represented by formulas (Y-1) to (Y-5) include groups represented by formulas (y-1) to (y-10).

(y-1)
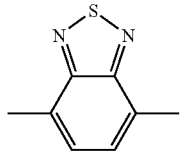

(y-2)
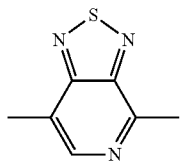

(y-3)
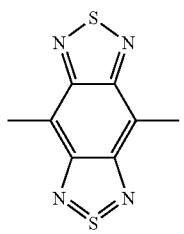

(y-4)
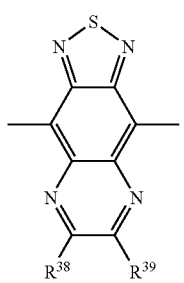

(y-5)
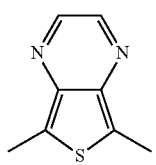

(y-6)
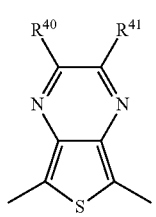

(y-7)
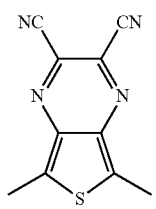

(y-8)
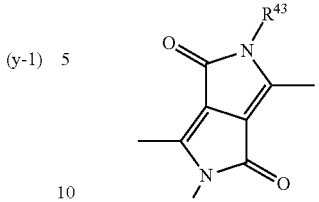

(y-9)
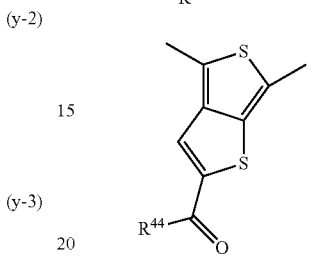

(y-10)
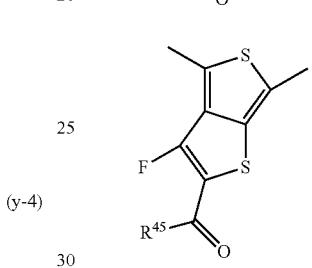

In formulas (y-1) to (y-10), $R^{38}$ to $R^{45}$ are the same or different and represent a hydrogen atom or a substituent. When $R^{38}$ to $R^{45}$ are substituents, examples of the substituent include alkyl groups such as a methyl group, an ethyl group, a butyl group, an hexyl group, an octyl group and an dodecyl group; alkoxy groups such as a methoxy group, an ethoxy group, a butoxy group, a hexyloxy group, an octyloxy group and a dodecyloxy group; and aryl groups such as a phenyl group and a naphthyl group. The substituent is preferably a substituent having 1 to 30 carbon atoms. Among groups represented by formulas (y-1) to (y-10), preferable groups are represented by formulas (y-1) to (y-3) and (y-8) to (y-10); more preferable groups are represented by formula (y-1), (y-2), (y-3), (y-8) and (y-10); still more preferable groups are represented by formulas (y-1) and (y-2); and particularly preferable group is represented by formula (y-1), from the viewpoint of a short-circuit current density of a photoelectric conversion device.

Preferred one aspect of the polymer compound of the present invention is a polymer compound containing a repeating unit represented by formula (I-A) and a repeating unit represented by formula (II-A). A polymer compound containing a repeating unit represented by formula (IV-A) and a repeating unit represented by formula (II-A) are more preferably:

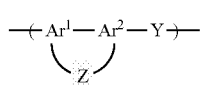
(I-A)

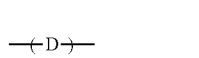
(II-A)

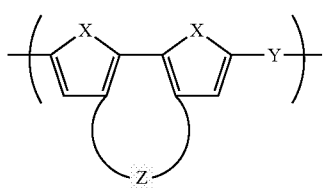
(IV-A)

wherein $Ar^1$, $Ar^2$, X, Y, Z and D in formulas (I-A), (II-A) and (IV-A) have the same meanings as defined above, and two Xs may be the same or different.

From the viewpoint of a short-circuit current density of a photoelectric conversion device, the polymer compound of the present invention containing a structural unit represented by formula (III) is preferred:

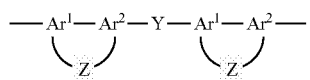
(III)

wherein $Ar^1$, $Ar^2$, Y and Z in formula (III) have the same meanings as defined above, two $Ar^1$s may be the same or different; two $Ar^2$s may be the same or different; and two Zs may be the same or different.

From the viewpoint of a short-circuit current density of a photoelectric conversion device, the structural unit represented by formula (III) is preferably the structural unit represented by formula (V):

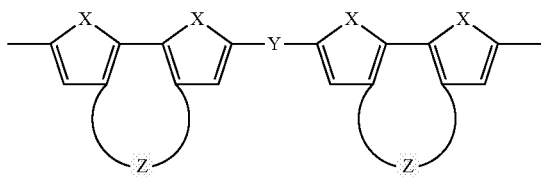
(V)

wherein X, Y and Z in formula (V) have the same meanings as defined above, and four Xs may be the same or different; and two Zs may be the same or different.

The structural unit represented by formula (V) is preferably each of structural units represented by formulas (501) to (600).

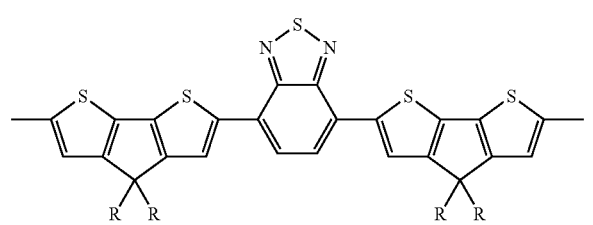
(501)

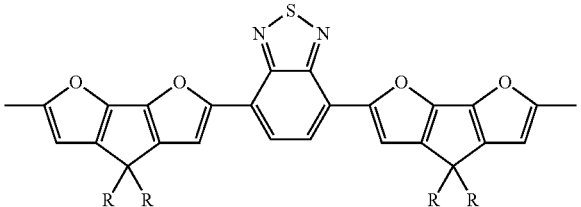
(502)

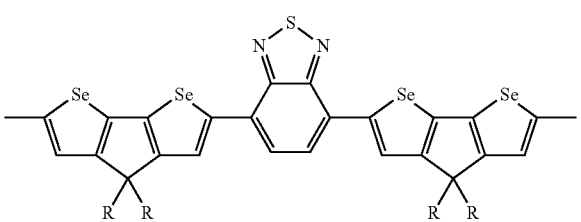
(503)

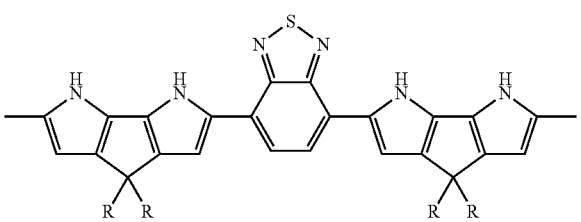
(504)

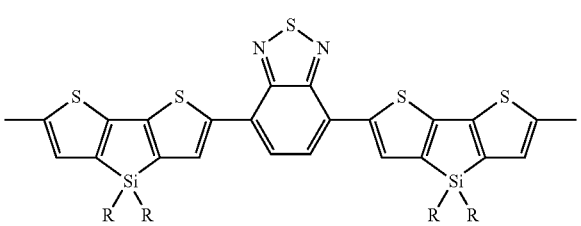
(505)

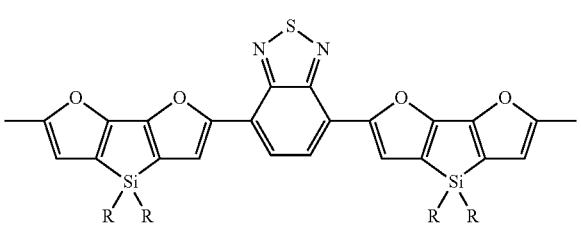
(506)

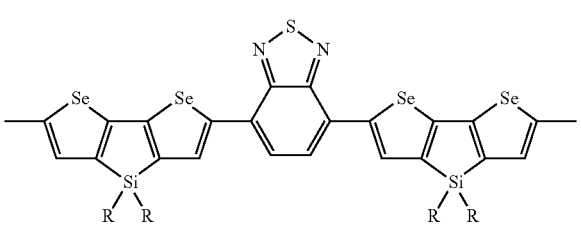
(507)

(508)
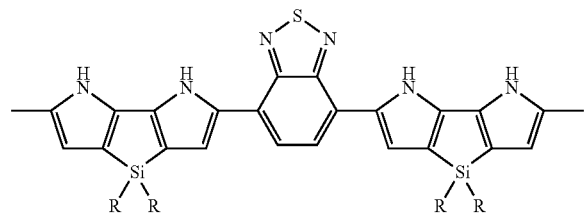
(509)
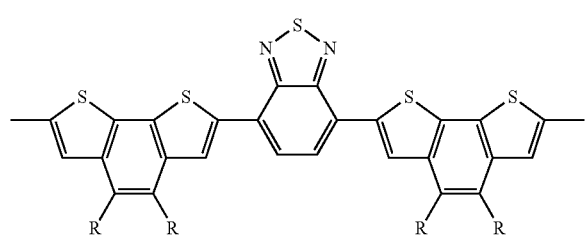
(510)
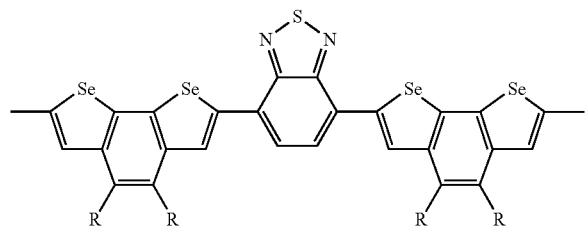
(511)
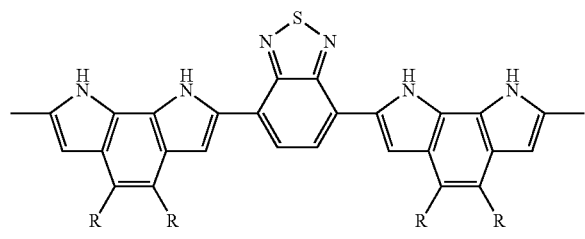
(512)
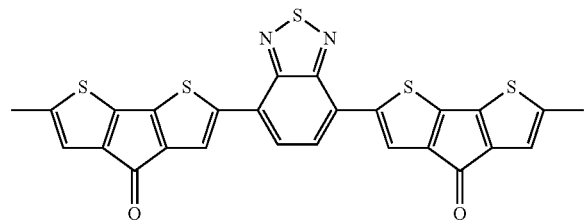
(513)
(514)
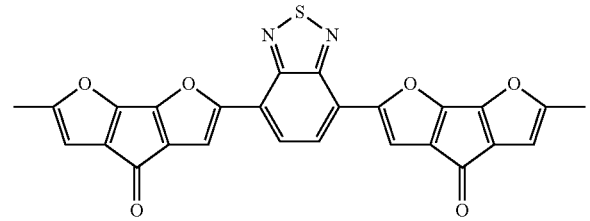
(515)
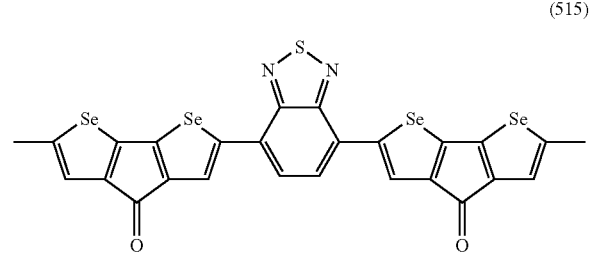
(516)
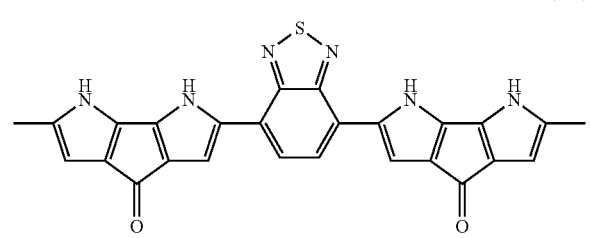
(517)
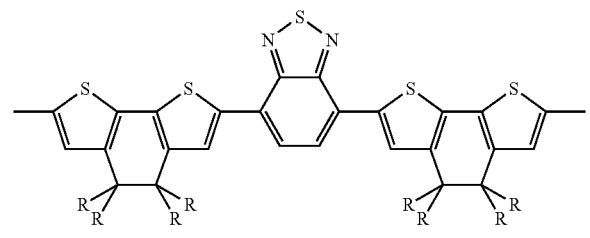
(518)
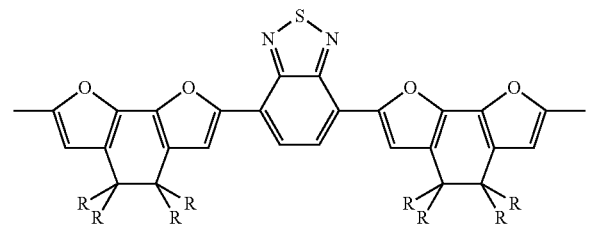
(519)
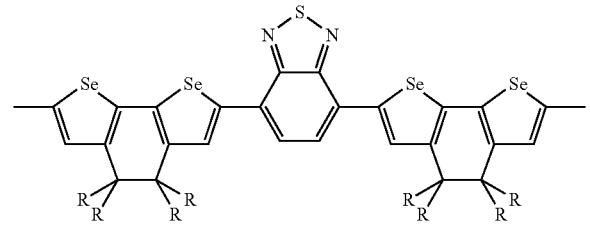

33
-continued
(520)
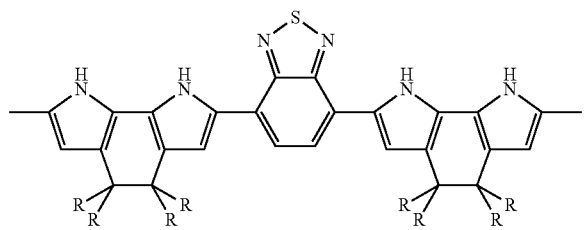
(521)
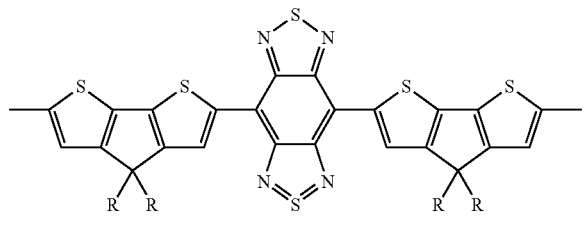
(522)
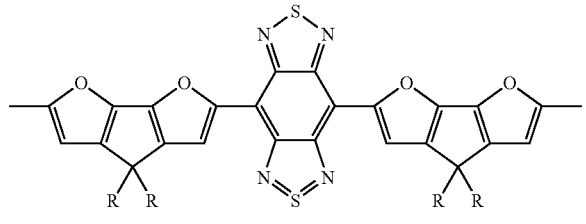
(523)
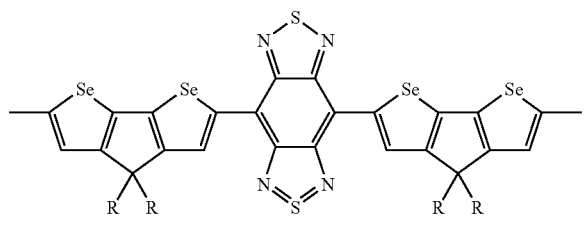
(524)
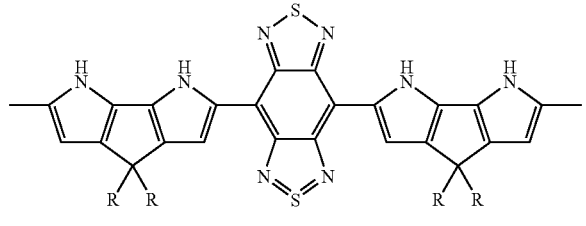
(525)
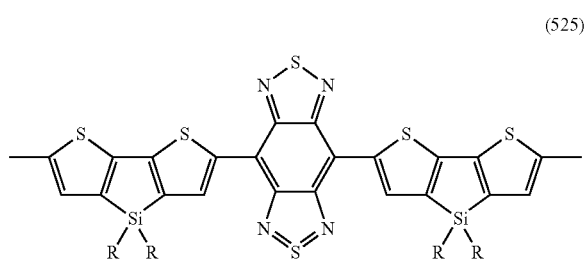
34
-continued
(526)
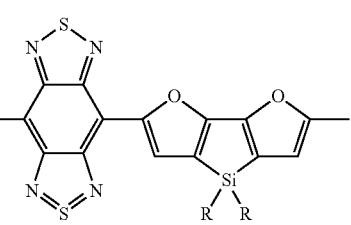
(527)
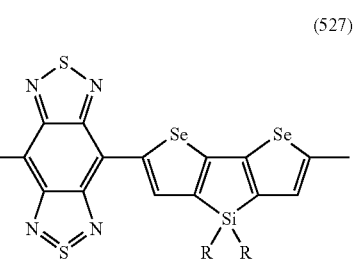
(528)
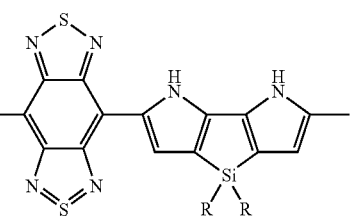
(529)
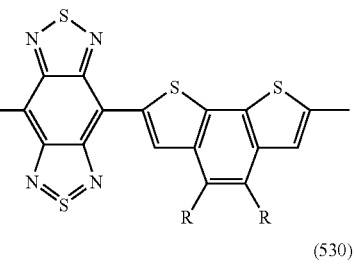
(530)
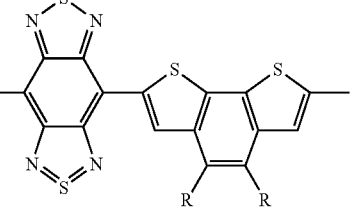
(531)
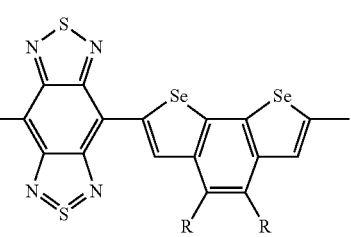

(532)
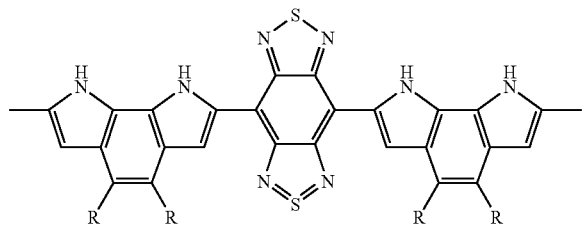
(533)
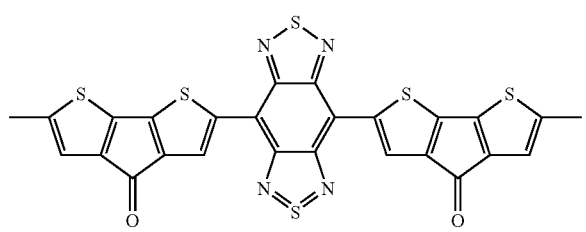
(534)
(535)
(536)
(537)
(538)
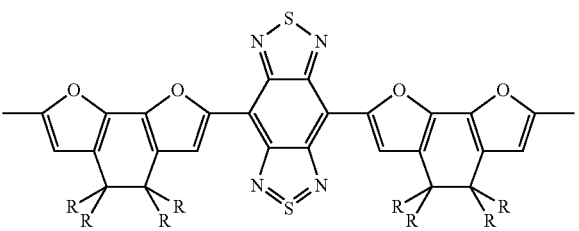
(539)
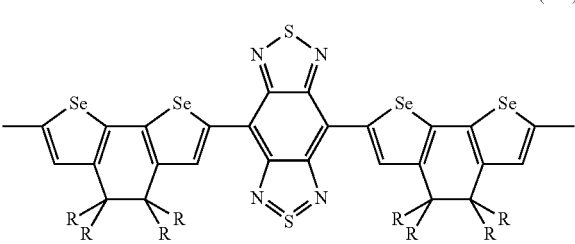
(540)
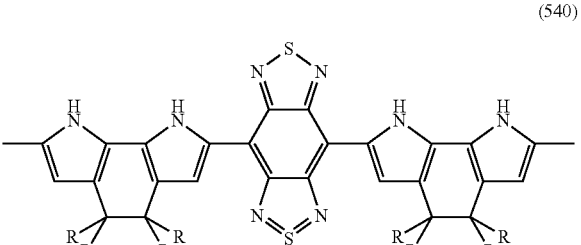
(541)
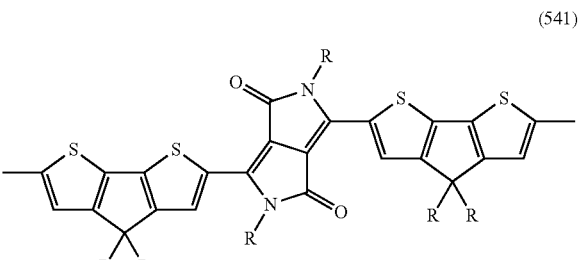
(542)
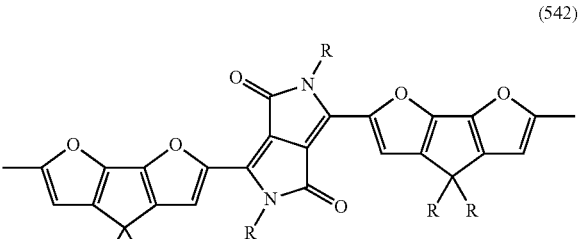
(543)
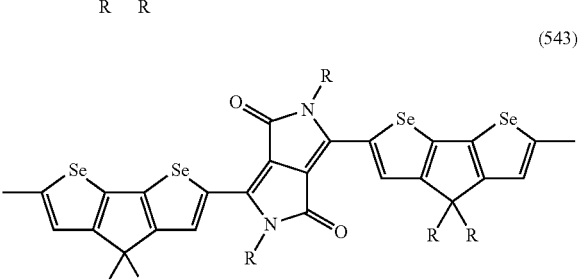

(544)
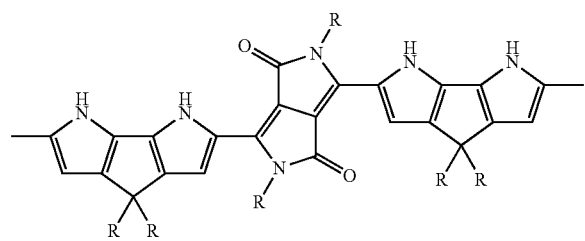
(545)
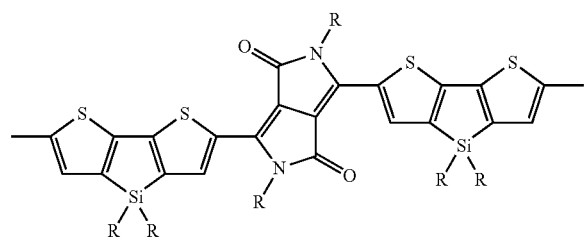
(546)
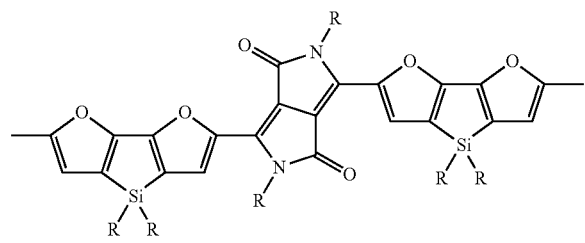
(547)
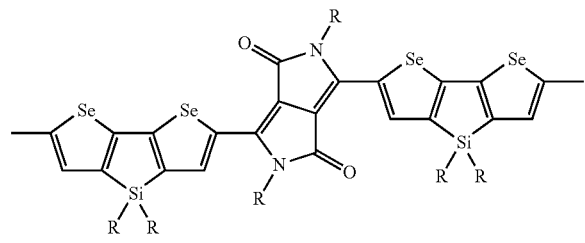
(548)
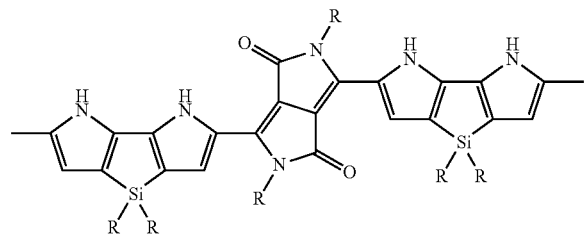
(549)
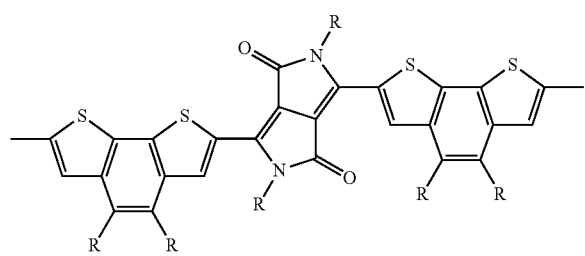
(550)
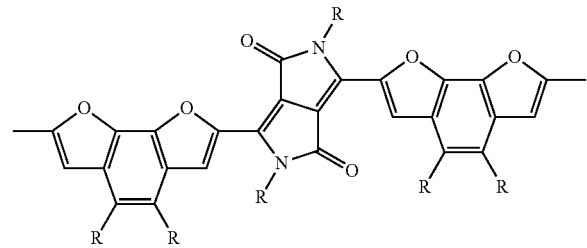
(551)
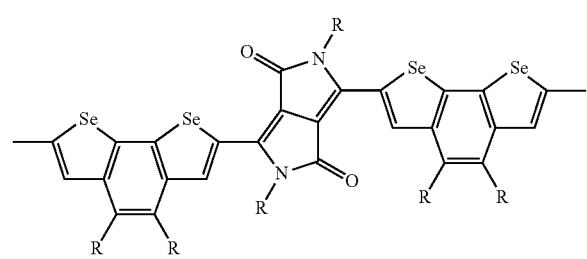
(552)
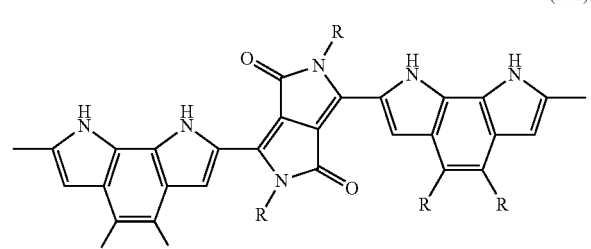
(553)
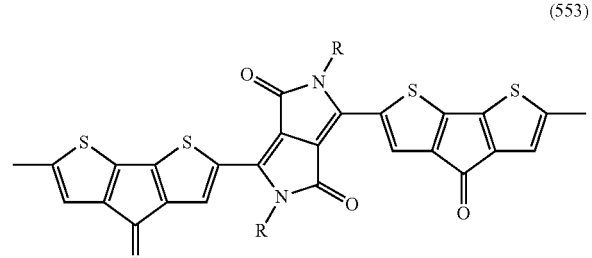
(554)
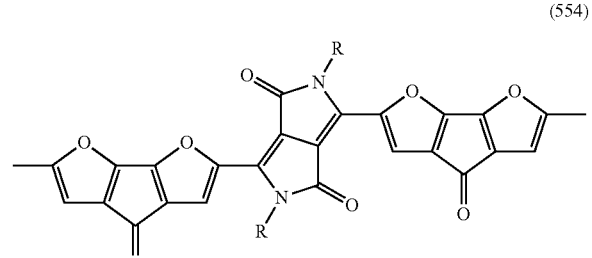
(555)
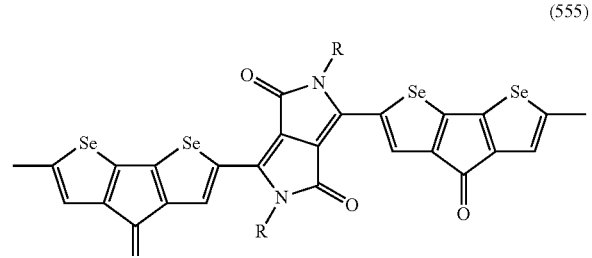

(556)
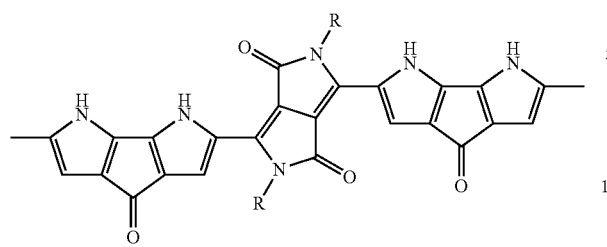
(557)
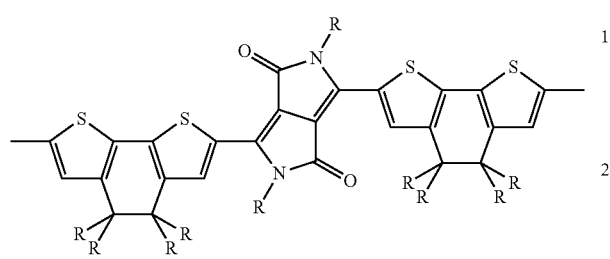
(558)
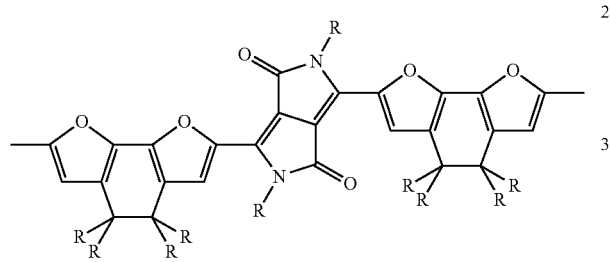
(559)
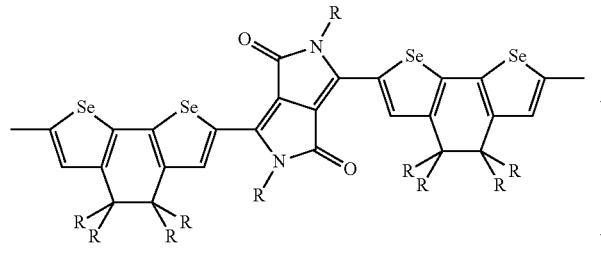
(560)
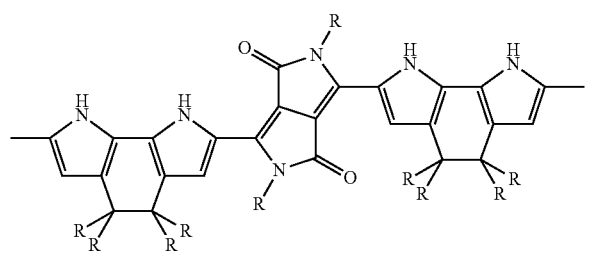
(561)
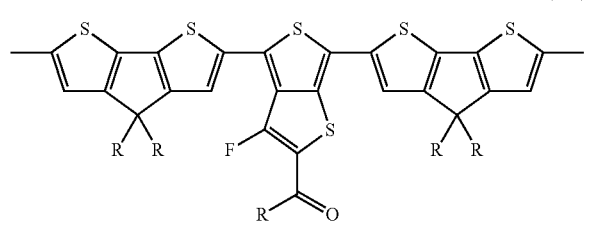
(562)
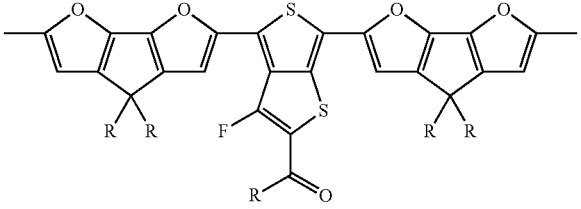
(563)
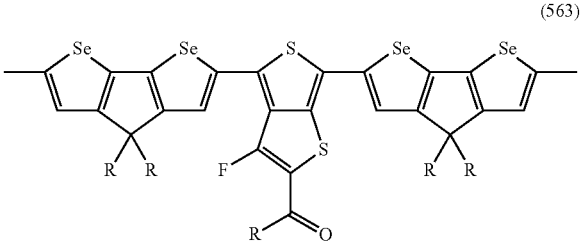
(564)
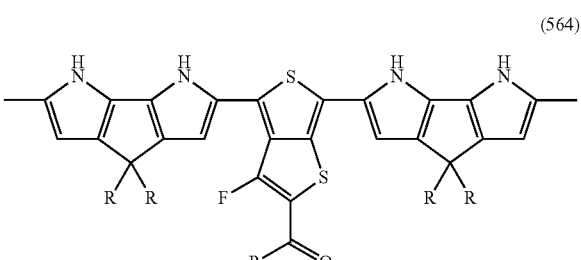
(565)
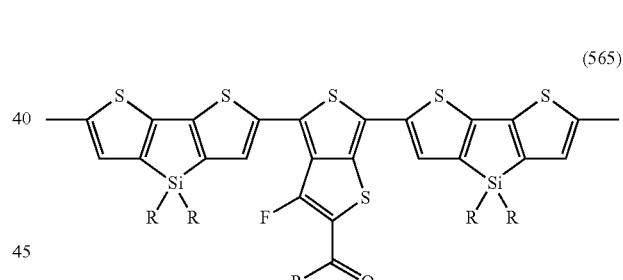
(566)
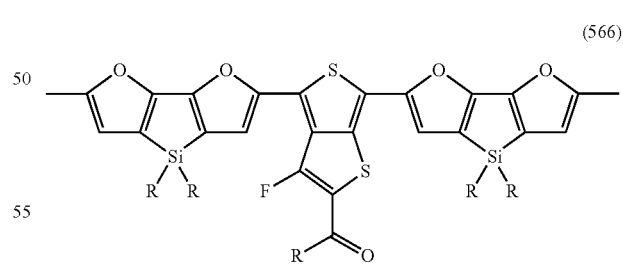
(567)
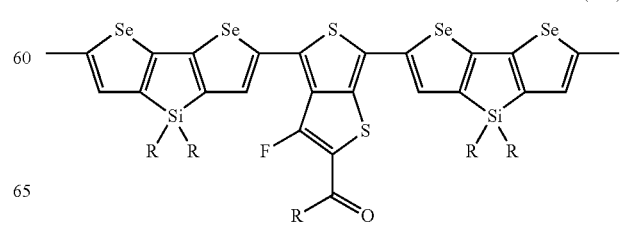

(568)
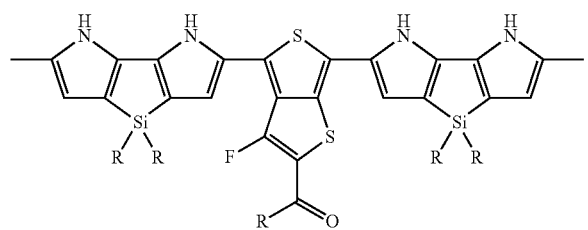
(574)
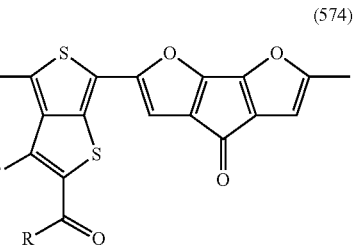
(569)
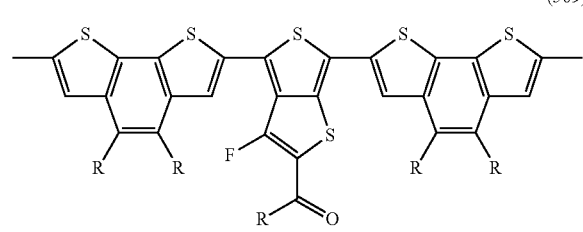
(575)
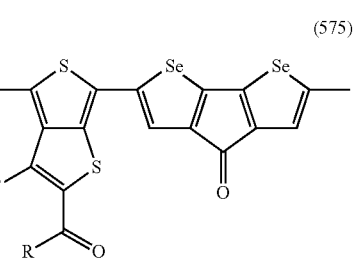
(570)
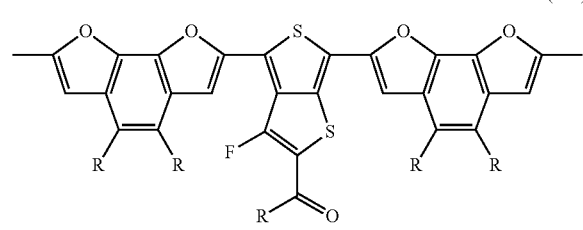
(576)
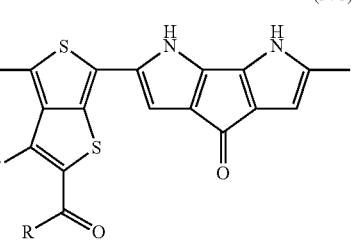
(571)
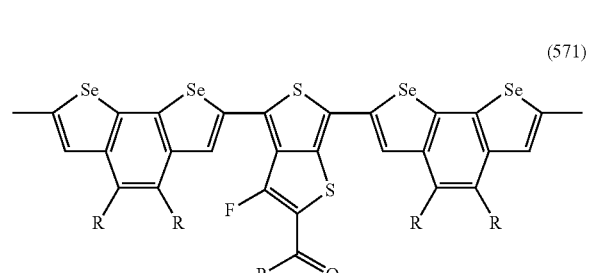
(577)
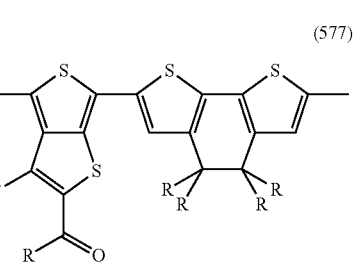
(572)
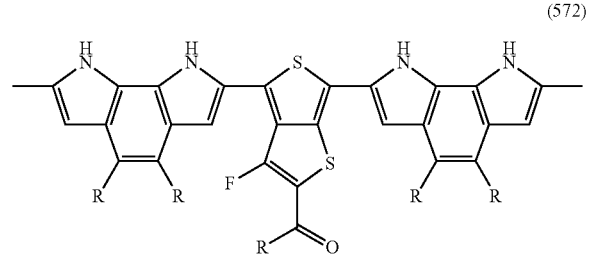
(578)
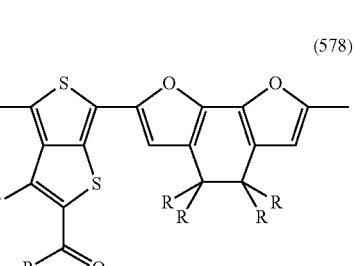
(573)
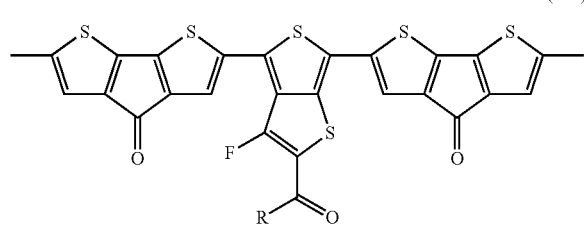
(579)
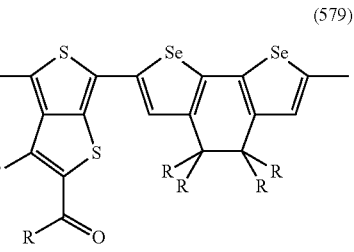

(580)
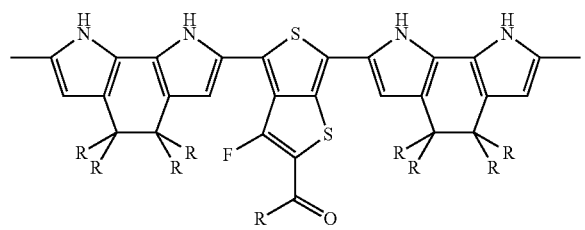
(581)
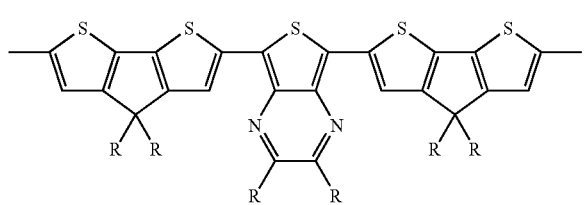
(582)
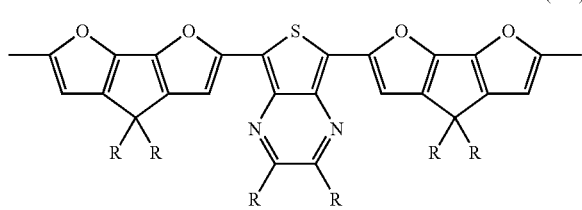
(583)
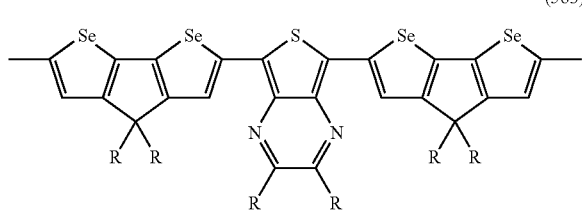
(584)
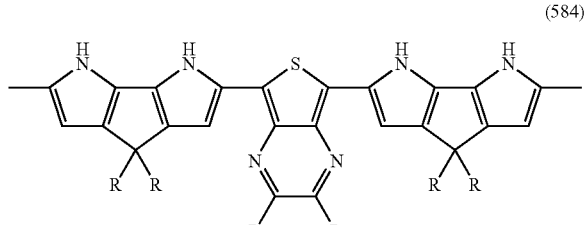
(585)
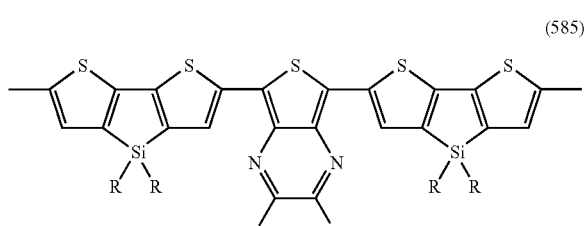
(586)
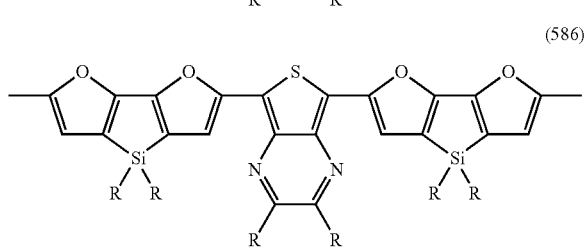
(587)
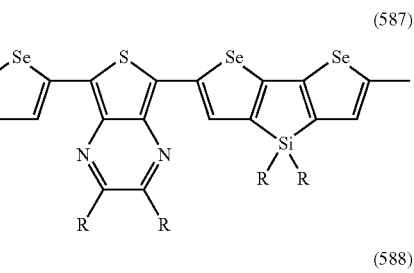
(588)
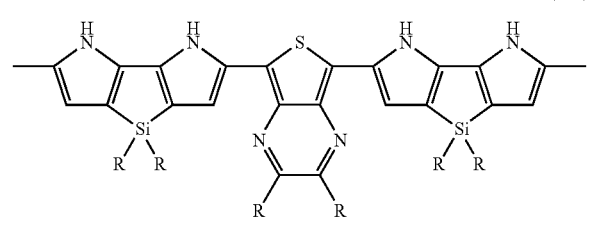
(589)
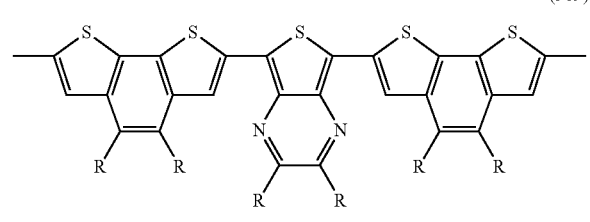
(590)
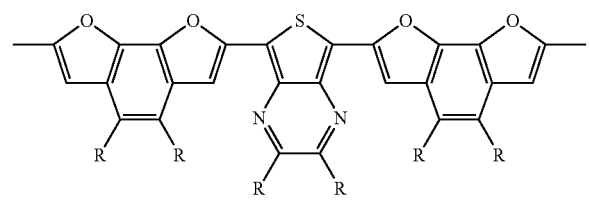
(591)
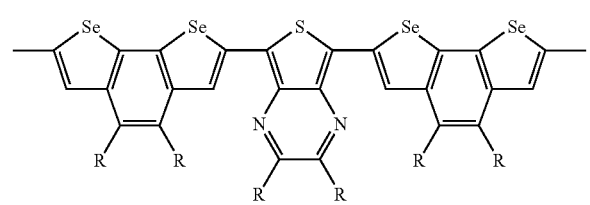
(592)
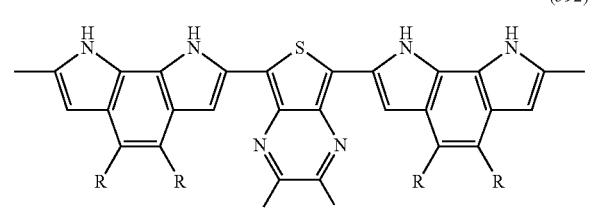
(593)
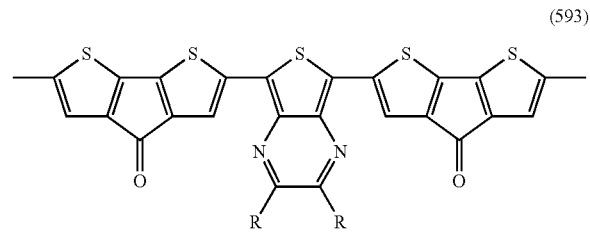

-continued (594)
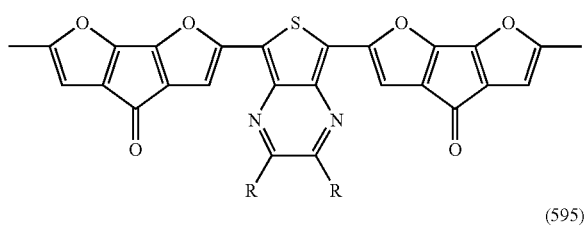

(595)
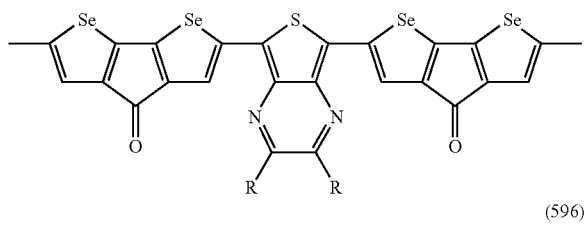

(596)
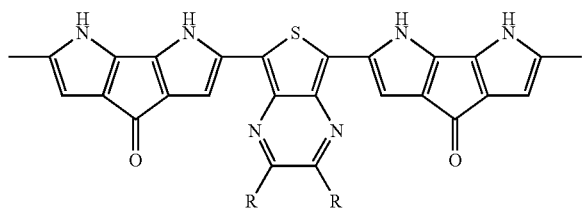

(597)
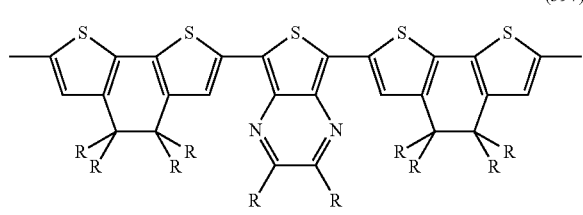

(598)
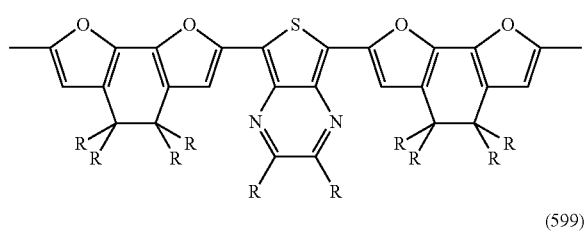

(599)
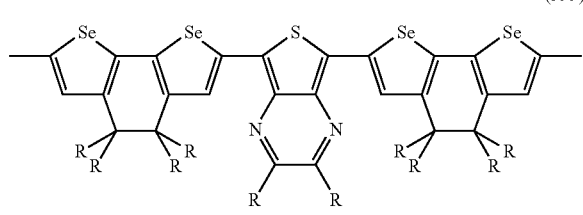

(600)
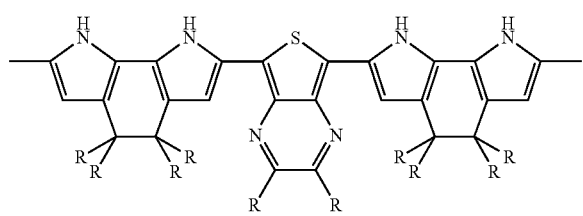

In formulas (501) to (600), R represents a hydrogen atom or a substituent. When plural Rs are present, they may be the same or different. When R is a substituent, examples thereof include alkyl groups such as a methyl group, an ethyl group, a butyl group, a hexyl group, an octyl group and an dodecyl group; alkoxy groups such as a methoxy group, an ethoxy group, a butoxy group, a hexyloxy group, an octyloxy group and a dodecyloxy group; aryl groups such as a phenyl group and an naphthyl group; and heteroaryl groups such as a thienyl group. When the substituent is an alkyl group or an alkoxy group, the substituent preferably has 1 to 20 carbon atoms, more preferably 1 to 16 carbon atoms, and particularly preferably 6 to 16 carbon atoms.

Among structural units represented by formulas (501) to (600), preferable structural units are represented by formulas (501), (503), (505), (507), (509), (511), (521), (523), (525), (527), (529), (531), (541), (543), (545), (547), (549), (551), (561), (563), (565), (567), (569), (571), (581), (583), (585), (587), (589) and (591); more preferable structural units are represented by formulas (501), (505), (509), (521), (525), (529), (541), (545), (549), (561), (565), (569), (581), (585) and (589); still more preferable structural units are represented by formulas (501), (505), (521), (525), (541), (545), (561), (565), (581) and (585); particularly preferable structural units are represented by formulas (501), (505), (521), (525), (541), (545), (581), and (585); and yet more preferable structural units are represented by formulas (501) (521) and (541), from the viewpoint of a short-circuit current density of a photoelectric conversion device.

Another preferred aspect of the polymer compound of the present invention is a polymer compound containing a repeating unit represented by formula (III-A) and a repeating unit represented by formula (II-A). A polymeric compound including a repeating unit represented by formula (V-A) and a repeating unit represented by formula (II-A) is more preferably:

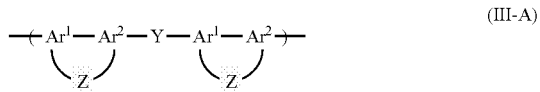
(III-A)

(II-A)

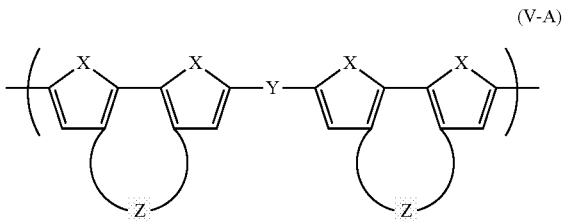
(V-A)

wherein $Ar_1$, $Ar_2$, X, Y and Z and D in formulas (III-1), (II-1) and (V-1) have the same meanings as defined above; two $Ar^1$s may be the same or different; two $Ar^2$s may be the same or different; four Xs may be the same or different; and two Zs may be the same or different.

The number of carbon atoms, which constitute an arylene group or a heteroarylene group having a fused ring represented by D, is usually from about 4 to 60.

Examples of the arylene group or heteroarylene group having a fused ring represented by D include groups represented by formulas 1 to 139:
1
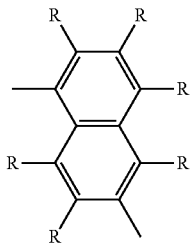
2
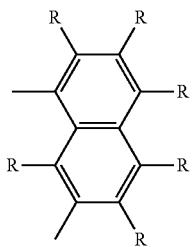
3
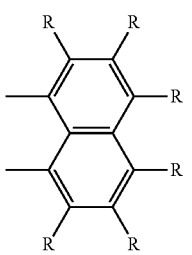
4
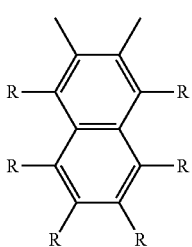
5
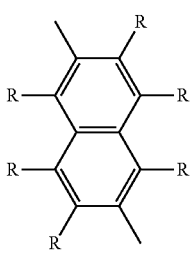
6
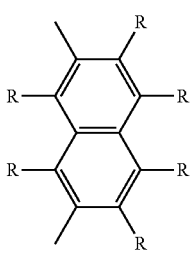
-continued
7
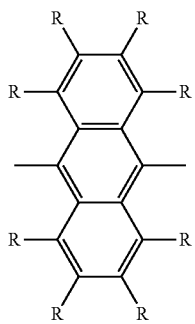
8
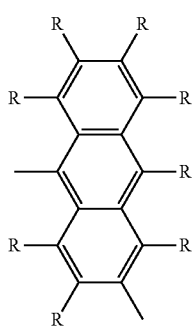
9
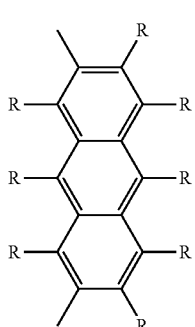
10
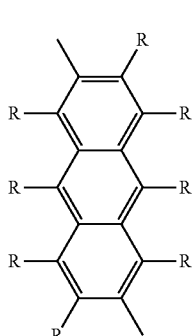
11
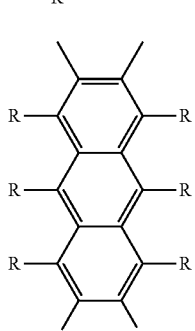

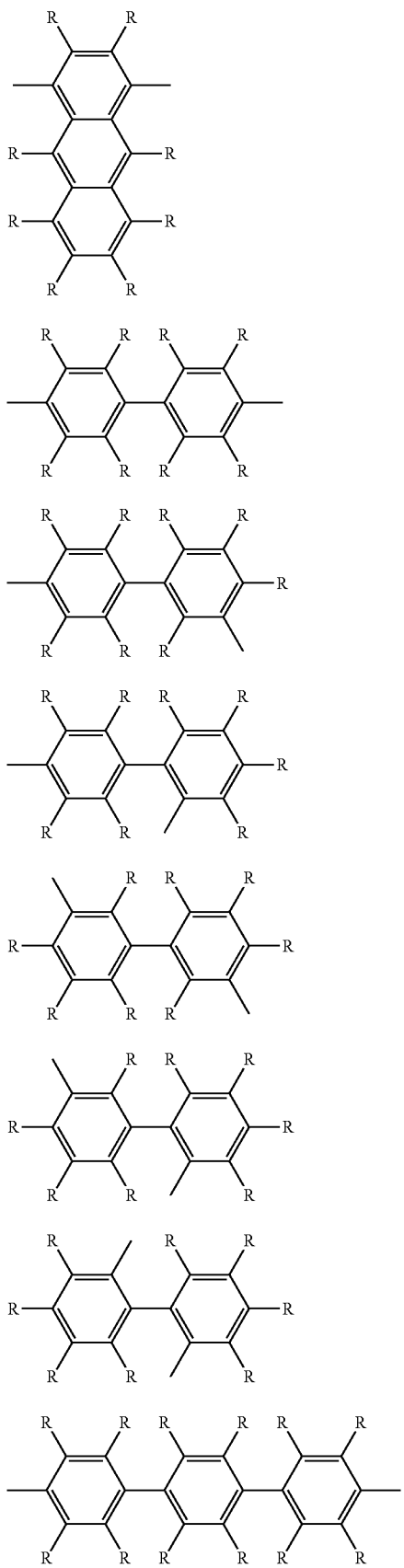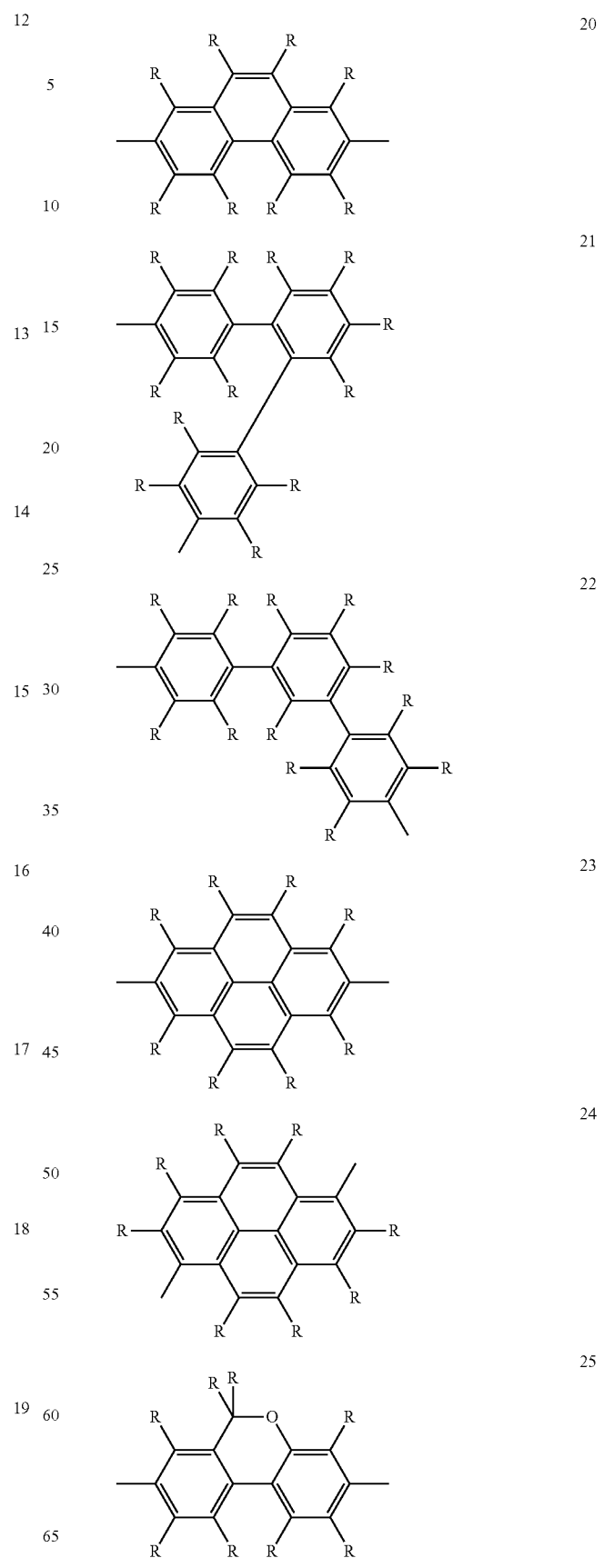

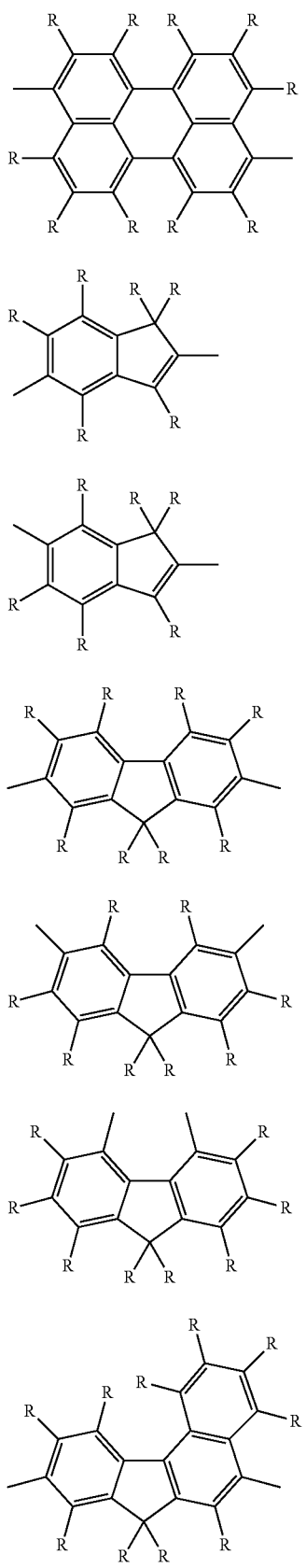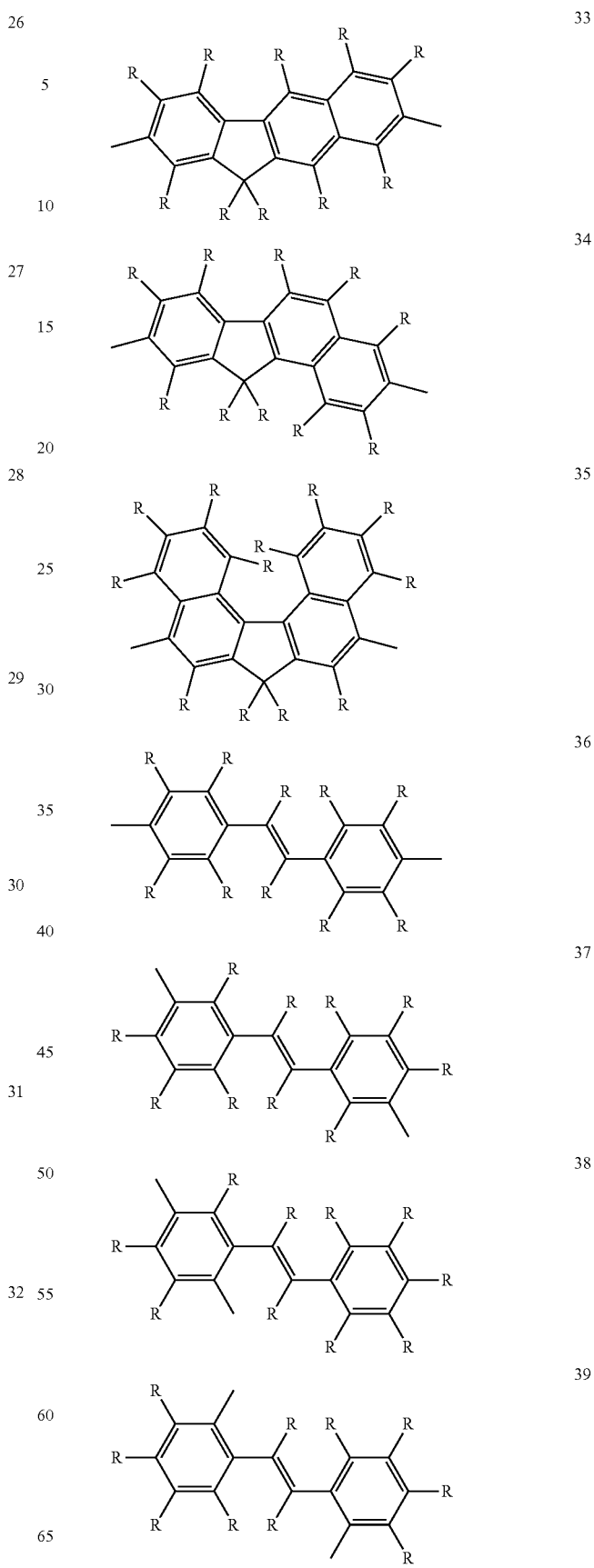

40
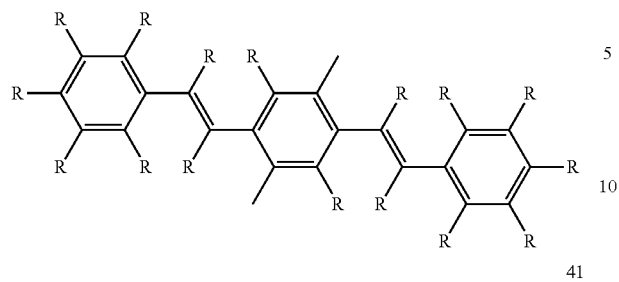
41
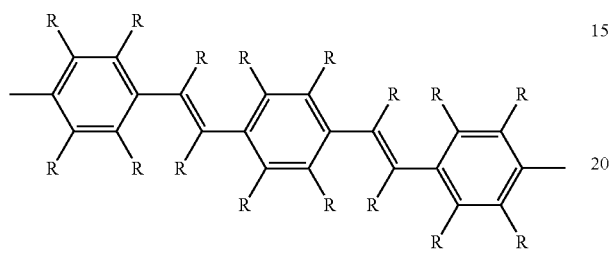
52
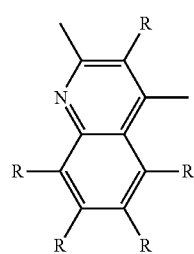
53
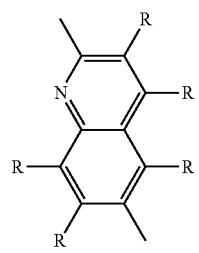
54
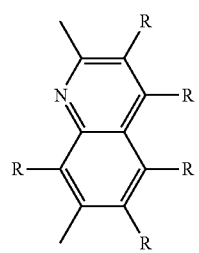
55
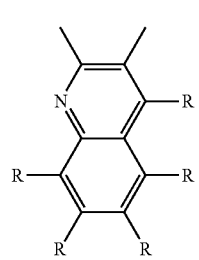
56
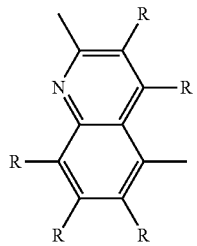
57
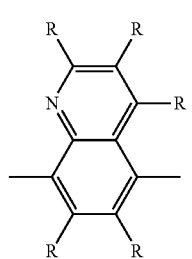
58
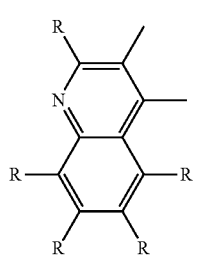
59
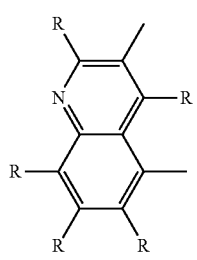
60
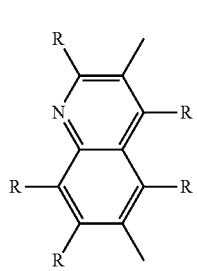
61
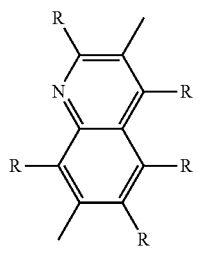

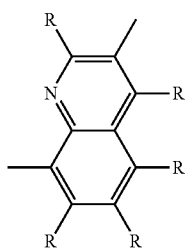
62
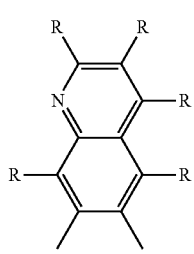
63
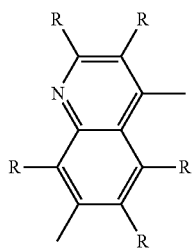
64
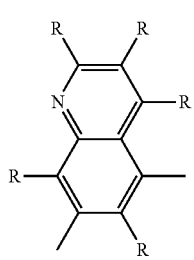
65
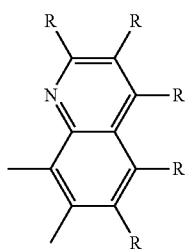
66
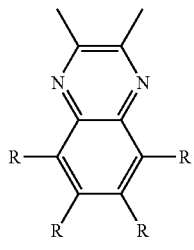
67
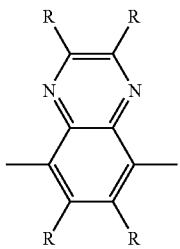
68
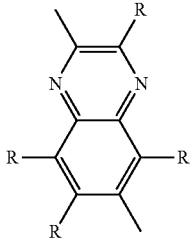
69
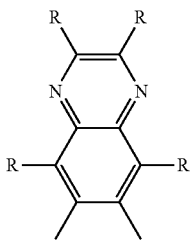
70
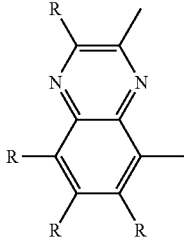
71
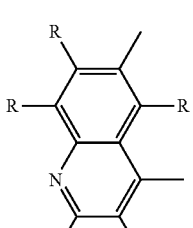
72
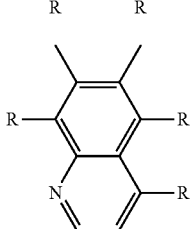
73

-continued
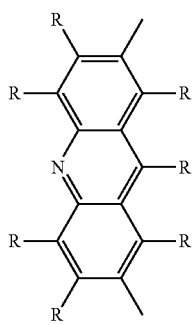
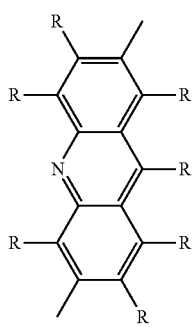
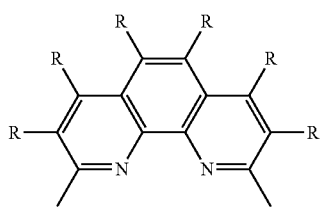
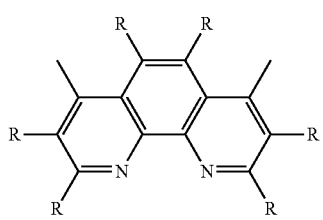
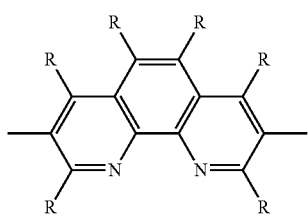
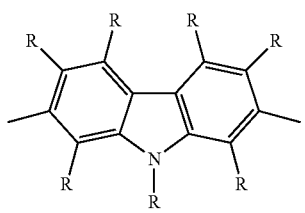
-continued
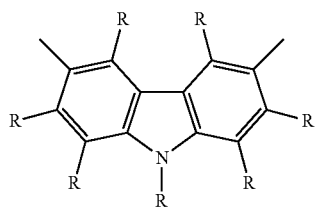
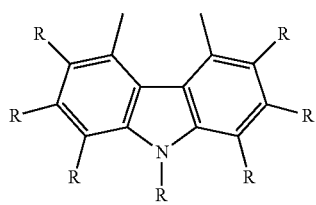
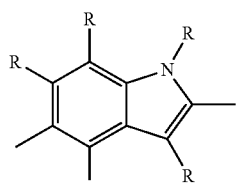
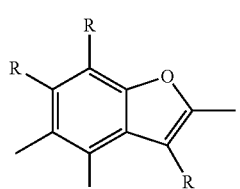
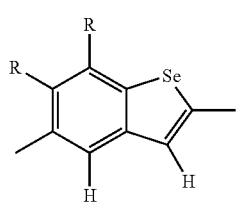
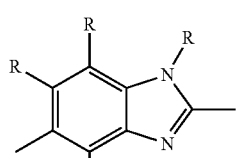
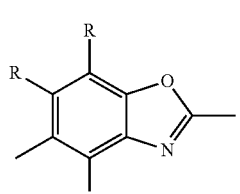
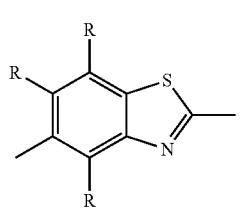

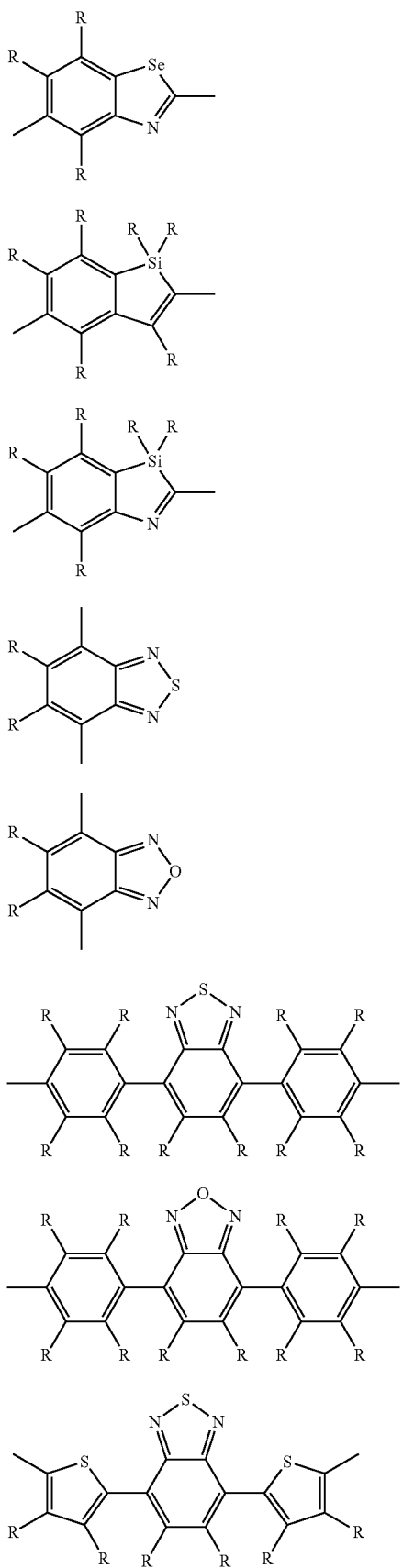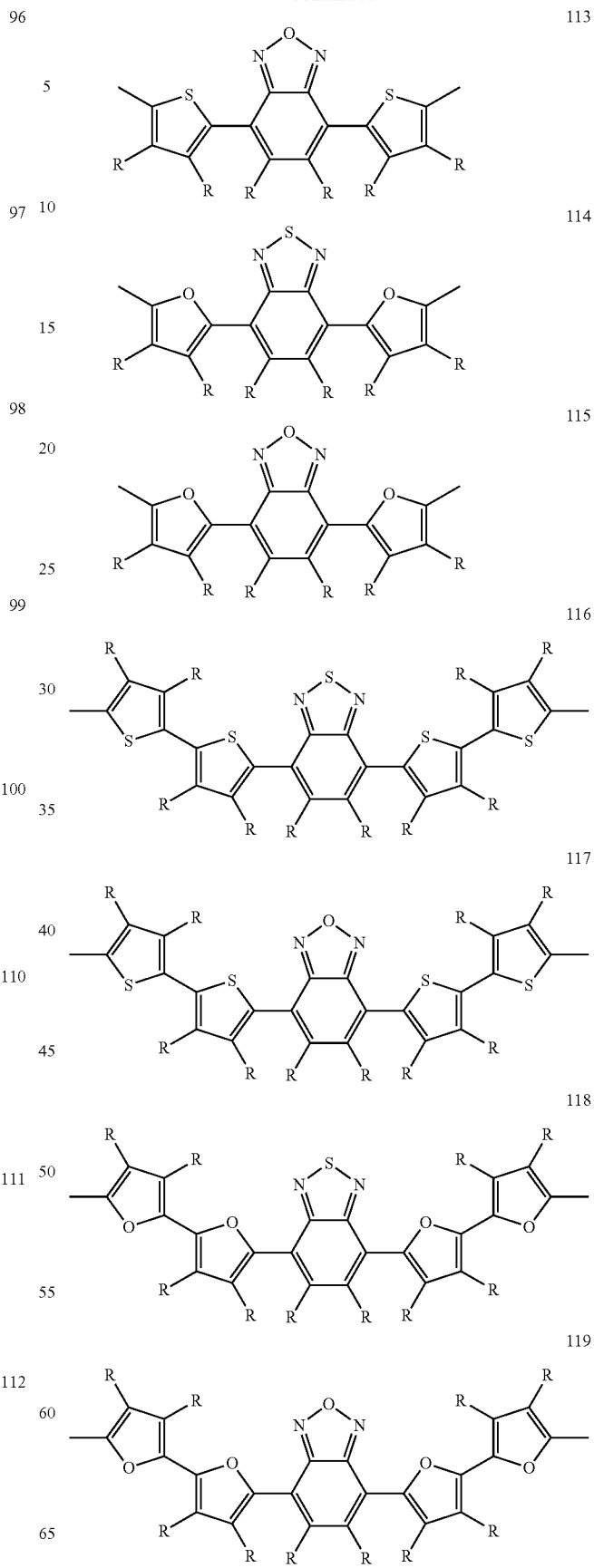

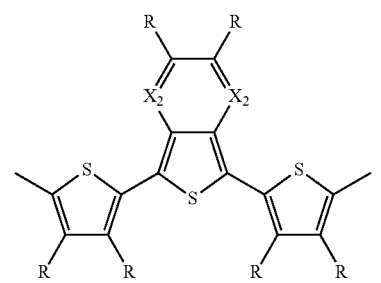
120
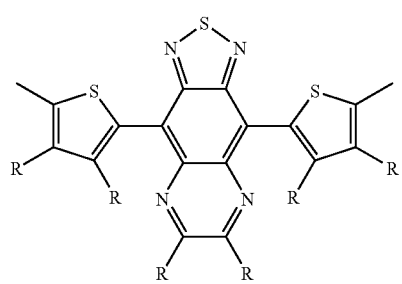
121
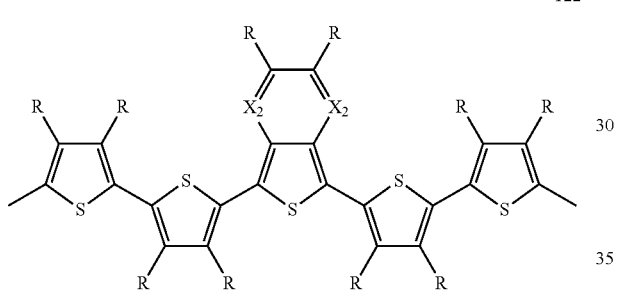
122
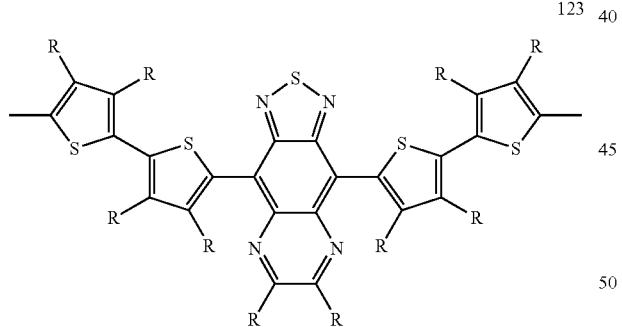
123
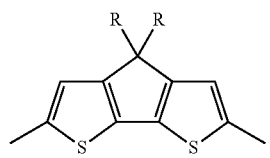
124
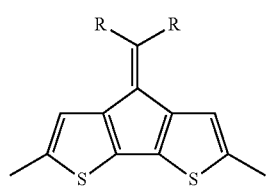
125
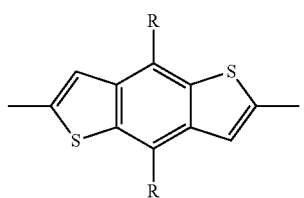
126
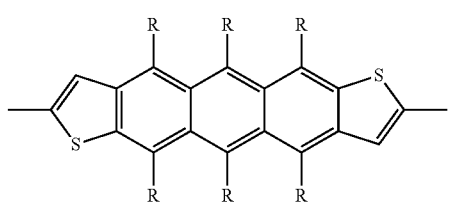
127
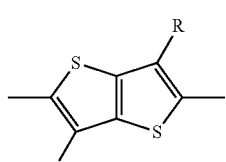
128
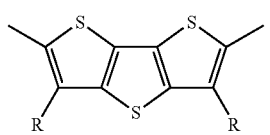
129
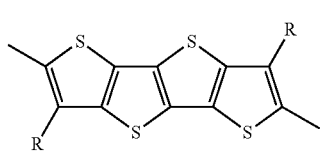
130
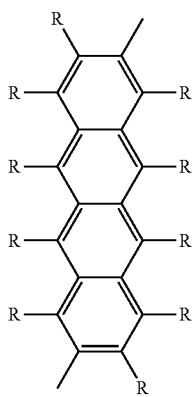
131

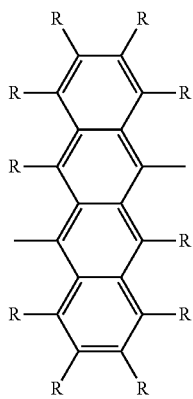

132

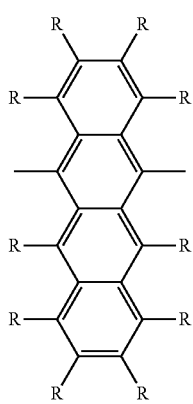

133

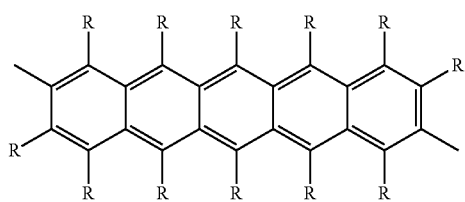

134

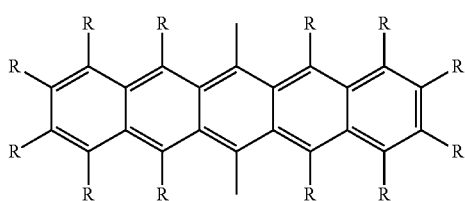

135

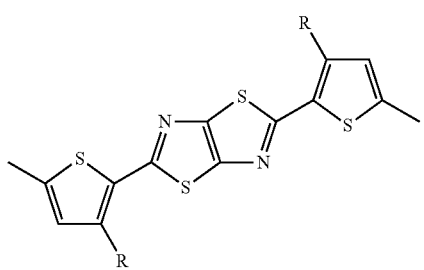

136

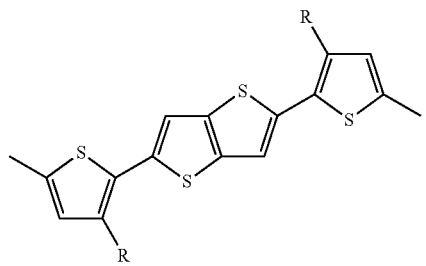

137

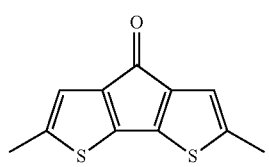

138

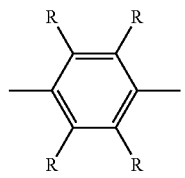

139 wherein R has the same meaning as defined above and, when R is an alkyl group or an alkoxy group, the group preferably has 1 to 20 carbon atoms, more preferably 1 to 16 carbon atoms, and still more preferably 6 to 16 carbon atoms; $X_2$ represents a carbon atom or a nitrogen atom, and preferably a nitrogen atom.

Among groups represented by formulas 1 to 139, preferable groups are represented by formulas 10, 23 to 29, 32 to 35, 53, 61, 68, 82 and 126; more preferable groups are represented by formulas 10, 23 to 26, 29, 82 and 126; and still more preferable groups are represented by formulas 10, 24, 25, 29 and 126, from the viewpoint of a open-end voltage of an organic photoelectric conversion device produced by using the polymer compound of the present invention.

Examples of preferred aspect of the group represented by D include groups represented by formulas (D-1) to (D-3):

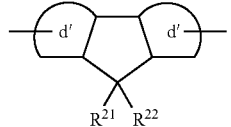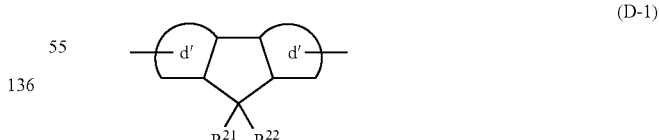

(D-1)

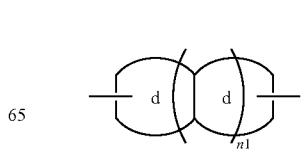

(D-2)

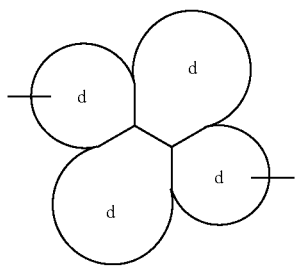
(D-3)

wherein d and d' rings in formulas (D-1) to (D-3) represent an aromatic ring which may have a substituent, and plural d rings may be the same or different and plural d' rings may be the same or different; $R^{21}$ and $R^{22}$ are the same or different and represent a hydrogen atom or a substituent; and n1 represents an integer of 1 or more.

When $R^{21}$ and $R^{22}$ are substituents, examples of the substituent include alkyl groups such as a methyl group, an ethyl group, a butyl group, a hexyl group, an octyl group and a dodecyl group; alkoxy groups such as a methoxy group, an ethoxy group, a butoxy group, a hexyloxy group, an octyloxy group and a dodecyloxy group; and aryl groups such as a phenyl group and a naphthyl group. The substituent is preferably a substituent having 1 to 30 carbon atoms. When the d ring or d' ring has a substituent, specific examples of the substituent include the same groups as specific examples of the substituent represented by $R^{21}$.

In formulas (D-1) to (D-3), the d and d' rings represent an aromatic ring. Examples of the aromatic ring include a benzene ring, a pyrrole ring, a furan ring, a thiophene ring, an oxazole ring, a thiazole ring, a thiadiazole ring, a pyrazole ring, a pyridine ring, a pyrazine ring, an imidazole ring, a triazole ring, an isoxazole ring, an isothiazole ring, a pyrimidine ring, a pyridazine ring, a triazine ring, a naphthalene ring, a quinoxaline ring and the like.

Examples of another preferred aspect of the group represented by D include groups represented by formula (D-4):

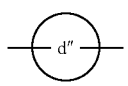
(D-4)

wherein a d" ring represents a benzene ring which may have a substituent, a biphenyl ring which may have a substituent, a terphenyl ring which may have a substituent, or a fused ring containing a hetero atom, which may have a substituent.

When the d" ring is a fused ring containing a hetero atom which may have a substituent, examples of the fused ring containing a hetero atom include a benzothiadiazole ring and a quinoxaline ring.

The group represented by formula (D-1) is preferably a group represented by formula 29, 32, 33 or 34 from the viewpoint of an open-end voltage of an organic photoelectric conversion device produced by using the polymer compound of the present invention.

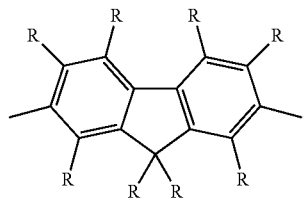
29

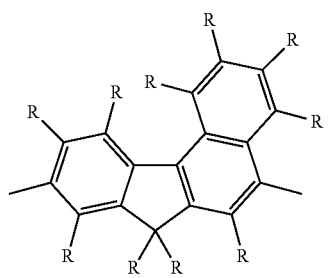
32

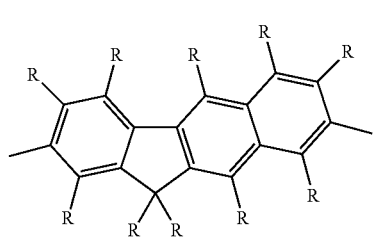
33

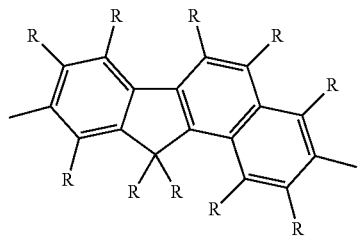
34

The group represented by formula (D-2) is preferably a group represented by formula 5, 10, 20, 81 or 126 from the viewpoint of an open-end voltage of an organic photoelectric conversion device produced by using the polymer compound of the present invention.

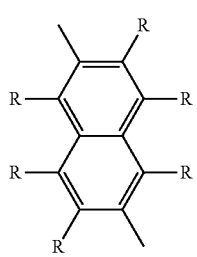
5

-continued

10

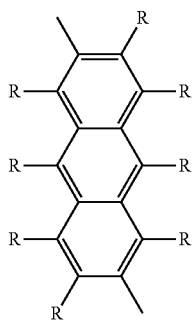

20

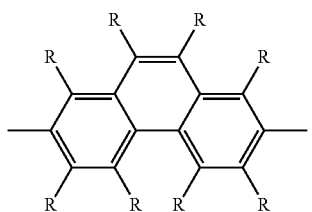

81

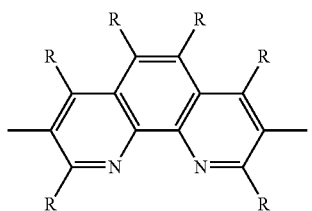

126

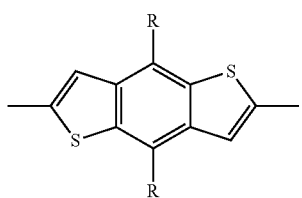

The group represented by formula (D-3) is preferably a group represented by formula 23 or 24 from the viewpoint of an open-end voltage of an organic photoelectric conversion device produced by using the polymeric compound of the present invention.

23

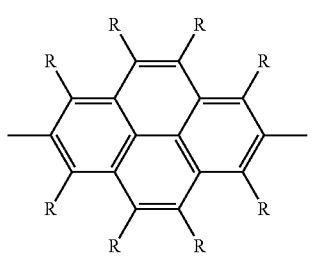

-continued

24

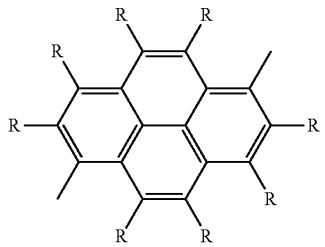

The group represented by formula (D-4) is preferably a group represented by formula 13, 19, 68 or 139 from the viewpoint of an open-end voltage of an organic photoelectric conversion device produced by using the polymeric compound of the present invention.

13

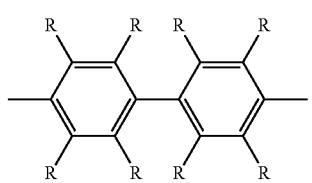

19

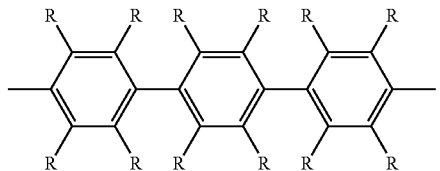

68

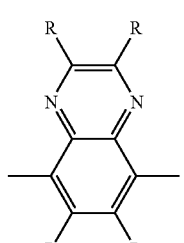

139

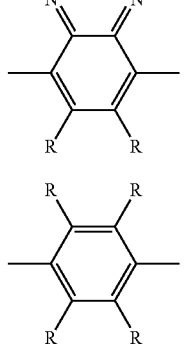

The polymer compound of the present invention is preferably a polymer compound having a weight average molecular weight of 3,000 or more, more preferably a polymer compound having a weight average molecular weight of 3,000 to 10,000,000, still more preferably a polymer compound having a weight average molecular weight of 8,000 to 5,000,000, and particularly preferably a polymer compound having a weight average molecular weight of 10,000 to 1,000,000. When the weight average molecular weight is less than 3,000, defects may sometimes occur in the film formed in case of producing a device. When the weight average molecular weight is more than 10,000,000, solubility in the solvent or coatability in case of producing a device may sometimes deteriorate.

The weight average molecular weight in the present invention refers to a polystyrene-equivalent weight average molecular weight calculated by gel permeation chromatography (GPC) using a polystyrene standard sample.

The polymer compound of the present invention preferably shows a light absorption edge wavelength of 700 nm or more. The light absorption edge wavelength in the present invention means the value obtained by the following method.

In the measurement, a spectrophotometer capable of operating in ultraviolet, visible and near infrared wavelength regions (for example, an ultraviolet-visible-infrared spectrophotometer JASCO-V670 manufactured by JASCO Corporation) is used. In case of using JASCO-V670, since a measurable wavelength is within a range from 200 to 1,500 nm, the measurement is carried out in the wavelength range. First, an absorption spectrum of a substrate used in the measurement is measured. A quartz substrate, a glass substrate and the like are used as the substrate. Then, a thin film containing a first compound is formed from a solution containing a first compound or a melt containing a first compound on the substrate. In the formation of a film form the solution, drying is carried out after formation of the film. Then, an absorption spectrum of a laminate of the thin film and the substrate is obtained. A difference in absorption spectrum between the laminate of the thin film and the substrate and the substrate is obtained as an absorption spectrum of the thin film.

Regarding the absorption spectrum of the thin film, the ordinate denotes an absorbance of a first compound, while the abscissa denotes a wavelength. It is desired that the thickness of the thin film is adjusted so that the absorbance of the largest absorption peak becomes about 0.5 to 2. The absorbance of an absorption peak of the longest wavelength in the absorption peak is assumed to be 100%, and an intersection point between a straight line parallel to the abscissa (wavelength axis) including an absorbance accounting for 50% of the absorbance, and the absorption peak, the intersection point having a longer peak wavelength than that of the absorption peak, is assumed to be a first point. The absorbance of an absorption peak of the longest wavelength in the absorption peak is assumed to be 100%, and an intersection point between a straight line parallel to the abscissa (wavelength axis) including an absorbance accounting for 25% of the absorbance, and the absorption peak, the intersection point having a longer peak wavelength than that of the absorption peak, is assumed to be a second point. An intersection point between a straight line joining the first point and the second point, and a base line is defined as a light absorption edge wavelength. Herein, the base line refers to a straight line joining a third point on an absorption spectrum having a wavelength which is 100 nm longer than a base wavelength, and a fourth point on an absorption spectrum having a wavelength which is 150 nm longer than a base wavelength, in which the base wavelength is a wavelength based on a wavelength of an intersect point between a line parallel to a wavelength axis including 10% accounting for an absorption of an absorption peak at the longest wavelength, and the absorption peak.

The polymer compound of the present invention may include at least one structural unit represented by formula (I). The polymer compound preferably contains two or more structural units on average per one polymer chain, and more preferably three or more structural units on average per one polymer chain.

From the viewpoint of ease of production of the device, the polymer compound of the present invention preferably has high solubility in a solvent. Specifically, the polymer compound of the present invention preferably has solubility capable of preparing a solution containing 0.01% by weight or more of the polymer compound, more preferably a solution containing 0.1% by weight or more of the polymer compound, and still more preferably a solution containing 0.4% by weight or more of the polymer compound.

There is no particular limitation on the method for producing a polymer compound of the present invention, and a method using the Suzuki coupling reaction is preferably used from the viewpoint of ease of synthesis of the polymer compound.

Examples of the method using the Suzuki coupling reaction include a production method including the step of reacting one or more kinds compound represented by formula (100):

$$Q^{100}\text{-}E^{1}\text{-}Q^{200} \qquad (100)$$

wherein $E^1$ represents a structural unit represented by formula (II), and $Q^{100}$ and $Q^{200}$ are the same or different and represent a boric acid residue ($-B(OH)_2$) or a boric acid ester residue, with one or more kinds compound represented by formula (200):

$$T^{1}\text{-}E^{2}\text{-}T^{2} \qquad (200)$$

wherein $E^2$ represents a structural unit represented by formula (III), and $T^1$ and $T^2$ are the same or different and represent a halogen atom, an alkylsulfonate group, an arylsulfonate group or an arylalkylsulfonate group, in the presence of a palladium catalyst and a base.

In this case, it is preferred that the total of the number of mols of one or more kinds compounds represented by formula (200) used in the reaction is excess based on the total of the number of mols of one or more kinds compounds represented by formula (100). When the total of the number of mols of one or more kinds compounds represented by formula (200) used in the reaction is 1 mol, the total of the number of mols of one or more kinds compounds represented by formula (100) is preferably from 0.6 to 0.99 mol, and more preferably from 0.7 to 0.95 mol.

Examples of the boric acid ester residue include groups represented by the following formula:

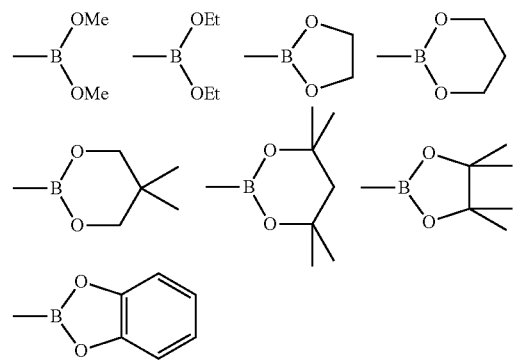

wherein Me represents a methyl group, and Et represents an ethyl group.

Examples of the halogen atom represented by $T^1$ and $T^2$ in formula (200) include a fluorine atom, a chlorine atom, a bromine atom and an iodine atom. From the viewpoint of ease of synthesis of the polymer compound, the halogen atom is preferably a bromine atom or an iodine atom, and more preferably a bromine atom.

Examples of the alkylsulfonate group represented by $T^1$ and $T^2$ in formula (200) include a methanesulfonate group, an ethanesulfonate group and a trifluoromethanesulfonate group. Examples of the arylsulfonate group represented by $T^1$ and $T^2$ include a benzenesulfonate group and a p-toluenesulfonate group. Examples of the arylsulfonate group represented by $T^1$ and $T^2$ include a benzolsulfonate group.

Examples of the palladium catalyst used in the Suzuki coupling reaction include a Pd(0) catalyst and a Pd(II) catalyst. Specific examples of the palladium catalyst include palladium [tetrakis(triphenylphosphine)], palladium acetates, dichlorobis(triphenylphosphine) palladium(II) and the like. From the viewpoint of ease of a reaction (polymerization) operation and a reaction (polymerization) rate, dichlorobis (triphenylphosphine) palladium(II) and palladium acetates are preferable.

There is particular limitation on the addition amount of the palladium catalyst, and the addition amount may be an effective amount as the catalyst and is usually from 0.0001 mol to 0.5 mol, and preferably from 0.0003 mol to 0.1 mol, based on 1 mol of the compound represented by formula (100).

In case of using palladium acetates as the palladium catalyst, phosphorus compounds such as triphenylphosphine, trio-tolyl)phosphine and trio-methoxyphenyl)phosphine may be added as a ligand of the palladium catalyst. The addition amount of the ligand is usually from 0.5 mol to 100 mol, preferably from 0.9 mol to 20 mol, and more preferably from 1 mol to 10 mol, based on 1 mol of the palladium catalyst.

The Suzuki coupling reaction is usually carried out in a solvent. Examples of the solvent include N,N-dimethylformamide, toluene, dimethoxyethane and tetrahydrofuran. From the viewpoint of the solubility of the polymeric compound of the present invention, toluene and tetrahydrofuran are preferable.

Examples of the base used in the Suzuki coupling reaction include an inorganic base, an organic base and an inorganic salt. Examples of the inorganic base include potassium carbonate, sodium carbonate, barium hydroxide and the like. Examples of the organic base include triethylamine, tributylamine and the like. Examples of the inorganic salt include cesium fluoride and the like.

The addition amount of the base is usually from 0.5 mol to 100 mol, preferably from 0.9 mol to 20 mol, and more preferably from 1 mol to 10 mol, based on 1 mol of the compound represented by formula (100). The base may be added in the form of an aqueous solution and the reaction may be carried out in a two phase system of an aqueous phase and an organic phase. In case of reacting in the two phase system, a phase transfer catalyst such as a quaternary ammonium salt may be optionally added.

The reaction temperature varied depending on the solvent, and is usually from about 50 to 160° C., and preferably from 60 to 120° C. from the viewpoint of an increase in molecular weight of the polymer compound. The reaction may be carried out while refluxing the solvent by raising the temperature to around a boiling point of the solvent.

The time during which the reaction is performed (reaction time) is usually from about 0.1 hour to 200 hours. The reaction time is preferably from about 1 hour to 30 hours from the viewpoint of efficiency.

The reaction is carried out in a reaction system in which a Pd(0) catalyst is not deactivated, for example, under an inert atmosphere such as an argon gas or an nitrogen gas. For example, the reaction is carried out in a system in which degassing is sufficiently carried out using an argon gas, a nitrogen gas and the like. Specifically, air in a polymerization vessel (reaction system) is sufficiently replaced by a nitrogen gas and, after degassing, a compound represented by formula (100), a compound represented by formula (200) and dichlorobis(triphenylphosphine) palladium(II) are charged in this polymerization vessel. Furthermore, air in the polymerization vessel is sufficiently replaced by a nitrogen gas and, after degassing, a solvent such as toluene, degassed by nitrogen gas bubbling in advance, is added. Then, a base such as an aqueous sodium carbonate solution, degassed by nitrogen gas bubbling in advance, is added dropwise in the reaction solution. Then, the temperature is raised by heating the reaction solution and the polymerization is carried out while maintaining an inert atmosphere.

The polystyrene-equivalent number average molecular weight of the polymer compound is preferably from $1 \times 10^3$ to $1 \times 10^8$. When the polystyrene-equivalent number average molecular weight is $1 \times 10^3$ or more, it is easy for a thin film made of the polymer compound to become tough. On the other hand, when the polystyrene-equivalent number average molecular weight is $10^8$ or less, it is easy to form a thin film because of high solubility of the polymer compound in the solvent.

When a polymerization active group remains at the end of the polymer compound of the present invention even after the polymerization, characteristics of the device using the polymer compound of the present invention may deteriorate. Therefore, the end of the polymer compound is preferably protected with a stable group. The end of the stable group and the end of the polymer compound are preferably combined through a conjugated bond. The end of the stable group and the end of the polymer compound may be combined through a vinylene group.

The polymer compound of the present invention can be synthesized by polymerization using the compound represented by formula (VI) as one of raw materials:

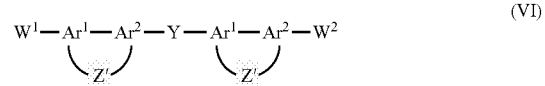

(VI)

wherein $Ar^1$ and $Ar^2$ are the same or different and represents a trivalent heterocyclic group; Z' represents a divalent hydrocarbon group; Y represents a divalent heterocyclic group; $W^1$ and $W^2$ are the same or different and represent a hydrogen atom, a halogen atom, an organotin residue, a boric acid residue ($—B(OH)_2$) or a boric acid derivative residue; two $Ar^1$'s may be the same or different; two $Ar^2$'s may be the same or different; and two Z's may be the same or different.

When $W^1$ and $W^2$ are halogen atoms, examples of the halogen atom include a fluorine atom, a chlorine atom, a bromine atom and an iodine atom. From the viewpoint of ease of synthesis of a polymer compound, the halogen atom is preferably a bromine atom or an iodine atom, and more preferably a bromine atom.

When $W^1$ and $W^2$ are organotin residues, $W^1$ and $W^2$ are represented by the following general formula:

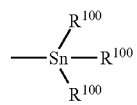

wherein $R^{100}$ are the same or different and represent an alkyl group. From the viewpoint of ease of synthesis of a polymer compound, the number of carbon atoms of the alkyl group is preferably from 1 to 4, more preferably from 1 to 2, and still more preferably 1.

When W¹ and W² are boric acid derivative residues, W¹ and W² are represented by the following general formula:

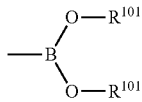

wherein R¹⁰¹ represents a hydrogen atom or an alkyl group. Two R¹⁰¹'s may be the same or different, provided that at least one of R¹⁰¹ is an alkyl group. The alkyl group may be linear or branched. The number of carbon atoms of the alkyl group is preferably from 1 to 10, more preferably from 1 to 5, and still more preferably from 1 to 2. When both two R¹⁰¹s are alkyl groups, two R¹⁰¹s may be connected to each other to form a cyclic ester structure. The cyclic ester structure is preferably an ethylene glycol ester structure, a 1,3-propanediol ester structure, a pinacol ester structure, a 2,2-dimethyl-1,3-propanediol ester structure or a 1,1-dimethyl-3-methyl-1,3-propanediol ester structure, more preferably an ethylene glycol ester structure, a 1,3-propanediol ester structure or a pinacol ester structure, and still more preferably a pinacol ester structure.

Examples of the boric acid derivative residue represented by W¹ and W² include groups represented by formulas (WB-1) to (WB-8):

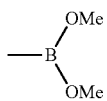
WB-1

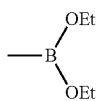
WB-2

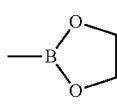
WB-3

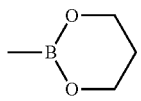
WB-4

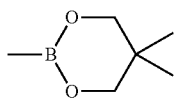
WB-5

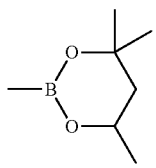
WB-6

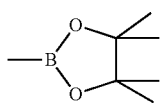
WB-7

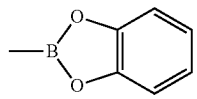
WB-8 wherein Me represents a methyl group, and Et represents an ethyl group.

The boric acid derivative residue is preferably a group containing an ethylene glycol ester (WB-3), a group containing an 1,3-propanediol ester (WB-4), a group containing a pinacol ester group (WB-7), a group containing a 2,2-dimethyl-1,3-propanediol ester (WB-5) or a group containing a 1,1-dimethyl-3-methyl-1,3-propanediol ester (WB-6), more preferably a group containing an ethylene glycol ester, a group containing a 1,3-propanediol ester or a group containing a pinacol ester, and still more preferably a group containing a pinacol ester.

The divalent hydrocarbon group represented by Z' is preferably a group represented by formula (Z-1), (Z-3) or (Z-5):

(Z-1)

(Z-3)

(Z-5)

wherein R¹, R², R⁵ to R¹⁰ are the same or different and represent a hydrogen atom or a substituent.

The polymer compound including a structural unit represented by formula (IV) can also be produced by oxidative polymerization of a compound represented by formula (VI-1):

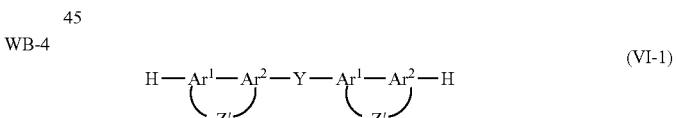
(VI-1)

wherein Ar¹, Ar², Y and Z' have the same meanings as defined above.

In the oxidative polymerization, a catalyst is usually used. A known catalyst is used as the catalyst, and examples thereof include a metal halide, a mixture of a metal halide and an amine complex (metal halide/amine complex) and the like. Examples of metal halide include a monovalent halide, a divalent halide and a trivalent halide of metals such as copper, iron, vanadium, chromium and the like. The metal halide/amine complex can be produced by mixing the metal halide with an amine in a solvent in the presence of oxygen. A molar ratio of the metal halide to the amine used in mixing, metal halide/amine, is preferably from 1/0.1 to 1/200, and more preferably from 1/0.3 to 1/100. Examples of the amine include pyridine, lutidine, 2-methylimidazole and N,N,N',N'-tetramethylethylenediamine.

In the oxidative polymerization, iron chloride may be used as the catalyst (Polym. Prep. Japan, Vol. 48, 309 (1999)). Copper/amine catalysts may also be used (J. Org. Chem., 64, 2264 (1999), J. Polym. Sci. Part A, Polym. Chem., 37, 3702 (1999)). When using copper/amine catalysts, the molecular weight of the polymer compound can be increased.

There is no particular limitation on the solvent used in the oxidative polymerization, as long as the catalyst is a solvent which does not undergo poisoning. Examples of the solvent include a hydrocarbon solvent, an ether solvent and alcohols. Examples of the hydrocarbon solvent include toluene, benzene, xylene, trimethylbenzene, tetramethylbenzene, naphthalene and tetraphosphorus. Examples of the ether solvent include diethyl ether, diisopropyl ether, tetrahydrofuran, 1,4-dioxane, diphenyl ether and tert-butyl methyl ether. Examples of the alcohols include methanol, ethanol, isopropanol and 2-methoxyethanol.

The reaction temperature of the oxidative polymerization is usually from −100° C. to 100° C., and preferably from −50 to 50° C.

The polymer compound of the present invention may be a block copolymer, a random copolymer or an alternate copolymer. Examples of the method for producing a copolymer include a method in which two or more kinds of monomers are mixed and then polymerized, a method in which one kind of a monomer is polymerized and then the second monomer is added and the like. It is possible to produce a block copolymer, a random copolymer, an alternate copolymer, a multi-block copolymer, a graft copolymer and the like by using these methods or using them in combination.

The polymer compound of the present invention can also be synthesized by polymerizing, as one of raw materials, a compound represented by formula (VII), which is one aspect of the compound represented by formula (VI):

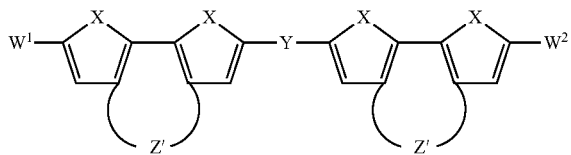

(VII)

wherein X represents a sulfur atom, an oxygen atom, a selenium atom, —NH— or —N(R$^a$)—; R$^a$ represents a substituent; Y, Z', W$^1$ and W$^2$ have the same meanings as defined above; and four Xs may be the same or different.

The compound represented by formula (VII) can be produced by a coupling reaction of a compound represented by formula (α) with a compound represented by formula (β):

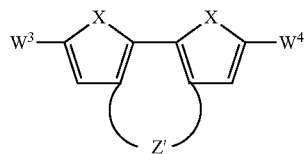

(α)

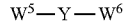

(β)

wherein X, Y and Z' in formulas (α) and (β) have the same meanings as defined above; and W$^3$ to W$^6$ are the same or different and represent a hydrogen atom, a halogen atom, an organotin residue, a boric acid residue or a boric acid derivative residue. Definition and specific examples of the halogen atom, organotin residue and boric acid derivative residue are the same as those of the halogen atom, organotin residue and boric acid derivative residue represented by W$^1$.

In the coupling method, the Negishi coupling reaction, Migita-Kosugi-Stille coupling, Suzuki-Miyaura coupling reaction, Kumada-Tamao-Corriu coupling reaction and the like can be used.

Among the compound represented by formula (VII), a compound in which W$^1$ and W$^2$ are bromine atoms can be suitably used in the coupling reaction.

A known method can be used as the method in which a compound represented by formula (VII) in which W$^1$ and W$^2$ are bromine atoms is produced from a compound represented by formula (VII) in which W$^1$ and W$^2$ are hydrogen atoms. Examples thereof include a method in which a compound represented by formula (VII) in which W$^1$ and W$^2$ are hydrogen atoms is brominated by bringing into contact with bromine or N-bromosuccineimide (NBS). The bromination conditions can be optionally set. The method in which compound represented by formula (VII) in which W$^1$ and W$^2$ are hydrogen atoms is reacted with NBS in a solvent is desired since a bromination ratio is high and also selectivity of the introduction position of a bromine atom increases. Examples of the solvent used in the method include N,N-dimethylformamide, chloroform, methylene chloride, carbon tetrachloride and the like. The reaction time is usually from about 1 minute to 10 hours, and the reaction temperature is usually from about −50° C. to 50° C. The use amount of bromine is preferably from 1 mol to 5 mol based on 1 mol of the compound represented by formula (VII) in which W$^1$ and W$^2$ are hydrogen atoms. After completion of the reaction, for example, the reaction is terminated by adding water to the reaction solution and then a conventional post treatment such as extraction of the product with an organic solvent and subsequent distillation off of the solvent is performed, and thus it is possible to obtain a compound represented by formula (VII) in which W$^1$ and W$^2$ are bromine atoms. The product can be isolated and then purified by a method such as fractionation by chromatography, recrystallization or the like.

The polymer compound including a structural unit represented by formula (I) can also be synthesized by polymerization using a compound represented by formula (VIII) as one of raw materials:

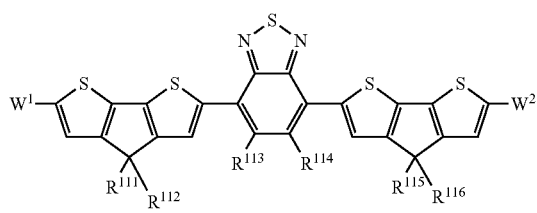

(VIII)

wherein R$^{111}$ to R$^{116}$ are the same or different and represent a hydrogen atom or a substituent. When R$^{111}$ to R$^{116}$ are substituents, examples of the substituent include alkyl groups such as a methyl group, an ethyl group, a butyl group, a hexyl group, an octyl group and an dodecyl group; alkoxy groups such as a methoxy group, an ethoxy group, a butoxy group, a hexyloxy group, an octyloxy group and a dodecyloxy group; aryl groups such as a phenyl group and a naphthyl group; heteroaryl groups such as a thienyl group; and the like. R$^{111}$, $R^{112}$, $R^{115}$ and $R^{115}$ are preferably substituents. When the substituent is an alkyl group or an alkoxy group, the group is preferably a group having 1 to 20 carbon atoms, more preferably a group having 1 to 16 carbon atoms, and still more preferably a group having 6 to 16 carbon atoms. $R^{113}$ and $R^{114}$ are preferably hydrogen atoms. $W^1$ and $W^2$ have the same meanings as defined above.

The compound represented by formula (VIII) can be produced by a coupling reaction of a compound represented by formula (γ) with a compound represented by formula (ε):

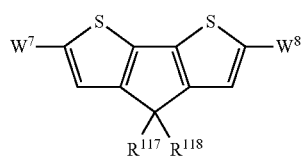

(γ)

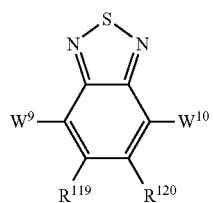

(ε)

wherein $W^7$ to $W^{10}$ in formulas (γ) and (ε) are the same or different and represent a hydrogen atom, a halogen atom, an organotin residue, a boric acid residue or a boric acid derivative residue. $R^{117}$ to $R^{120}$ are the same or different and represent a hydrogen atom or a substituent. When $R^{117}$ to $R^{120}$ are substituents, examples of the substituent include alkyl groups such as a methyl group, an ethyl group, a butyl group, a hexyl group, an octyl group and a dodecyl group; alkoxy groups such as a methoxy group, an ethoxy group, a butoxy group, a hexyloxy group, an octyloxy group and a dodecyloxy group; aryl groups such as a phenyl group and a naphthyl group; heteroaryl groups such as a thienyl group; and the like. $R^{117}$ and $R^{118}$ are preferably substituents. When the substituent is an alkyl group or an alkoxy group, a group is preferably a group having 1 to 20 carbon atoms, more preferably a group having 1 to 16 carbon atoms, and still more preferably a group having 6 to 16 carbon atoms. $R^{119}$ and $R^{120}$ are preferably hydrogen atoms.

The Negishi coupling reaction, Migita-Kosugi-Stille coupling, Suzuki-Miyaura coupling reaction, Kumada-Tamao-Corriu coupling reaction and the like can be used in the coupling method.

Preferred method for producing a compound represented by formula (VIII) is a method in which the compound is produced by reacting a compound represented by formula (γ) in which $W^7$ is a hydrogen atom and $W^8$ is a bromine atom, with a compound represented by formula (ε) in which $W^9$ and $W^{10}$ are boric acid ester residues through the Suzuki-Miyaura coupling reaction.

When a polymer compound having a group represented by formula (126) is produced by using the Suzuki-Miyaura coupling reaction, the compound is preferably produced by using a compound represented by formula (IX):

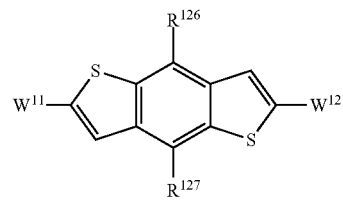

(IX)

wherein $R^{126}$ and $R^{127}$ are the same or different and represent a hydrogen atom or a substituent. When $R^{126}$ and $R^{127}$ are substituents, examples of the substituent include alkyl groups such as a methyl group, an ethyl group, a butyl group, a hexyl group, an octyl group and a dodecyl group; alkoxy groups such as a methoxy group, an ethoxy group, a butoxy group, a hexyloxy group, an octyloxy group and a dodecyloxy group; aryl groups such as a phenyl group and a naphthyl group; heteroaryl groups such as a thienyl group; and the like. When the substituent is an alkyl group or an alkoxy group, a group is preferably a group having 1 to 20 carbon atoms, more preferably a group having 1 to 16 carbon atoms, and still more preferably a group having 6 to 16 carbon atoms. $W^{11}$ and $W^{12}$ are the same or different and represent a boric acid residue or a boric acid derivative residue. Definition and specific examples of the boric acid derivative residue represented by $W^{11}$ and $W^{12}$ are the same as those of the boric acid derivative residue represented by the above-mentioned $W^1$ and $W^2$.

Since the polymer compound of the present invention can exhibit high electron and/or hole transportability, it is possible to transport electrons or holes injected from an electrode, or charges generated by light absorption when using an organic thin film containing the compound in the device. It is possible to suitably use in various electronic devices such as photoelectric conversion devices, organic thin film transistors and organic electroluminescence devices by making use of these characteristics. These devices will be individually described below.

<Photoelectric Conversion Device>

The photoelectric conversion device containing the polymer compound of the present invention comprises one or more active layers containing the polymer compound of the present invention between a pair of electrodes, at least one of which is transparent or translucent.

Preferred mode of the photoelectric conversion device containing the polymer compound of the present invention comprises a pair of electrodes, at least one of which is transparent or translucent, and an active layer formed from an organic composition of a p-type organic semiconductor and an n-type organic semiconductor. The polymer compound of the present invention is preferably used as the p-type organic semiconductor.

The photoelectric conversion device is usually formed on a substrate. This substrate may be a substrate which forms an electrode and does not undergo a chemical change in case of forming a layer of an organic substance. Examples of the material of the substrate include glass, plastic, polymeric film and silicon. In case of an opaque substrate, the opposite electrode (i.e., electrode which is far from the substrate) is preferably transparent or translucent.

Another aspect of a photoelectric conversion device containing the polymer compound of the present invention is a photoelectric conversion device comprising a first active layer containing the polymer compound of the present invention between a pair of electrodes, at least one of which is transparent or translucent, and a second active layer containing an electron accepting compound such as a fullerene derivative, adjacent to the first active layer.

Examples of the material of a transparent or translucent electrode include a conductive metal oxide film, a translucent metal thin film and the like. Specifically, it is possible to use films made of conductive materials composed of indium oxide, zinc oxide, tin oxide, and indium tin oxide (ITO) or indium zinc oxide as a complex thereof, NESA, gold, platinum, silver and copper. The material is preferably ITO, indium zinc oxide or tin oxide. Examples of the method for producing an electrode include a vacuum deposition method, a sputtering method, an ion plating method, a plating method and the like. It is possible to use, as an electrode material, organic transparent conductive films of polyaniline and derivatives thereof, and polythiophene and derivatives thereof.

One electrode may not be transparent, and metals and conductive polymers can be used as the electrode material of the electrode. Specific examples of the electrode material include metals such as lithium, sodium, potassium, rubidium, cesium, magnesium, calcium, strontium, barium, aluminum, scandium, vanadium, zinc, yttrium, indium, cerium, samarium, europium, terbium and ytterbium; alloys composed of two or more metals; alloys composed of one or more kinds of metals and one or more kinds of metals selected from the group consisting of gold, silver, platinum, copper, manganese, titanium, cobalt, nickel, tungsten and tin; graphite, graphite intercalation compounds, polyaniline and derivatives thereof, polythiophene and derivatives thereof. Examples of the alloy include magnesium-silver alloys, magnesium-indium alloys, magnesium-aluminum alloys, indium-silver alloys, lithium-aluminum alloys, lithium-magnesium alloys, lithium-indium alloys, calcium-aluminum alloy and the like.

As means for improving photoelectric conversion efficiency, additional intermediate layers other than the active layer may be used. Examples of the material used in the intermediate layer include halides of alkali metals and alkali earth metals, such as lithium fluoride; oxides such as titanium oxide; PEDOT (poly-3,4-ethylenedioxythiophene); and the like.

<Active Layer>

The polymer compound of the present invention contained in the active layer may be either one kind, or a mixture of two or more kinds. In order to enhance hole transportability of the active layer, compounds other than the polymer compound of the present invention may be contained in the active layer as the electron donating compound and/or the electron accepting compound. The electron donating compound and electron accepting compound are relatively determined from energy level of these compounds.

Examples of the electron donating compound include pyrazoline derivatives, arylamine derivatives, stilbene derivatives, triphenyldiamine derivatives, oligothiophene and derivatives thereof, polyvinylcarbazole and derivatives thereof, polysilane and derivatives thereof, polysiloxane derivatives having an aromatic amine residue in the side chain or main chain, polyaniline and derivatives thereof, polythiophene and derivatives thereof, polypyrrole and derivatives thereof, polyphenylenevinylene and derivatives thereof, and polythienylenevinylene and derivatives thereof.

Examples of the electron accepting compound include carbon materials such as carbon nano-tubes, metal oxides such as titanium oxide, oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, metal complexes of 8-hydroxyquinoline and derivatives thereof, polyquinoline and derivatives thereof, polyquinoxaline and derivatives thereof, polyfluorene and derivatives thereof, phenanthroline derivatives such as 2,9-dimethyl-4,7-diphenyl-1,10-phenanthroline (bathocuproine), fullerene and fullerene derivatives. Among these electron accepting compounds, titanium oxide, carbon nanotubes, fullerene, fullerene derivatives are preferable, and fullerene and fullerene derivatives are particularly preferable.

Examples of fullerene and the fullerene derivatives include $C_{60}$, $C_{70}$, $C_{76}$, $C_{78}$, $C_{84}$ and derivatives thereof. The fullerene derivatives are compounds in which a part of fullerene is modified.

Examples of the fullerene derivatives include compounds represented by formula (X), compounds represented by formula (XI), compounds represented by formula (XII) and compounds represented by formula (XIII):

(X)

(XI)

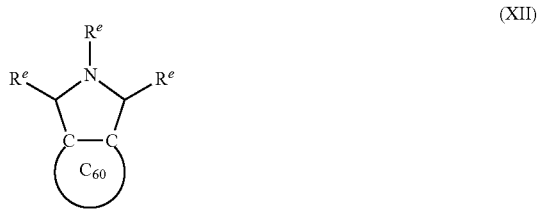

(XII)

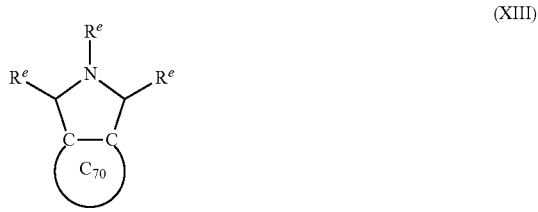

(XIII)

wherein $R^d$ in formulas (X) to (XIII) is an alkyl group, an aryl group, a heteroaryl group or a group having an ester structure, and plural $R^d$s may be the same or different; $R^e$ represents an alkyl group or an aryl group, and plural $R^e$s may be the same or different.

The alkyl group represented by $R^d$ and $R^e$ usually has 1 to 20 carbon atoms. Specific examples of the alkyl group include a methyl group, an ethyl group, a propyl group, an isopropyl group, a butyl group, a tert-butyl group, an isobutyl group, a sec-butyl group, a hexyl group and an octyl group.

The aryl group represented by $R^d$ and $R^e$ usually has 6 to 60 carbon atoms. The aryl group may have a substituent. Specific examples of the aryl group include a phenyl group, a naphthyl group, an anthryl group, a pyrenyl group, a tolyl group and a xylyl group.

The heteroaryl group represented by $R^d$ usually has 3 to 60 carbon atoms, and examples thereof include a thienyl group, a pyrrolyl group, a furyl group, a pyridyl group, a quinolyl group, an isoquinolyl group and the like.

Examples of the group having an ester structure represented by $R^d$ include groups represented by formula (XIV):

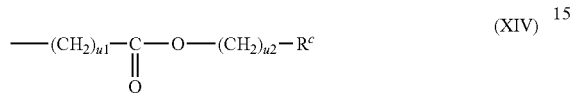

(XIV)

wherein u1 represents an integer of 1 to 6; u2 represents an integer of 0 to 6; and $R^c$ represents an alkyl group, an aryl group or a heteroaryl group.

Definition and specific examples of the alkyl group, aryl group and heteroaryl group which are represented by $R^c$ are the same as those of the alkyl group, aryl group and heteroaryl group which are represented by $R^d$.

Examples of the specific structure of the $C_H$ fullerene derivatives include the followings.

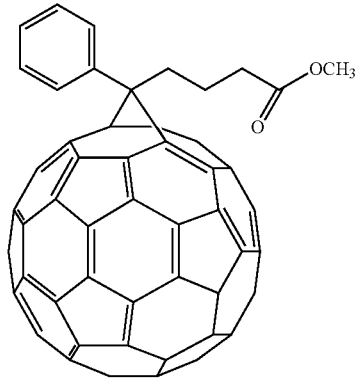

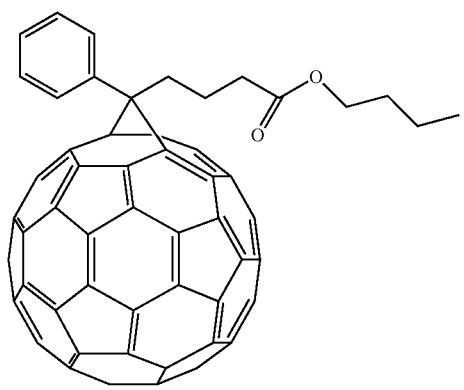

-continued

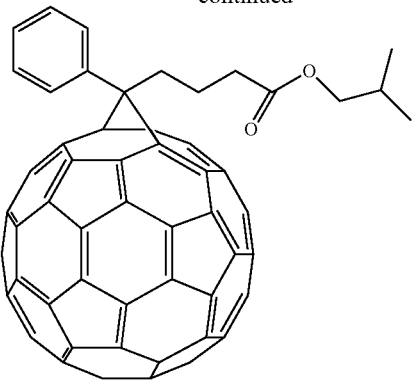

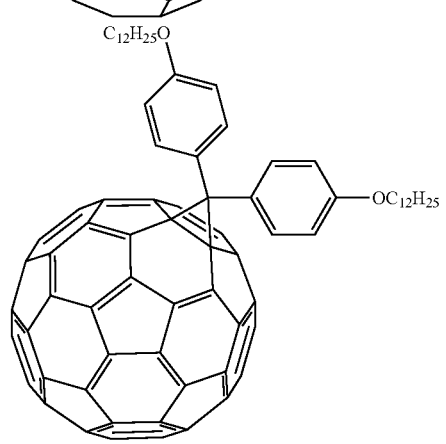

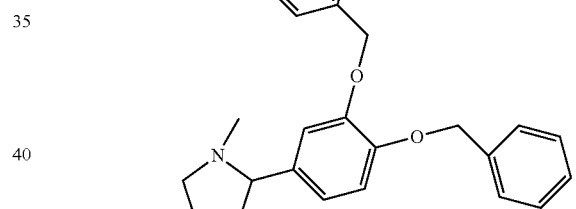

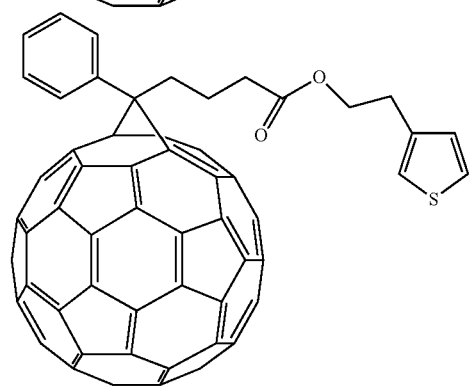

-continued

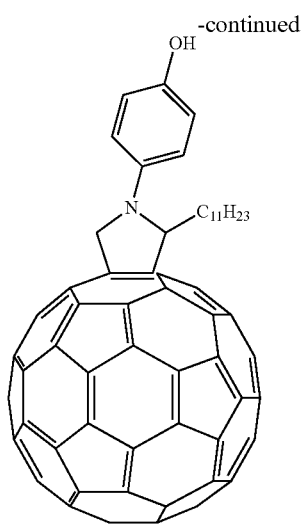

Examples of the specific structure of the $C_{70}$ fullerene derivatives include the followings.

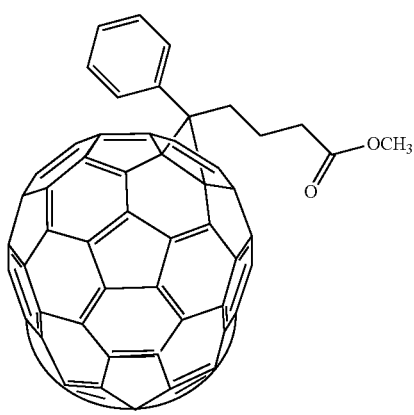

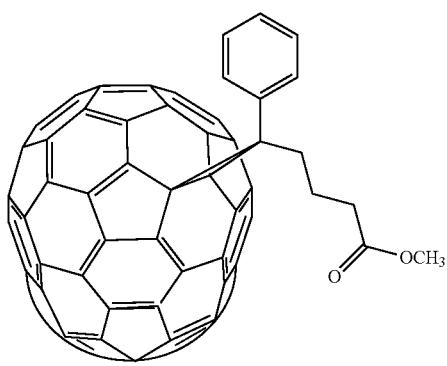

-continued

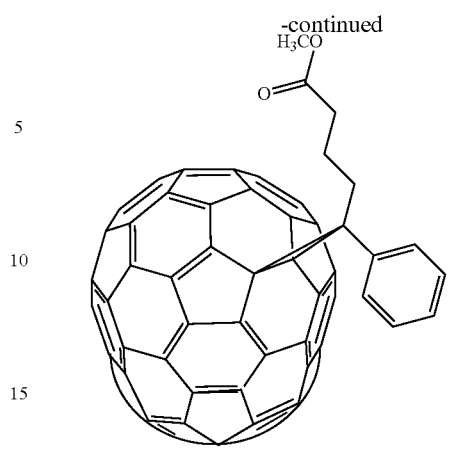

Examples of fullerene derivatives include [6,6]-phenyl C61 butyric acid methyl ester (C60PCBM), [6,6]-phenyl C71 butyric acid methyl ester (C70PCBM), [6,6]phenyl-C85 butyric acid methyl ester (C84PCBM), [6,6]thienyl-C61 butyric acid methyl ester and the like.

When the polymer compound of the present invention and a fullerene derivative are contained in an active layer, the amount of the fullerene derivative is preferably from 10 to 1,000 parts by weight, and more preferably from 20 to 500 parts by weight, based on 100 parts by weight.

The thickness of the active layers is preferably from 1 nm to 100 μm, more preferably from 2 nm to 1,000 nm, still more preferably from 5 nm to 500 nm, and yet still more preferably from 20 nm to 200 nm.

The active layer may be formed by any method, and examples of the method include a method in which a film is formed from a solution containing a polymer compound, and a film forming method by a vacuum deposition method.

<Method for Production of Photoelectric Conversion Device>

Preferred method for producing a photoelectric conversion device is a method for producing a device including a first electrode and a second electrode, and an active layer between the first electrode and the second electrode, the method comprising the steps of applying a solution (ink) containing the polymer compound of the present invention, an electron accepting compound and a solvent on the first electrode by a coating method to form an active layer; and forming the second electrode on the active layer.

The solvent used to form a film from a solution may be a solvent which dissolves the polymer compound of the present invention. Examples of the solvent include unsaturated hydrocarbon solvents such as toluene, xylene, mesitylene, tetraphosphorus, decalin, bicyclohexyl, n-butylbenzene, sec-butylbenzene and tert-butylbenzene; halogenated saturated hydrocarbon solvents such as carbon tetrachloride, chloroform, dichloromethane, dichloroethane, chlorobutane, bromobutane, chloropentane, bromopentane, chlorohexane, bromohexane, chlorocyclohexane and bromocyclohexane; halogenated unsaturated hydrocarbon solvents such as chlorobenzene, dichlorobenzene and trichlorobenzene; and ether solvents such as tetrahydrofuran and tetrahydropyran. The polymer compound of the present invention can be usually dissolved in the solvent in the proportion of 0.1% by weight or more.

In case of forming a film using a solution, it is possible to use coating methods such as a slit coating method, a knife coating method, a spin coating method, a casting method, a microgravure coating method, a gravure coating method, a bar coating method, a roll coating method, a wire bar coating method, a dip coating method, a spray coating method, a screen printing method, a gravure printing method, a flexo printing method, an offset printing method, an ink-jet coating method, a dispenser printing method, a nozzle coating method and a capillary coating method. Among these methods, a slit coating method, a capillary coating method, a gravure coating method, a microgravure coating method, a bar coating method, a knife coating method, a nozzle coating method, an ink-jet coating method and a spin coating method are preferable.

From the viewpoint of film forming properties, a surface tension of the solvent at 25° C. is preferably 15 mN/m or more, more preferably more than 15 mN/m and less than 100 mN/m, and still more preferably more than 25 mN/m and less than 60 mN/m.

<Use of Photoelectric Conversion Device>

In a photoelectric conversion device using the polymer compound of the present invention, a photoelectromotive force is generated between electrodes by irradiating with light such as sunlight from a transparent or translucent electrode, and thus enabling the photoelectric conversion device to operate as an organic thin film solar battery. It is also possible to use as an organic thin film solar battery module by piling up plural organic thin film solar batteries.

A photocurrent is applied by irradiating with light from a transparent or translucent electrode in a state where a voltage is applied between electrodes or not, and thus enabling the photoelectric conversion device to operate as an organic optical sensor. It is also possible to use as an organic image sensor by piling up plural organic optical sensor.

It is also possible to use the above-mentioned organic thin film transistor as a pixel driving device used to control uniformity of a screen luminance and a screen rewriting rate of electrophoretic displays, liquid crystal displays, organic electroluminescence displays and the like.

<Solar Battery Module>

The organic thin film solar battery can adopt a module structure which is basically the same as that of a conventional solar battery module. The solar battery module commonly adopt a structure in which cells are formed on a supporting substrate made of metal, ceramic or the like and a surface thereof is covered with a filling resin or a cover glass, and light is incorporated from the opposite side of the supporting substrate. It is also possible to adopt a structure in which a transparent material such as a reinforced glass is used for a supporting substrate and cells are formed thereon, and light is incorporated from the transparent supporting substrate side. Specifically, there have been known module structure called a super-straight type, a sub-straight type or a potting type module structure, and a substrate integrated type module structure used in an amorphous silicon solar battery. The organic thin film solar battery of the present invention can appropriately select these module structures according to the intended purposes, places and environments.

A typical super-straight type module or sub-straight type module has a structure in which cells are arranged at given intervals between supporting substrates, one or both of which is/are transparent and subjected to an antireflection treatment and adjacent cells are connected to each other by a metal lead or flexible wiring, and also a current collecting electrode is arranged at the outer peripheral portion and generated power is extracted outside. For the purpose of protection of cells and improving current collecting efficiency, various plastic materials such as ethylenevinyl acetate (EVA) may be used in the form of a film or a filling resin between a substrate and cells according to the intended purposes. In case of using in the place where coating of a surface with a hard material is not required, for example, the place with less impact from the outside, a block function is imparted by forming a surface protective layer using a transparent plastic film or curing the filling resin, and thus a supporting substrate of one side can be omitted. The periphery of the supporting substrate is fixed by a frame made of metal in a sandwich-shape so as to ensure inside sealing and rigidity of a module, while the space between the supporting substrate and the frame is close-sealed with a sealing material. It is also possible to form a solar battery on a curved surface by using a pliable material as a cell per se or a supporting substrate, a filling material and a sealing material. In case of a solar battery using a flexible support such as a polymer film, a cell body can be produced by sequentially forming cells while feeding a roll-shaped support, cutting into a desired size and sealing the peripheral portion using a material which is flexible and has moisture barrier properties. It is also possible to adopt a module structure called "SCAF" described in Solar Energy Materials and Solar Cells, 48, p383-391. It is also possible to use a solar battery using a flexible support in a state of being adhered and fixed to a curved glass or the like.

<Organic Electroluminescence Device>

The polymer compound of the present invention can also be used in an organic electroluminescence device (organic EL device). The organic EL device comprises an emitting layer between a pair of electrodes, at least one of which is transparent or translucent. The organic EL device may comprise, in addition to the emitting layer, a hole transporting layer and an electron transporting layer. The polymer compound of the present invention is contained in any one of the emitting layer, hole transporting layer and electron transporting layer. In the emitting layer, a charge transporting material (which means a generic term of an electron transporting material and a hole transporting material) may be contained, in addition to the polymer compound of the present invention. Examples of the organic EL device comprises a device containing an anode, an emitting layer and a cathode; a device including an anode, an emitting layer, an electron transporting layer and a cathode, the device further including, between the cathode and the emitting layer, an electron transporting layer containing electron transporting material adjacent to the emitting layer; a device containing an anode, a hole transporting layer, an emitting layer and a cathode, the device further containing, between the anode and the emitting layer, a hole transporting layer containing a hole transporting material adjacent to the emitting layer; a device containing an anode, a hole transporting layer, an emitting layer, an electron transporting layer and a cathode; and the like.

<Organic Transistor>

The polymer compound of the present invention can also be used in an organic thin film transistor. Examples of the organic thin film transistor include an organic thin film transistor with the configuration including a source electrode and a drain electrode, an organic semiconductor layer (active layer) which would serve as a current path between these electrodes, and a gate electrode for controlling an amount of a current which passes through the current path, and the organic semiconductor layer is composed by the above-mentioned organic thin film. Examples of such an organic thin film transistor include a field effect and static induction organic thin film transistors The field effect organic thin film transistor preferably comprises a source electrode and a drain electrode, an organic semiconductor layer (active layer) which serves as a current path between these electrodes, a gate electrode for controlling the amount of a current passing through the current path, and insulating layer arranged between the organic semiconductor layer and the gate electrode. Particularly, the source electrode and the drain electrode are arranged in contact with the organic semiconductor layer (active layer) and also a gate electrode is preferably arranged while interposing between insulating layers in contact with the organic semiconductor layer. In the field effect organic thin film transistor, the organic semiconductor layer is composed of an organic thin film containing the polymer compound of the present invention.

The static induction organic thin film transistor includes a source electrode and a drain electrode, an organic semiconductor layer (active layer) which serves as a current path between these electrodes, a gate electrode for controlling the amount of a current passing through the current path, and the gate electrode is preferably provided in the organic semiconductor layer. It is particularly preferred that the source electrode, drain electrode and gate electrode provided in the organic semiconductor layer are provided in contact with the organic semiconductor layer. Herein, the structure of the gate electrode may be a structure which forms a current path through which a flows from a source electrode to a drain electrode, and also enables control of the amount of current which flows through a current path at a voltage applied to the gate electrode, and the structure includes a comb-shaped electrode. Also in a static induction organic thin film transistor, the organic semiconductor layer is composed of an organic thin film containing the polymer compound of the present invention.

When using the polymer compound of the present invention as the static induction organic thin film transistor, $R^1$ to $R^{10}$ in formulas (Z-1) to (Z-5) preferably represents a straight-chain alkyl group, more preferably a straight-chain alkyl group having 3 to 20 carbon atoms, and still more preferably a straight-chain alkyl group having 6 to 18 carbon atoms, from the viewpoint of an improvement in transistor characteristics.

(Z-1)

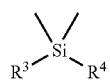
(Z-2)

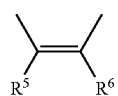
(Z-3)

(Z-4)

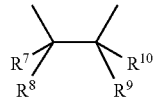
(Z-5)

EXAMPLES

Examples will be described so as to explain the present invention in more detail, but the present invention is not limited thereto.

(NMR Measurement)

NMR measurement was carried out by dissolving a compound in deuterated chloroform using an NMR analyzer (INOVA300, manufactured by Varian).

(Measurement of number average molecular weight and weight average molecular weight).

The number average molecular weight and weight average molecular weight were determined in terms of polystyrene-equivalent number average molecular weight and weight average molecular weight by gel permeation chromatography (GPC) (manufactured by Shimadzu Corporation under the trade name of LC-10Avp). A polymer compound to be measured was dissolved in tetrahydrofuran so that the concentration becomes about 0.5% by weight and the obtained solution (30 μL) was injected into GPC. Using tetrahydrofuran as a mobile phase of GPC, it was allowed to flow at a flow rate of 0.6 mL/minute. Regarding columns, two columns TSKgel SuperHM-H (manufactured by TOSOH Corporation) and one column TSKgel SuperH2000 (manufactured by TOSOH Corporation) were connected in series. A differential refractive index detector (manufactured by Shimadzu Corporation under the trade name of RID-10A) was used as a detector.

Synthesis Example 1

Synthesis of Compound 2

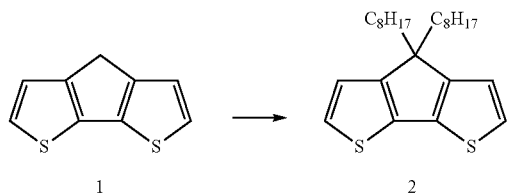

In a four-necked flask, compound 1 (2.674 g, 15.00 mmol), bromooctane (6.083 g, 31.50 mmol), potassium iodide (62.25 mg, 2.5 mol %) and dimethyl sulfoxide (50 mL) were charged, followed by argon bubbling at room temperature (25° C.) for 30 minutes. After cooling to 0° C. using an ice bath, potassium hydroxide (2.525 g, 45.00 mmol) was added and the mixture was reacted for 6 days. The reaction solution was analyzed by liquid chromatography (HPLC) and disappearance of a raw material was confirmed.

Then, pure water was added to the reaction solution and the organic layer was extracted with hexane. The organic layer was separated by a column using hexane as an eluent and the component obtained by separation was dried to obtain 4.11 g of compound 2.

Synthesis Example 2

Synthesis of Compound 3

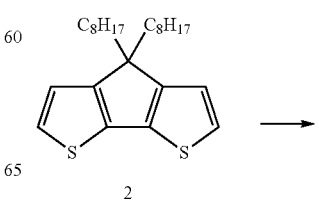

-continued

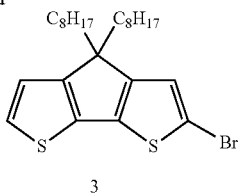
3

In a four-necked flask, compound 2 (4.11 g, 10.2 mmol), and N,N-dimethylformamide (DMF) (200 mL) was charged, followed by argon bubbling at room temperature (25° C.) for 30 minutes. After cooling to −20° C., N-bromosuccineimide (NBS) (1.91 g, 10.71 mmol) was added and the temperature was raised to room temperature (25° C.) over 6 hours. During temperature rise, NBS (182 mg, 1.02 mmol) was added twice.

Then, pure water was added to the reaction solution and the organic layer was extracted with diethylether. The organic layer was separated by a column using hexane as an eluent and the component obtained by separation was dried to obtain 3.17 g of compound 3.

Example 1

Synthesis of Compound 5

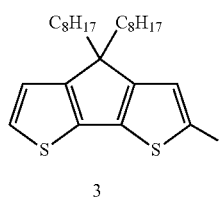
3

+

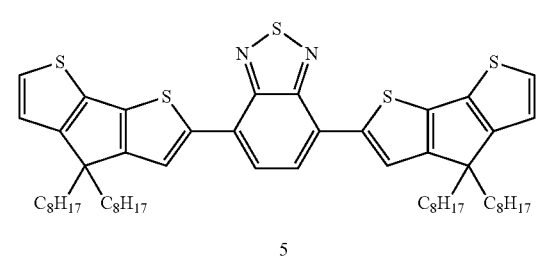
4

↓

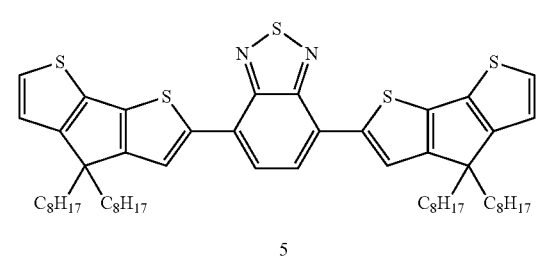
5

In a four-necked flask, compound 4 (1.173 g, 3.021 mmol), compound 3 (3.178 g, 6.042 mmol), toluene (90 mL) and methyltrialkylammonium chloride (trade name: Aliquat336 (registered trademark), manufactured by Aldrich) (606 mg, 1.50 mmol) were charged, followed by argon bubbling at room temperature (25° C.) for 30 minutes. After raising the temperature to 90° C., palladium acetate (6.7 mg, 1 mol %) and tris(2-methoxyphenyl)phosphine (37.0 mg, 3.5 mol %) were added. Then, while stirring at 100° C., an aqueous sodium carbonate solution (16.7% by weight, 19.0 g, 30.0 mmol) was added dropwise over 30 minutes. After 2 hours, the reaction solution was analyzed by HPLC and disappearance of compound 3 was confirmed. The reaction was carried out under an argon atmosphere.

Then, pure water was added to the reaction solution and the toluene layer was separated and then dried to obtain a reaction product. The reaction product was separated by a column using hexane as an eluent to obtain 1.196 g of compound 5.

$^1$H-NMR (CDCl$_3$, δ(ppm)): 0.822 (t, 12H), 1.055 (m, 8H), 1.167 (m, 40H), 1.919 (t, 8H), 6.981 (d, 2H), 7.234 (d, 2H), 7.852 (s, 2H), 8.046 (s, 2H)

Example 2

Synthesis of Compound 6

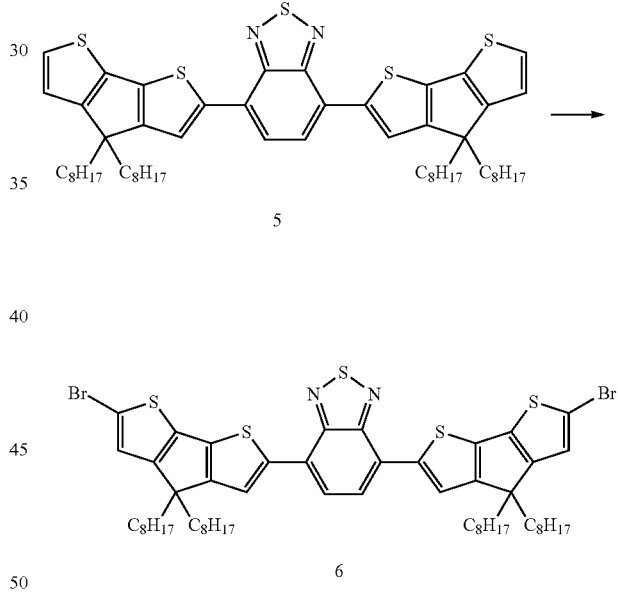

In a four-necked flask, compound 5 (1.190 g, 1.269 mmol), DMF (15 mL) and tetrahydrofuran (THF) (15 mL) were charged, followed by argon bubbling at room temperature (25° C.) for 30 minutes. After cooling to −60° C., NBS (474.3 mg, 2.665 mmol) was added and the temperature was raised to 0° C. over 6 hours. During temperature rise, NBS (22.6 mg, 0.127 mmol) was added twice.

Then, pure water was added to the reaction solution and the organic layer was extracted with hexane. Then, the organic layer was separated by a column using hexane as an eluent and the component obtained by separation was dried to obtain 1.612 g of compound 6.

$^1$H-NMR (CDCl$_3$, δ(ppm)): 0.829 (t, 12H), 1.026 (m, 8H), 1.169 (m, 40H), 1.876 (t, 8H), 6.990 (s, 2H), 7.837 (s, 2H), 8.009 (s, 2H)

Example 3

Synthesis of Polymer A

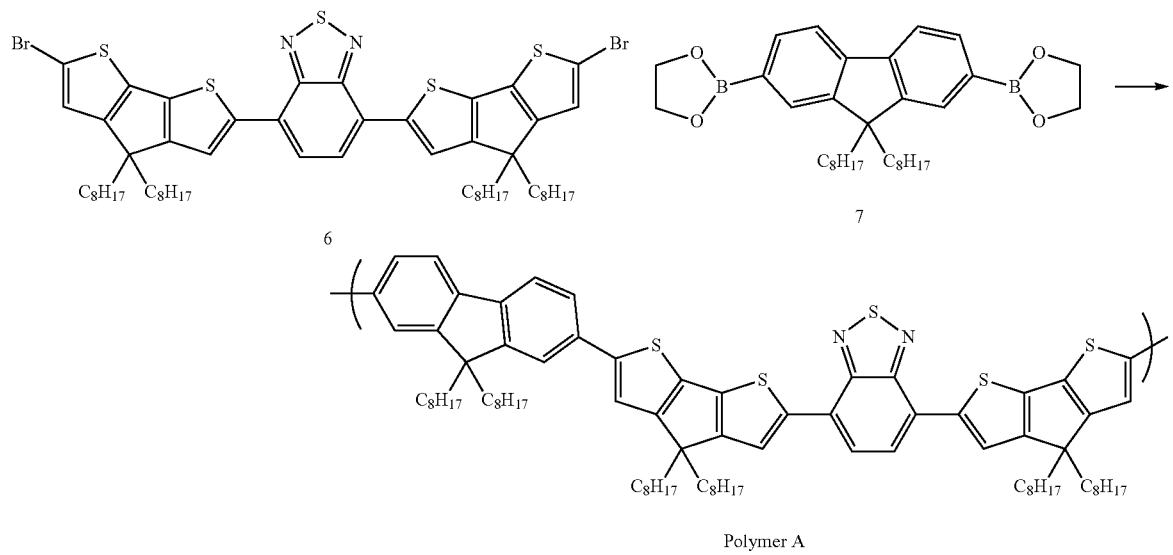

In a four-necked flask, compound 7 (157.8 mg, 0.298 mmol), compound 6 (343.2 mg, 0.313 mmol), toluene (10 mL) and methyltrialkylammonium chloride (trade name: Aliquat336 (registered trademark), manufactured by Aldrich) (60.6 mg, 0.15 mmol) were charged, followed by argon bubbling at room temperature (25° C.) for 30 minutes. After raising the temperature to 90° C., palladium acetate (0.67 mg, 1 mol %) and tris(2-methoxyphenyl)phosphine (3.70 mg, 3.5 mol %) were added. Then, while stirring at 100° C., an aqueous sodium carbonate solution (16.7% by weight, 1.90 g, 3.00 mmol) was added dropwise over 30 minutes. After 4 hours, phenylboric acid (3.66 mg, 0.03 mmol), palladium acetate (0.67 mg, 1 mol %) and tris(2-methoxyphenyl)phosphine (3.70 mg, 3.5 mol %) were added and the mixture was further stirred for one hour, and then the reaction was terminated. The reaction was carried out under an argon atmosphere.

Then, sodium diethyldithiocarbamate (1 g) and pure water (10 mL) were added, followed by stirring while refluxing for one hour. After removing the aqueous layer in the reaction solution, the organic layer was washed twice with 10 ml of water, washed twice with 10 mL of an aqueous acetic acid solution (3% by weight), further washed twice with 10 mL of water and then poured into methanol to precipitate a polymer. The polymer was filtered and dried, and the obtained polymer was dissolved again in toluene (15 mL) and then passed through an alumina/silica gel column, and the obtained solution was poured into methanol to precipitate the polymer. The polymer was filtered and then dried to obtain 160 mg of polymer A.

The polystyrene-equivalent molecular weight of polymer A measured by GPC exhibited a weight average molecular weight (Mw) of 98,000 and a number average molecular weight (Mn) of 49,000.

Polymer A is composed of a structural unit represented by formula (IV) and a structural unit represented by formula (II). The structural unit represented by formula 6-a is one aspect of a structural unit represented by formula (IV), and the structural unit represented by formula 7-a is one aspect of a structural unit represented by formula (II).

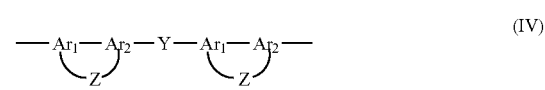 (IV)

 (II)

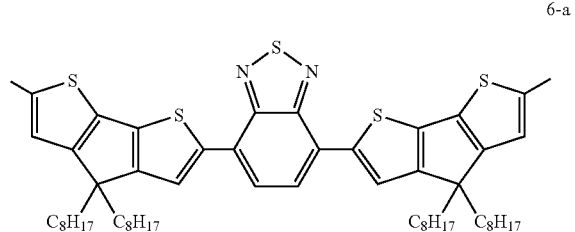 6-a

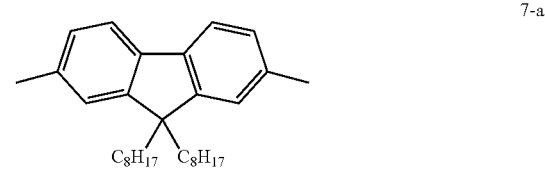 7-a

Example 4

Synthesis of Polymer B

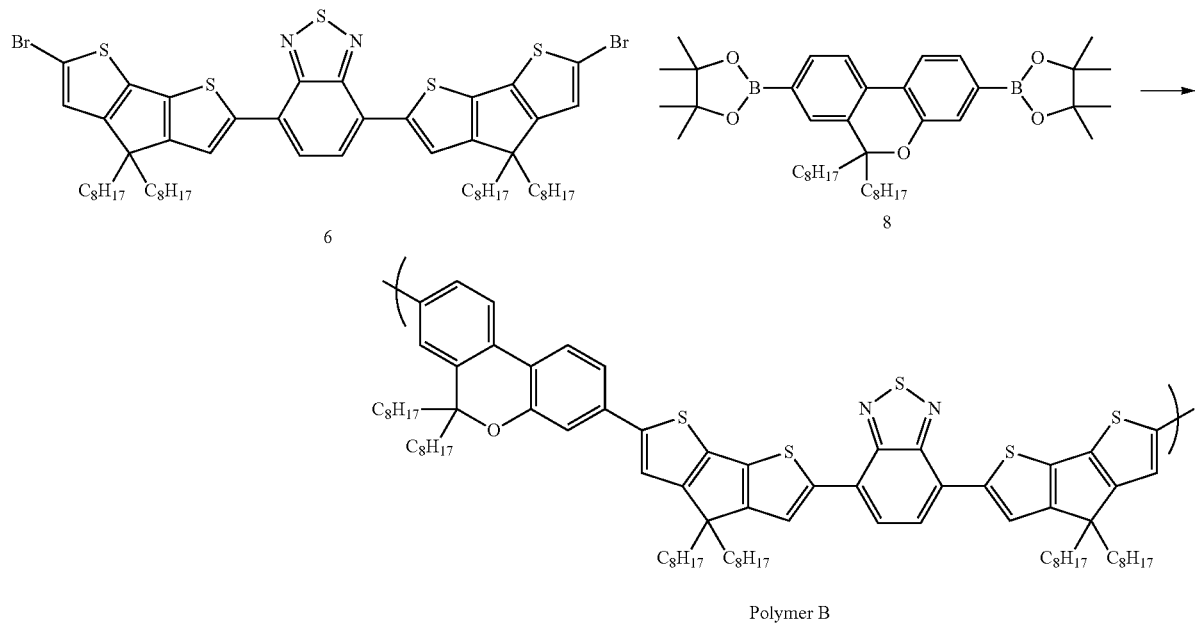

In a four-necked flask, compound 8 (83.6 mg, 0.158 mmol) synthesized in accordance with the description of Example 10 of JP-A-2004-168999, compound 6 (181.9 mg, 0.166 mmol), toluene (10 mL) and methyltrialkylammonium chloride (trade name: Aliquat336 (registered trademark), manufactured by Aldrich) (60.6 mg, 0.15 mmol) were charged, followed by argon bubbling at room temperature (25° C.) for 30 minutes. After raising the temperature to 90° C., palladium acetate (0.67 mg, 1 mol %) and tris(2-methoxyphenyl)phosphine (3.70 mg, 3.5 mol %) were added. Then, while stirring at 100° C., an aqueous sodium carbonate solution (16.7% by weight, 1.90 g, 3.00 mmol) was added dropwise over 30 minutes. After 4 hours, phenylboric acid (3.66 mg, 0.03 mmol), palladium acetate (0.67 mg, 1 mol %) and tris(2-methoxyphenyl)phosphine (3.70 mg, 3.5 mol %) were added and the mixture was stirred for one hour, and then the reaction was terminated. The reaction was carried out under an argon atmosphere.

Then, sodium diethyldithiocarbamate (1 g) and pure water (10 mL) were added, followed by stirring while refluxing for one hour. After removing the aqueous layer in the reaction solution, the organic layer was washed twice with 10 ml of water, washed twice with 10 mL of an aqueous acetic acid solution (3% by weight), further washed twice with 10 mL of water and then poured into methanol to precipitate a polymer. The polymer was filtered and dried, and the obtained polymer was dissolved again in toluene (15 mL) and then passed through an alumina/silica gel column, and the obtained solution was poured into methanol to precipitate the polymer. The polymer was filtered and then dried to obtain 89 mg of polymer B.

The polystyrene-equivalent molecular weight of polymer B measured by GPC exhibited Mw of 51,000 and Mn of 15,000.

Polymer B is composed of a structural unit represented by formula (IV) and a structural unit represented by formula (II). The structural unit represented by formula 6-a is one aspect of a structural unit represented by formula (IV), and the structural unit represented by formula 8-a is one aspect of a structural unit represented by formula (II).

$$-Ar_1-Ar_2-Y-Ar_1-Ar_2- \quad (IV)$$
$$\phantom{-Ar_1-}\underset{Z}{\underbrace{\phantom{AAA}}}\phantom{-Y-}\underset{Z}{\underbrace{\phantom{AAA}}}$$

$$-D- \quad (II)$$

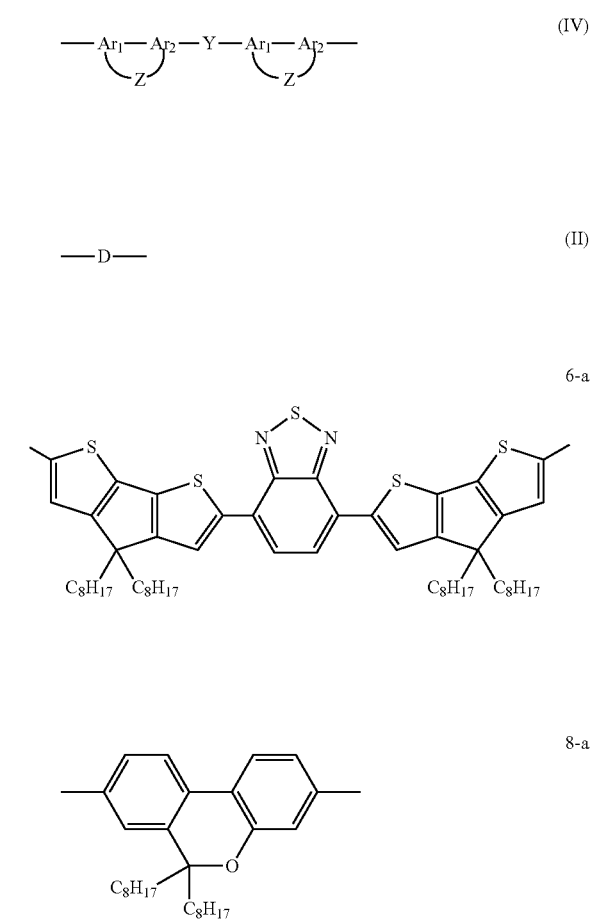

Example 5

Synthesis of Compound 10

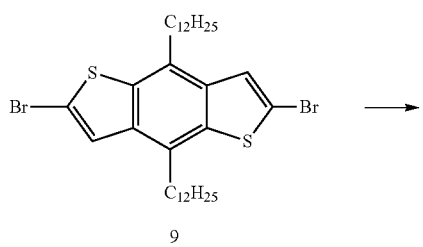

In a four-necked flask, compound 9 (6.847 g, 10.00 mmol), bispinacolatodiboron (10.16 g, 40.00 mmol) and dioxane (150 mL) were charged, followed by argon bubbling at room temperature (25° C.) for 30 minutes. Diphenylphosphinoferrocene palladium dichloride (408.3 mg, 5 mol %), diphenylphosphinoferrocene (277.2 mg, 5 mol %) and potassium acetate (3.926 g, 40.00 mmol) were added and then the mixture was heated at reflux for 10 hours. After completion of the reaction, the reaction solution was analyzed by HPLC and disappearance of the raw material was confirmed.

Using a filter, a base slightly soluble in a reaction solution was separated. Then, the solution was dried by an evaporator for about 30 minutes to remove dioxane. The reaction product was separated by a column using hexane as an eluent and the component obtained by separation was washed with methanol for 3 hours to obtain a light brown powder. The powder was dissolved in hexane (100 mL) and then recrystallized by being left to stand in a state where ethanol (100 mL) is added to obtain 1.386 g of compound 10.

$^1$H-NMR (CDCl$_3$, δ(ppm)): 0.880 (t, 6H), 1.261 (m, 36H), 1.409 (m, 24H), 1.793 (m, 4H), 3.208 (t, 4H), 8.022 (s, 2H)

Example 6

Synthesis of Polymer C

In a four-necked flask, compound 10 (91.2 mg, 0.117 mmol), compound 6 (135.0 mg, 0.123 mmol), toluene (10 mL) and methyltrialkylammonium chloride (trade name: Aliquat336 (registered trademark), manufactured by Aldrich) (60.6 mg, 0.15 mmol) were charged, followed by argon bubbling at room temperature (25° C.) for 30 minutes. After raising to the temperature to 90° C., palladium acetate (0.67 mg, 1 mol %) and tris(2-methoxyphenyl)phosphine (3.70 mg, 3.5 mol %) were added. Then, while stirring at 100° C., an aqueous sodium carbonate solution (16.7% by weight, 1.90 g, 3.00 mmol) was added dropwise over 30 minutes. After 4 hours, phenylboric acid (3.66 mg, 0.03 mmol), palladium acetate (0.67 mg, 1 mol %) and tris(2-methoxyphenyl)phosphine (3.70 mg, 3.5 mol %) were added and the mixture was stirred for one hour, and then the reaction was terminated. The reaction was carried out under an argon atmosphere.

Then, sodium diethyldithiocarbamate (1 g) and pure water (10 mL) were added, followed by stirring while refluxing for one hour. After removing the aqueous layer in the reaction solution, the organic layer was washed twice with 10 ml of water, washed twice with 10 mL of an aqueous acetic acid solution (3% by weight), further washed twice with 10 mL of water and then poured into methanol to precipitate a polymer. The polymer was filtered and dried, and the obtained polymer was dissolved again in toluene (15 mL) and then passed through an alumina/silica gel column, and the obtained solution was poured into methanol to precipitate the polymer. The polymer was filtered and then dried to obtain 60 mg of polymer C.

The polystyrene-equivalent molecular weight of polymer C measured by GPC exhibited Mw of 29,000 and Mn of 15,000.

Polymer C is composed of a structural unit represented by formula (IV) and a structural unit represented by formula (II). The structural unit represented by formula 6-a is one aspect of a structural unit represented by formula (IV), and the structural unit represented by formula 10-a is one aspect of a structural unit represented by formula (II).

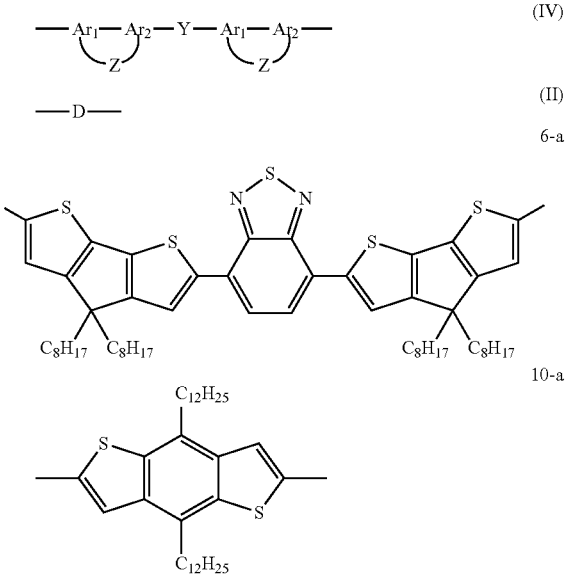

Synthesis Example 3

Synthesis of Compound 12

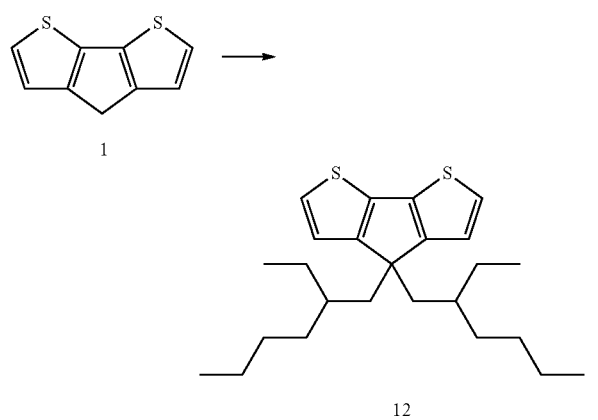

In a 200 mL flask in which a gas in the flask was replaced by argon, compound 1 (1.78 g, 10.0 mmol), 2-ethylhexyl bromide (5.83 g, 25.0 mmol), potassium iodide (41.5 mg, 0.25 mmol) and potassium hydroxide (1.68 g, 30.0 mmol) were charged and dissolved in dimethyl sulfoxide (35 mL), followed by stirring at room temperature (25° C.) for 24 hours stirring. After completion of the reaction, 100 mL of water was added and the product was extracted with hexane and then purified by silica gel column (eluent is hexane) to obtain 2.61 g of compound 12.

Synthesis Example 4

Synthesis of Compound 13

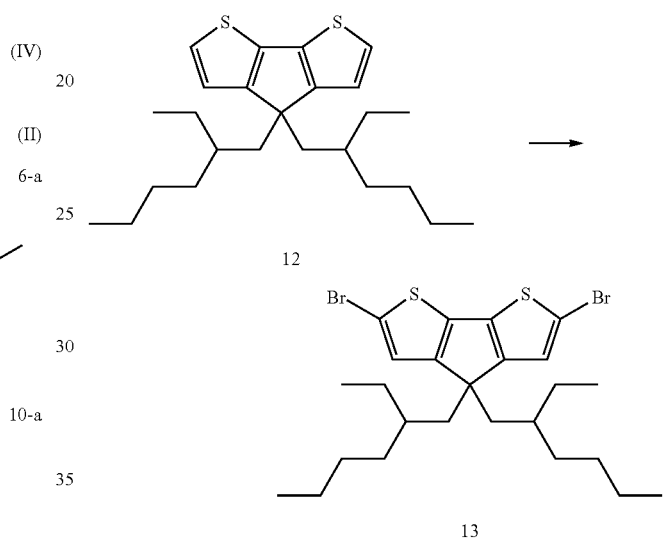

In a 200 mL flask in which a gas in the flask was replaced by argon, compound 12 (1.31 g, 3.25 mmol) synthesized in Synthesis Example 3 and DMF (25 mL) were charged. After cooling the flask to 0° C., NBS (1.21 g) was charged, followed by stirring for 12 hours. The reaction was terminated by pouring 100 mL of water in the reaction solution, and the product was extracted with ether. The product was purified by silica gel column (eluent is hexane) to obtain 1.70 g of compound 13.

Synthesis Example 5

Synthesis of Polymer D

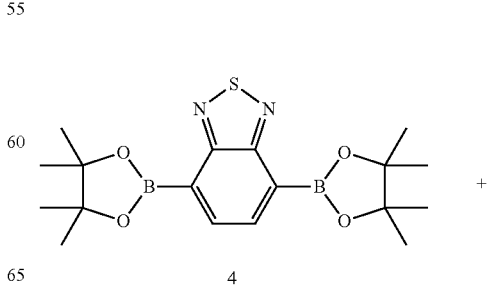

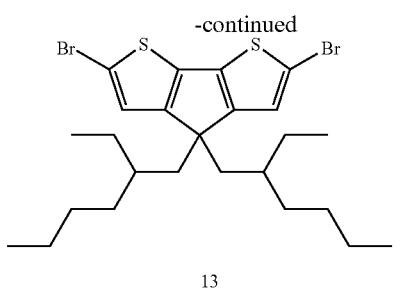

13

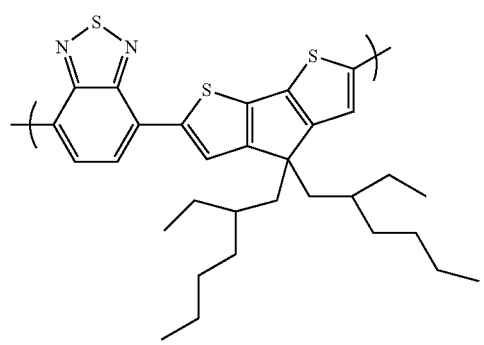

Polymer D

In a 200 mL flask in which a gas in the flask was replaced by argon, compound 13 (561 mg, 1.00 mmol) synthesized in Synthesis Example 4, compound 4 (4,7-bis(4,4,5,5-tetramethyl-1,3,2-dioxaborolan-2-yl)-2,1,3-benzothiadiazole) (manufactured by Aldrich) (388.1 mg, 1.00 mmol) and 202 mg of methyltrialkylammonium chloride (trade name: Aliquat336 (registered trademark), manufactured by Aldrich) were charged and dissolved in 20 ml of toluene, and then the obtained toluene solution was bubbled with argon for 30 minutes. Then, 2.25 mg of palladium acetate, 12.3 mg of tris(2-methoxyphenyl)phosphine) and 6.5 mL of an aqueous sodium carbonate solution (16.7% by weight) were added, followed by stirring at 100° C. for 5 hours. Then, 50 mg of phenylboric acid was added and the mixture was reacted at 70° C. for 2 hours. Then, 2 g of sodium diethyldithiocarbamate and 20 mL of water were added, followed by stirring under reflux for 2 hours. After removing the aqueous layer in the reaction solution, the organic layer was washed twice with 20 ml of water, washed twice with 20 mL of an aqueous acetic acid solution (3% by weight), further washed twice with 20 mL of water and then poured into methanol to precipitate a polymer. The polymer was filtered and dried, and the obtained polymer was dissolved again in 30 mL of o-dichlorobenzene and then passed through an alumina/silica gel column, and the obtained solution was poured into methanol to precipitate the polymer. The polymer was filtered and then dried to obtain 280 mg of a purified polymer. Hereinafter, the obtained polymer is referred to as polymer D. The polystyrene-equivalent molecular weight of polymer D measured by GPC exhibited Mw of 30,000 and Mn of 14,000.

Example 7

Synthesis of Polymer E

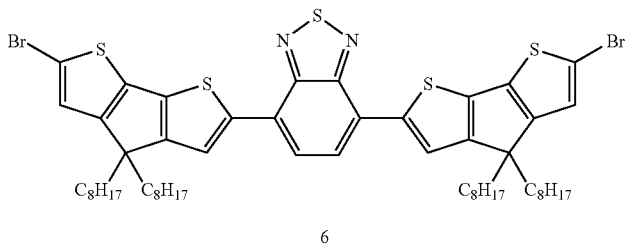

6

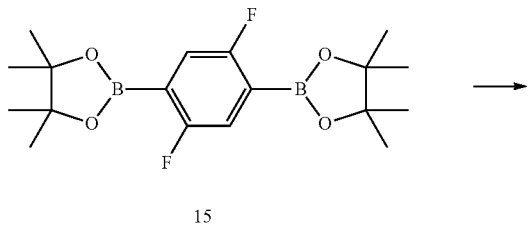

15

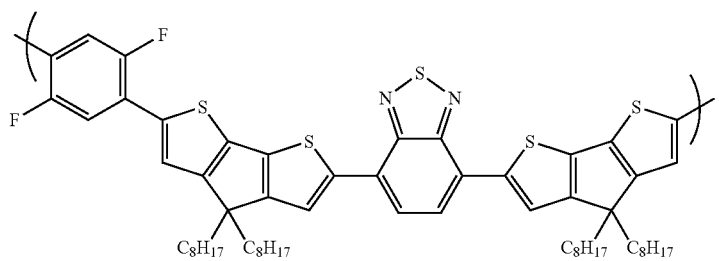

Polymer E

In a four-necked flask, the compound 15 (64.8 mg, 0.177 mmol), compound 6 (203.9 mg, 0.186 mmol) and tetrahydrofuran (10 mL) were charged, followed by argon bubbling at room temperature (25° C.) for 30 minutes. Then, tris(dibenzylideneacetone)palladium (5.49 mg, 0.006 mmol) and [tri(tertiary butyl)phosphonium]tetrafluoroborate (6.96 mg, 0.024 mmol) were added. While stirring at 80° C., an aqueous potassium carbonate solution (27.6% by weight, 1.50 g, 3.00 mmol) was added dropwise over 30 minutes. After 15 minutes, phenylboric acid (3.66 mg, 0.03 mmol) was added and the mixture was stirred for one hour, and then the reaction was terminated. The reaction was carried out under an argon atmosphere.

Then, sodium diethyldithiocarbamate (1 g) and pure water (10 mL) were added, followed by stirring while refluxing for one hour. After removing the aqueous layer in the reaction solution, the organic layer was washed twice with 10 ml of water, washed twice with 10 mL of an aqueous acetic acid solution (3% by weight), further washed twice with 10 mL of water and then poured into methanol to precipitate a polymer. The polymer was filtered and dried, and the obtained polymer was dissolved in toluene. Then the toluene solution was passed through an alumina/silica gel column, and then the obtained solution was poured into methanol to precipitate the polymer. The polymer was filtered and then dried to obtain 64 mg of polymer E.

The polystyrene-equivalent molecular weight of polymer E measured by GPC exhibited a weight average molecular weight (Mw) of 8,000 and a number average molecular weight (Mn) of 6,000.

Polymer E is composed of a structural unit represented by formula (IV) and a structural unit represented by formula (II). The structural unit represented by formula 6-a is one aspect of a structural unit represented by formula (IV), and the structural unit represented by formula 15-a is one aspect of a structural unit represented by formula (II).

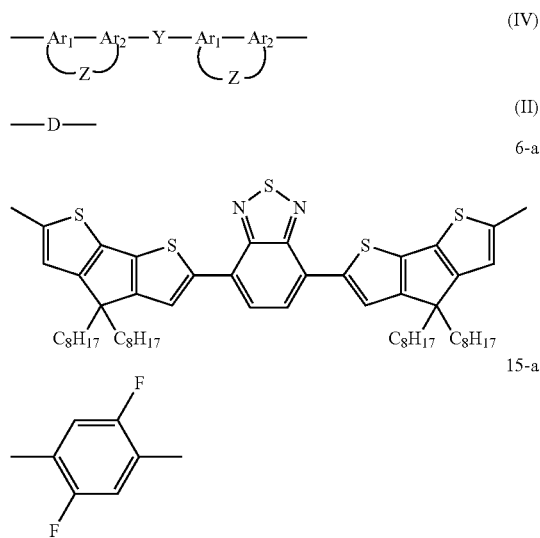

Example 8

Production and Evaluation of Ink and Organic Thin Film Solar Battery

A glass substrate with ITO film formed thereon in a thickness of 150 nm by a sputter method was subjected to a surface treatment by an ozone-UV treatment. Then, a polymer A and fullerene C60PCBM (phenyl C61-butyric acid methyl ester, manufactured by Frontier Carbon Corporation) (weight ratio polymer A/C60PCBM=1/3) was dissolved in orthodichlorobenzene (total weight of polymer A and C60PCBM is 2.0% by weight) and ink 1 was prepared. The thus prepared ink 1 was applied on the glass substrate by spin coating to form an organic film containing polymer A (film thickness of about 100 nm). A light absorption edge wavelength of the thus obtained organic film was 750 nm. Lithium fluoride was deposited on the organic film in a thickness of 2 nm by a vacuum deposition apparatus and then Al was deposited thereon in a thickness of 100 nm to produce an organic thin film solar battery. The obtained organic thin film solar battery had a regular square measuring 2 mm×2 mm. The obtained organic thin film solar battery was irradiated with given light using a solar simulator (manufactured by BUNKOUKEIKI Co., Ltd. under the trade name of OTENTO-SUNII:AM1.5G filter, irradiance 100 mW/cm$^2$) and then the generated current and voltage were measured to determine photoelectric conversion efficiency, short-circuit current density, open-end voltage and fill factor. The short-circuit current density (Jsc) was 5.46 mA/cm$^2$, the open-end voltage (Voc) was 0.70 V, the fill factor (ff) was 0.47 and the photoelectric conversion efficiency ($\eta$) was 1.80%. The results are shown in Table 1.

Example 9

In the same manner as in Example 8, except that polymer B was used in place of polymer A, ink and an organic thin film solar battery were produced and evaluated. As a result, the short-circuit current density (Jsc) was 4.85 mA/cm$^2$, the open-end voltage (Voc) was 0.72 V, the fill factor (ff) was 0.45 and the photoelectric conversion efficiency ($\eta$) was 1.57%. The results are shown in Table 1.

Example 10

In the same manner as in Example 8, except that the polymer E was used in place of polymer A, ink and an organic thin film solar battery were produced and evaluated. As a result, the short-circuit current density (Jsc) was 9.90 mA/cm$^2$, the open-end voltage (Voc) was 0.61 V, the fill factor (ff) was 0.44 and the photoelectric conversion efficiency ($\eta$) was 2.64%. The results are shown in Table 1.

Comparative Example 1

In the same manner as in Example 8, except that polymer D was used in place of polymer A, ink and an organic thin film solar battery were produced and evaluated. As a result, the short-circuit current density (Jsc) was 4.61 mA/cm$^2$, the open-end voltage (Voc) was 0.60 V, the fill factor (ff) was 0.33 and the photoelectric conversion efficiency ($\eta$) was 0.91%. The results are shown in Table 1.

TABLE 1

Evaluation results of photoelectric conversion device

| | | Short-circuit current density (mA/cm$^2$) | Open-end voltage (V) | Fill factor | Photoelectric conversion efficiency (%) |
|---|---|---|---|---|---|
| Example 8 | Polymer A | 5.46 | 0.70 | 0.47 | 1.80 |
| Example 9 | Polymer B | 4.83 | 0.72 | 0.45 | 1.57 |

TABLE 1-continued

Evaluation results of photoelectric conversion device

| | | Short-circuit current density (mA/cm²) | Open-end voltage (V) | Fill factor | Photoelectric conversion efficiency (%) |
|---|---|---|---|---|---|
| Example 10 | Polymer E | 9.90 | 0.61 | 0.44 | 2.64 |
| Comparative Example 1 | Polymer D | 4.61 | 0.60 | 0.33 | 0.91 |

Example 11

Production of Organic Transistor

An n-type silicon substrate (doped in high concentration) with a 300 nm thick thermally oxidized film was ultrasonic-washed in acetone for 10 minutes and then irradiated with ozone-UV for 20 minutes. Then, a surface of the thermally oxidized film was silane-treated by spin coating of beta-phenethyltrichlorosilane diluted in the proportion of 5 droplets (added dropwise after weighing using a syringe) to 10 ml of toluene.

Then, polymer C produced in Example 6 was dissolved in chloroform to prepare a solution having the concentration of polymer C of 0.5% by weight and then the solution was filtered through a membrane filter to prepare a coating solution. The coating solution was applied on the above-mentioned surface-treated substrate by a spin coating method to form a coating film (thickness of about 60 nm) of polymer C. Furthermore, the coating film was heat-treated in a nitrogen atmosphere at 120° C. for 30 minutes to form an organic semiconductor thin film of polymer C. Furthermore, a source electrode and a drain electrode (having a laminated structure of molybdenum trioxide and gold) were formed on the organic semiconductor thin film from the organic semiconductor thin film side by a vacuum deposition method using a metal mask to produce an organic transistor.

Example 12

Evaluation of Organic Transistor

Electric characteristics of the organic transistor were measured using a semiconductor parameter 4200 (manufactured by KEITHLEY). As a result, it could be confirmed that a curve of a change in drain current (Id) versus a drain voltage (Vd) is satisfactory, and that the organic transistor is a p-type organic transistor since a negative drain current increases when a negative gate voltage to be applied to the gate electrode is increased. A saturation electron field-effect mobility p of a carrier in the organic transistor was calculated using the following formula (a) showing a drain current Id in a saturation region of electric characteristics of the organic transistor:

$$Id = (W/2L)\mu Ci(Vg-Vt)^2 \quad (a)$$

wherein L denotes a channel length of an organic transistor, W denotes a channel width of an organic transistor, Ci denotes a capacity per unit area of a gate insulating film, Vg denotes a gate voltage, and Vt denotes a threshold value voltage of a gate voltage.

As a result, the electron field-effect mobility (carrier mobility) of the carrier was $2.35 \times 10^{-2}$ cm²/Vs and the on/off current ratio was $10^5$.

Example 13

In the same manner as in Example 11, except that polymer A was used in place of polymer C, an organic transistor element was produced. In the same manner as in Example 12, transistor characteristics were evaluated. As a result, the carrier mobility was $3.84 \times 10^{-3}$ cm²/Vs and the on/off current ratio was $10^5$.

Example 14

In the same manner as in Example 11, except that polymer E was used in place of polymer C, an organic transistor element was produced. In the same manner as in Example 12, transistor characteristics were evaluated. As a result, the carrier mobility was $1.62 \times 10^{-3}$ cm²/Vs and the on/off current ratio was $10^5$.

Comparative Example 2

In the same manner as in Example 11, except that polymer D was used in place of polymer C, an organic transistor element was produced. In the same manner as in Example 12, transistor characteristics were evaluated. As a result, the carrier mobility was $1.57 \times 10^{-3}$ cm²/Vs and the on/off current ratio was $10^4$.

TABLE 2

Evaluation results of organic transistor device

| | | Carrier mobility (cm²/Vs) | On/off ratio |
|---|---|---|---|
| Example 12 | Polymer C | $2.35 \times 10^{-2}$ | $10^5$ |
| Example 13 | Polymer A | $3.84 \times 10^{-3}$ | $10^5$ |
| Example 14 | Polymer E | $1.62 \times 10^{-3}$ | $10^5$ |
| Comparative Example 2 | Polymer D | $1.57 \times 10^{-3}$ | $10^4$ |

INDUSTRIAL APPLICABILITY

The polymer compound of the present invention is useful since photoelectric conversion efficiency increases when used in an organic photoelectric conversion device.

The invention claimed is:

1. A polymer compound including a structural unit represented by formula (V) and a structural unit represented by formula (II):

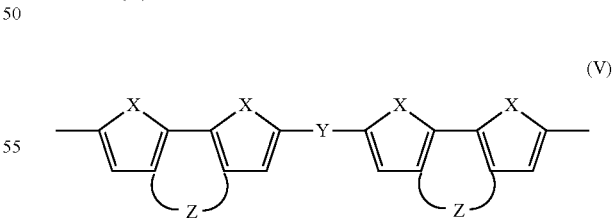

(V)

wherein X represents a sulfur atom, an oxygen atom, a selenium atom, —NH— or —N(R$^a$)—; R$^a$ represents a substituent; Y represents a divalent heterocyclic group represented by formula (Y-1) to (Y-5); Z represents a divalent group represented by (Z-1) and two Zs may be the same or different;

wherein the divalent heterocyclic group represented by Y is each of groups represented by formulas (Y-1) to (Y-5):

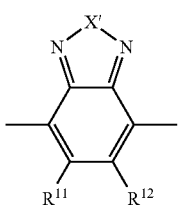
(Y-1)

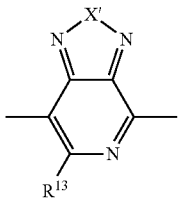
(Y-2)

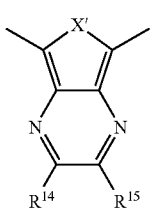
(Y-3)

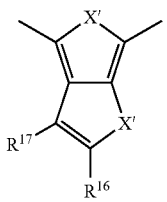
(Y-4)

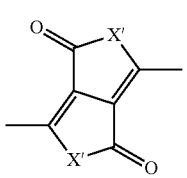
(Y-5)

wherein X' represents a sulfur atom, an oxygen atom, a selenium atom, —NH— or —N(R$^a$); R$^a$ represents a substituent; R$^{11}$ to R$^{17}$ are the same or different and represent a hydrogen atom or a substituent; R$^{11}$ and R$^{12}$ may be connected to each other to form a cyclic structure; and plural X's are present, they may be the same or different;

(Z-1)

wherein R$^1$ and R$^2$ are the same or different and represent a hydrogen atom or a substituent;

—D— (II)

wherein D represents an arylene group or a fused ring heteroarylene group, provided that a divalent heterocyclic group represented by Y is different from a group represented by D, and a group represented by D is different from the group represented by (VA):

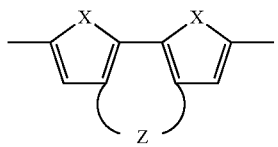
(Va)

wherein Y and Z have the same meanings as above.

2. The polymer compound according to claim 1, wherein a structural unit represented by formula (II) is a group represented by formula (D-4):

(D-4)

wherein d" ring represents a benzene ring which may have a substituent, a biphenyl ring which may have a substituent, a terphenyl ring which may have a substituent, or a fused ring containing a hetero atom, which may have a substituent.

3. The polymer compound according to claim 1, wherein a polystyrene-equivalent number average molecular weight is 3,000 or more.

4. A thin film comprising the polymer compound according to claim 1.

5. A composition comprising the polymer compound according to claim 1 and an electron accepting compound.

6. The composition according to claim 5, wherein the electron accepting compound is a fullerene derivative.

7. A thin film comprising the composition according to claim 5.

8. A solution comprising the composition according to claim 5 and a solvent.

9. An electronic element using the thin film according to claim 4.

10. The polymer compound according to claim 1, wherein a structural unit represented by formula (II) is each of groups represented by formulas (D-1) to (D-3):

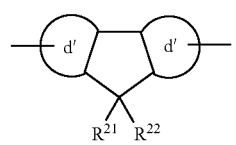
(D-1)

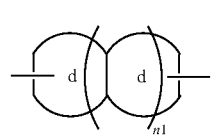
(D-2)

(D-3)
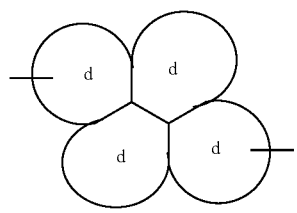
wherein d and d' ring in formulas (D-1) to (D-3) represents an aromatic ring which may have a substituent; plural d rings may be the same or different; plural d' rings may be the same or different; $R^{21}$ and $R^{22}$ are the same or different and represent a hydrogen atom or a substituent; and n1 is an integer of 1 or more.
* * * * *